(12) United States Patent
Bennett et al.

(10) Patent No.: US 11,026,647 B2
(45) Date of Patent: Jun. 8, 2021

(54) SIMULTANEOUS MULTI-AXES IMAGING APPARATUS AND METHOD OF USE THEREOF

(71) Applicants: James P. Bennett, Birmingham, AL (US); W. Davis Lee, Rockport, ME (US)

(72) Inventors: James P. Bennett, Birmingham, AL (US); W. Davis Lee, Rockport, ME (US)

( * ) Notice: Subject to any disclaimer, the term of this patent is extended or adjusted under 35 U.S.C. 154(b) by 0 days.

(21) Appl. No.: 16/548,717

(22) Filed: Aug. 22, 2019

(65) Prior Publication Data

US 2019/0374178 A1 Dec. 12, 2019

Related U.S. Application Data

(63) Continuation of application No. 15/430,208, filed on Feb. 10, 2017, now Pat. No. 10,555,710, which is a
(Continued)

(51) Int. Cl.
*A61B 6/00* (2006.01)
*A61N 5/10* (2006.01)
(Continued)

(52) U.S. Cl.
CPC ............ *A61B 6/4417* (2013.01); *A61B 6/037* (2013.01); *A61B 6/12* (2013.01); *A61B 6/4014* (2013.01); *A61B 6/4085* (2013.01); *A61B 6/4216* (2013.01); *A61B 6/4258* (2013.01); *A61B 6/5211* (2013.01); *A61N 5/1037* (2013.01); *A61N 5/1049* (2013.01); *A61N 5/1067* (2013.01); *A61N 5/1077* (2013.01); *A61N 5/1082* (2013.01); *G21K 1/08* (2013.01); *G21K 5/04* (2013.01); *A61B 6/032* (2013.01);
(Continued)

(58) Field of Classification Search
CPC . A61N 5/00; A61N 5/022; A61N 5/01; A61N 5/1065; A61N 5/1067; A61N 5/1069; A61N 5/107; A61N 5/1071; A61N 5/1072; A61N 5/1074; A61N 5/1076; A61N 5/1078; A61N 5/1081; A61N 5/1087
USPC ............................... 250/492.1, 492.3, 493.1
See application file for complete search history.

(56) References Cited

U.S. PATENT DOCUMENTS

| | | | | |
|---|---|---|---|---|
| 5,818,058 A | * | 10/1998 | Nakanishi | A61N 5/10 250/492.3 |
| 8,632,448 B1 | * | 1/2014 | Schulte | A61N 5/1071 600/1 |
| 2009/0065717 A1 | * | 3/2009 | Kaiser | A61N 5/1049 250/505.1 |

* cited by examiner

*Primary Examiner* — Jason L McCormack
(74) *Attorney, Agent, or Firm* — Kevin Hazen; Hazen Patent Group, LLC

(57) ABSTRACT

The invention comprises a method and apparatus for imaging a tumor with X-rays while, simultaneously or alternatingly, treating or imaging the tumor with positively charged particles. An X-ray imaging system, such as one or two sets of a cone beam X-ray source coupled to an X-ray detector, is rotatable about a first axis and a patient. The X-ray imaging system is positioned off axis a path of charged particles delivered through an exit port of a nozzle system from a synchrotron and does not block a path of the positively charged particles from the exit nozzle to the patient or an imaging path from the patient to a scintillation detector. Fiducial indicators are used to confirm an unobstructed path of the positively charged particles in a treatment room comprising many movable elements, such as the X-ray imaging system and a patient positioning system/couch.

6 Claims, 37 Drawing Sheets

Related U.S. Application Data continuation-in-part of application No. 15/402,739, filed on Jan. 10, 2017, now Pat. No. 10,188,877, which is a continuation-in-part of application No. 15/348,625, filed on Nov. 10, 2016, now Pat. No. 9,855,444, which is a continuation-in-part of application No. 15/167,617, filed on May 27, 2016, now Pat. No. 9,737,733, which is a continuation-in-part of application No. 15/152,479, filed on May 11, 2016, now Pat. No. 10,213,626, which is a continuation-in-part of application No. 14/216,788, filed on Mar. 17, 2014, now Pat. No. 9,682,254, which is a continuation-in-part of application No. 13/087,096, filed on Apr. 14, 2011, now Pat. No. 9,044,600.

(60) Provisional application No. 61/324,776, filed on Apr. 16, 2010.

(51) Int. Cl.
*A61B 6/03* (2006.01)
*G21K 1/08* (2006.01)
*G21K 5/04* (2006.01)
*A61B 6/12* (2006.01)

(52) U.S. Cl.
CPC ............ *A61B 6/4266* (2013.01); *A61B 6/482* (2013.01); *A61B 6/485* (2013.01); *A61B 6/487* (2013.01); *A61B 6/5205* (2013.01); *A61B 6/582* (2013.01); *A61N 5/107* (2013.01); *A61N 2005/1051* (2013.01); *A61N 2005/1054* (2013.01); *A61N 2005/1061* (2013.01); *A61N 2005/1087* (2013.01); *A61N 2005/1095* (2013.01); *A61N 2005/1097* (2013.01)

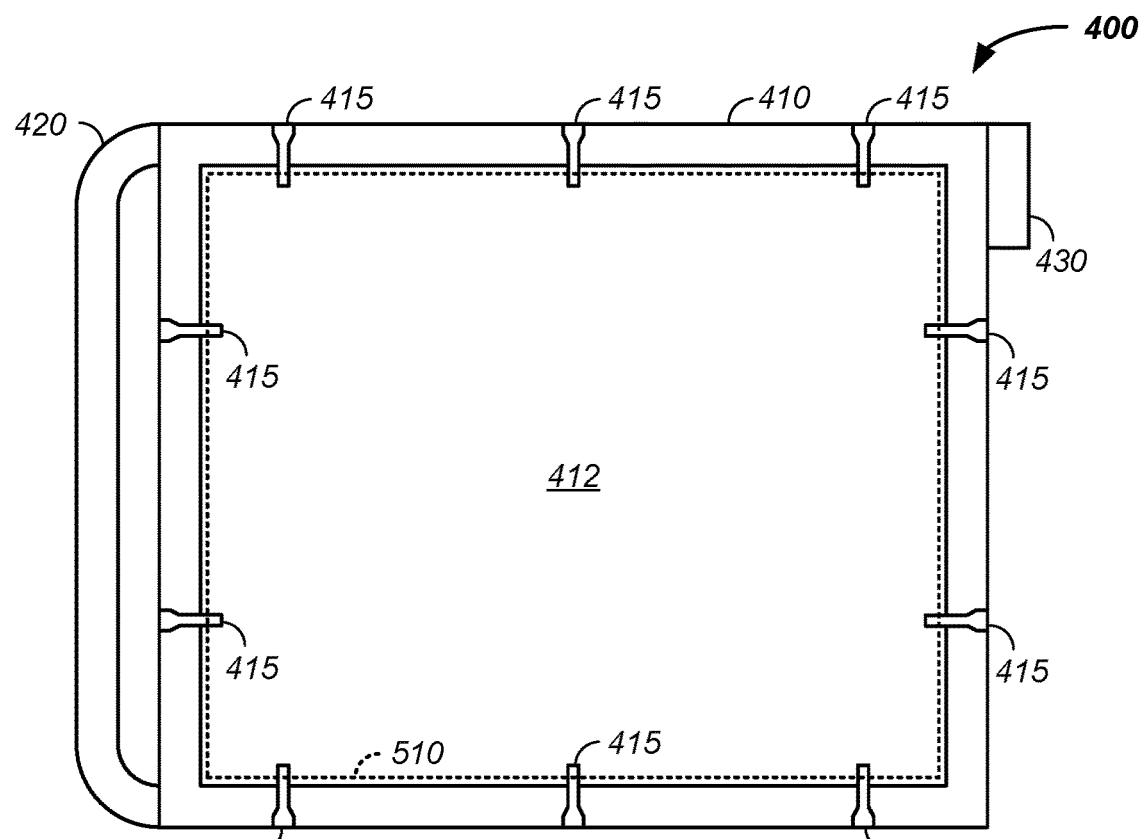
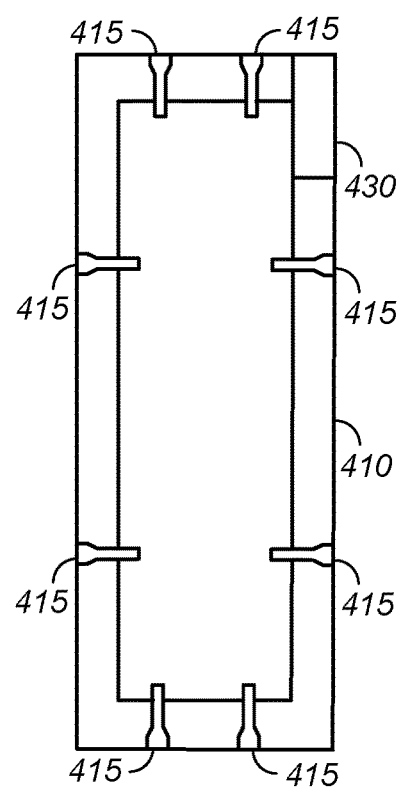
FIG. 4A
FIG. 4B

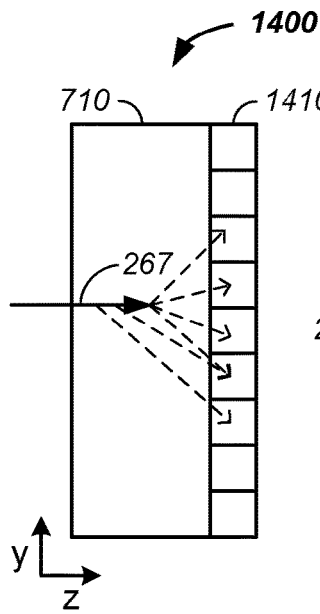 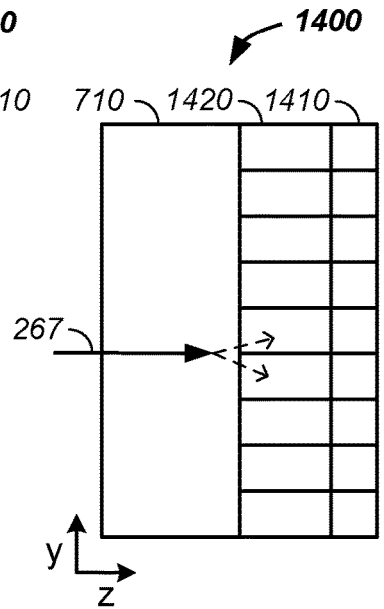 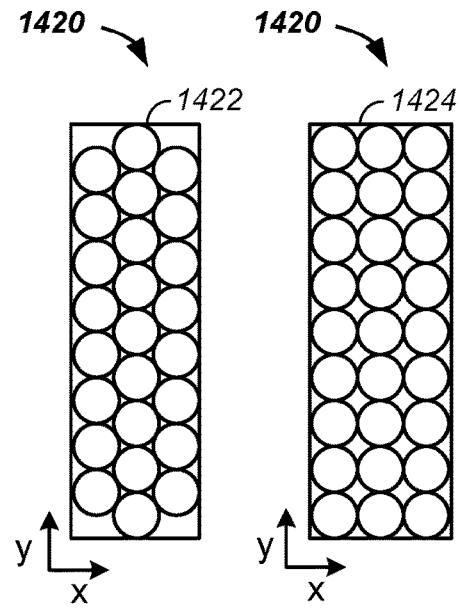 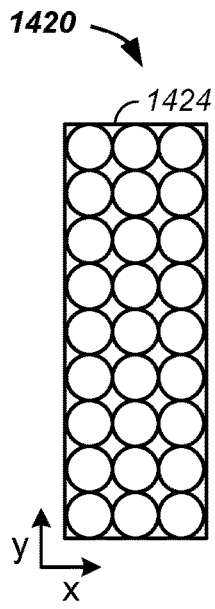
FIG. 14A  FIG. 14B  FIG. 14C  FIG. 14D
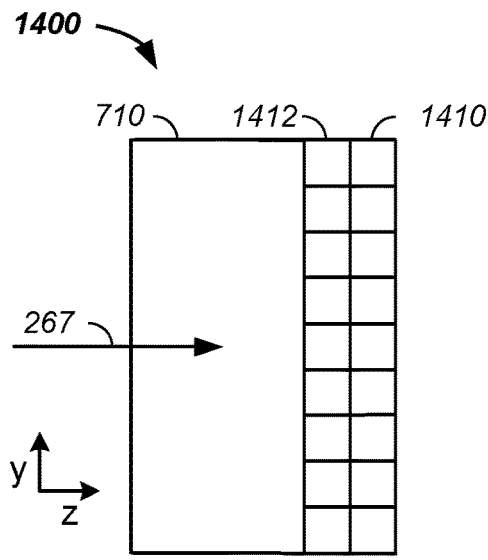 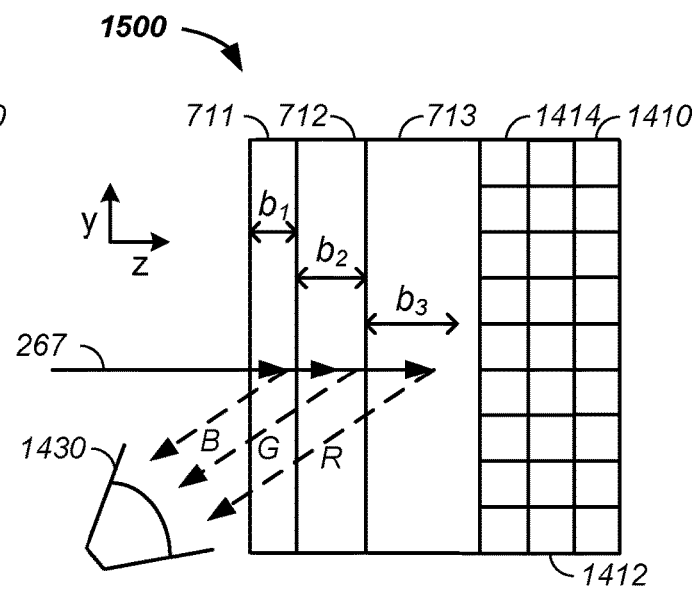
FIG. 14E  FIG. 15

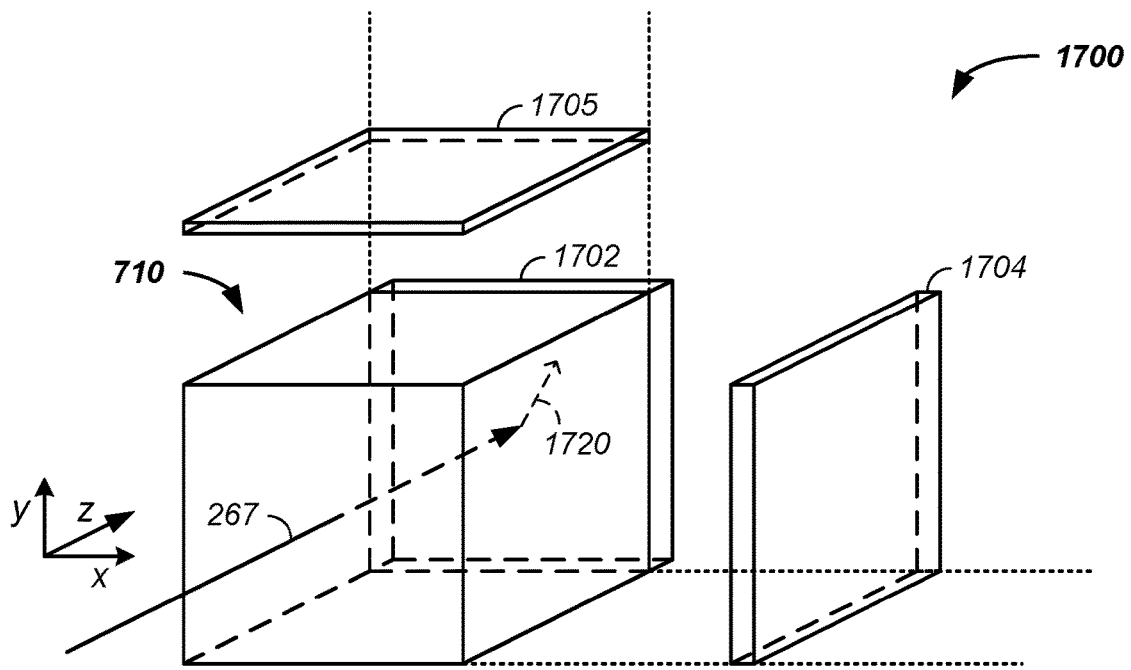
FIG. 17B
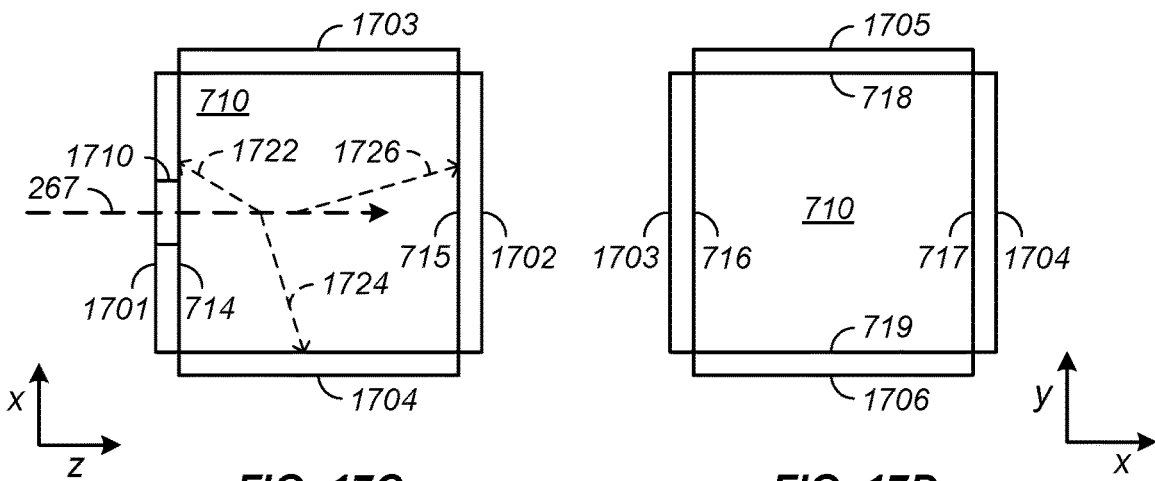
FIG. 17C          FIG. 17D

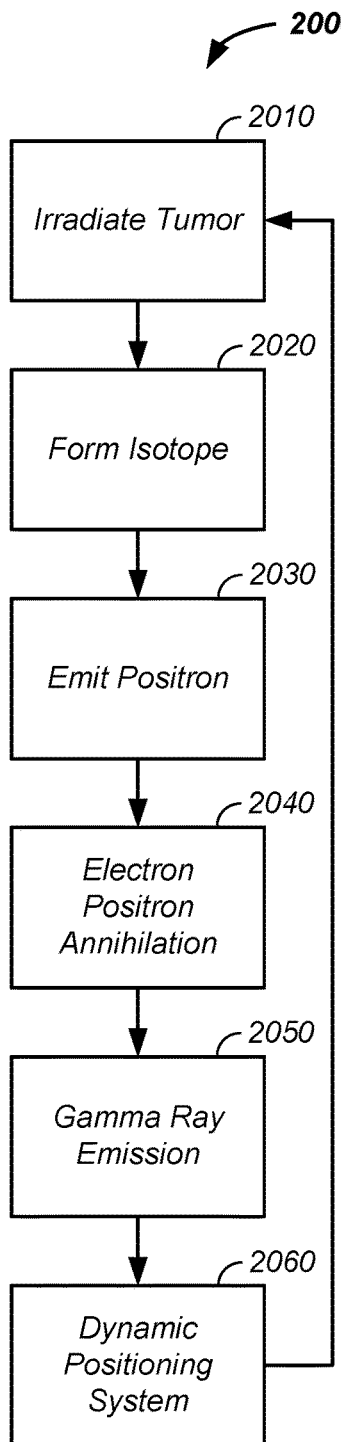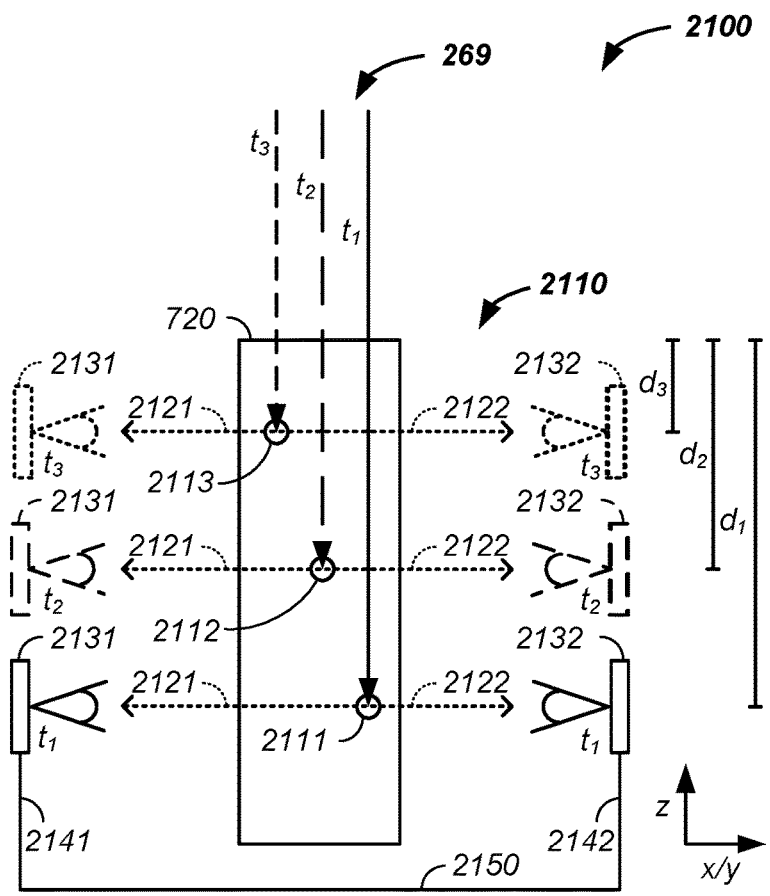
FIG. 20
FIG. 21

SIMULTANEOUS MULTI-AXES IMAGING APPARATUS AND METHOD OF USE THEREOF

CROSS-REFERENCES TO RELATED APPLICATIONS

This application is a continuation of U.S. patent application Ser. No. 15/430,208 filed Feb. 10, 2017, which is a continuation-in-part of U.S. patent application Ser. No. 15/402,739 filed Jan. 10, 2017, which is a continuation-in-part of U.S. patent application Ser. No. 15/348,625 filed Nov. 10, 2016, which is a continuation-in-part of U.S. patent application Ser. No. 15/167,617 filed May 27, 2016, which is a continuation-in-part of U.S. patent application Ser. No. 15/152,479 filed May 11, 2016, which is a continuation-in-part of U.S. patent application Ser. No. 14/216,788 filed Mar. 17, 2014, which is a continuation-in-part of U.S. patent application Ser. No. 13/087,096 filed Apr. 14, 2011, which claims benefit of U.S. provisional patent application No. 61/324,776 filed Apr. 16, 2010, all of which are incorporated herein in their entirety by this reference thereto.

BACKGROUND OF THE INVENTION

Field of the Invention

The invention relates generally to imaging and treating a tumor.

Discussion of the Prior Art

Cancer Treatment

Proton therapy works by aiming energetic ionizing particles, such as protons accelerated with a particle accelerator, onto a target tumor. These particles damage the DNA of cells, ultimately causing their death. Cancerous cells, because of their high rate of division and their reduced ability to repair damaged DNA, are particularly vulnerable to attack on their DNA.

Patents related to the current invention are summarized here.

Proton Beam Therapy System

F. Cole, et. al. of Loma Linda University Medical Center "Multi-Station Proton Beam Therapy System", U.S. Pat. No. 4,870,287 (Sep. 26, 1989) describe a proton beam therapy system for selectively generating and transporting proton beams from a single proton source and accelerator to a selected treatment room of a plurality of patient treatment rooms.

Imaging

Lomax, A., "Method for Evaluating Radiation Model Data in Particle Beam Radiation Applications", U.S. Pat. No. 8,461,559 B2 (Jun. 11, 2013) describes comparing a radiation target to a volume with a single pencil beam shot to the targeted volume.

P. Adamee, et. al. "Charged Particle Beam Apparatus and Method for Operating the Same", U.S. Pat. No. 7,274,018 (Sep. 25, 2007) and P. Adamee, et. al. "Charged Particle Beam Apparatus and Method for Operating the Same", U.S. Pat. No. 7,045,781 (May 16, 2006) describe a charged particle beam apparatus configured for serial and/or parallel imaging of an object.

K. Hiramoto, et. al. "Ion Beam Therapy System and its Couch Positioning System", U.S. Pat. No. 7,193,227 (Mar. 20, 2007) describe an ion beam therapy system having an X-ray imaging system moving in conjunction with a rotating gantry.

C. Maurer, et. al. "Apparatus and Method for Registration of Images to Physical Space Using a Weighted Combination of Points and Surfaces", U.S. Pat. No. 6,560,354 (May 6, 2003) described a process of X-ray computed tomography registered to physical measurements taken on the patient's body, where different body parts are given different weights. Weights are used in an iterative registration process to determine a rigid body transformation process, where the transformation function is used to assist surgical or stereotactic procedures.

M. Blair, et. al. "Proton Beam Digital Imaging System", U.S. Pat. No. 5,825,845 (Oct. 20, 1998) describe a proton beam digital imaging system having an X-ray source that is movable into a treatment beam line that can produce an X-ray beam through a region of the body. By comparison of the relative positions of the center of the beam in the patient orientation image and the isocentre in the master prescription image with respect to selected monuments, the amount and direction of movement of the patient to make the best beam center correspond to the target isocentre is determined.

S. Nishihara, et. al. "Therapeutic Apparatus", U.S. Pat. No. 5,039,867 (Aug. 13, 1991) describe a method and apparatus for positioning a therapeutic beam in which a first distance is determined on the basis of a first image, a second distance is determined on the basis of a second image, and the patient is moved to a therapy beam irradiation position on the basis of the first and second distances.

Problem

There exists in the art of charged particle cancer therapy a need for accurate, precise, and rapid imaging of a patient and/or treatment of a tumor using charged particles in a complex room setting.

SUMMARY OF THE INVENTION

The invention comprises a multi-axes/multi-probe type imaging apparatus and method of use thereof.

DESCRIPTION OF THE FIGURES

A more complete understanding of the present invention is derived by referring to the detailed description and claims when considered in connection with the Figures, wherein like reference numbers refer to similar items throughout the Figures.

FIG. 4A and FIG. 4B illustrate a top view of a beam control tray and a side view of the beam control tray, respectively.

FIG. 14A illustrates a scintillation material coupled to a detector array, FIG. 14B illustrates a fiber optic array in a tomography system; FIG. 14C and FIG. 14D illustrate end views of the fiber optic array; and FIG. 14E illustrates a micro-optic array coupled to the scintillation material;

FIG. 15 illustrates use of multiple layers of scintillation materials;

FIG. 17B illustrates detector arrays orthogonally coupled to the scintillation material; and FIG. 17C and FIG. 17D illustrate multiple detector arrays coupled to the scintillation material;

FIG. 20 illustrates a dynamic charged particle beam positioning system;

FIG. 21 illustrates a treatment beam depth of penetration tracking system;

Figure 1A:
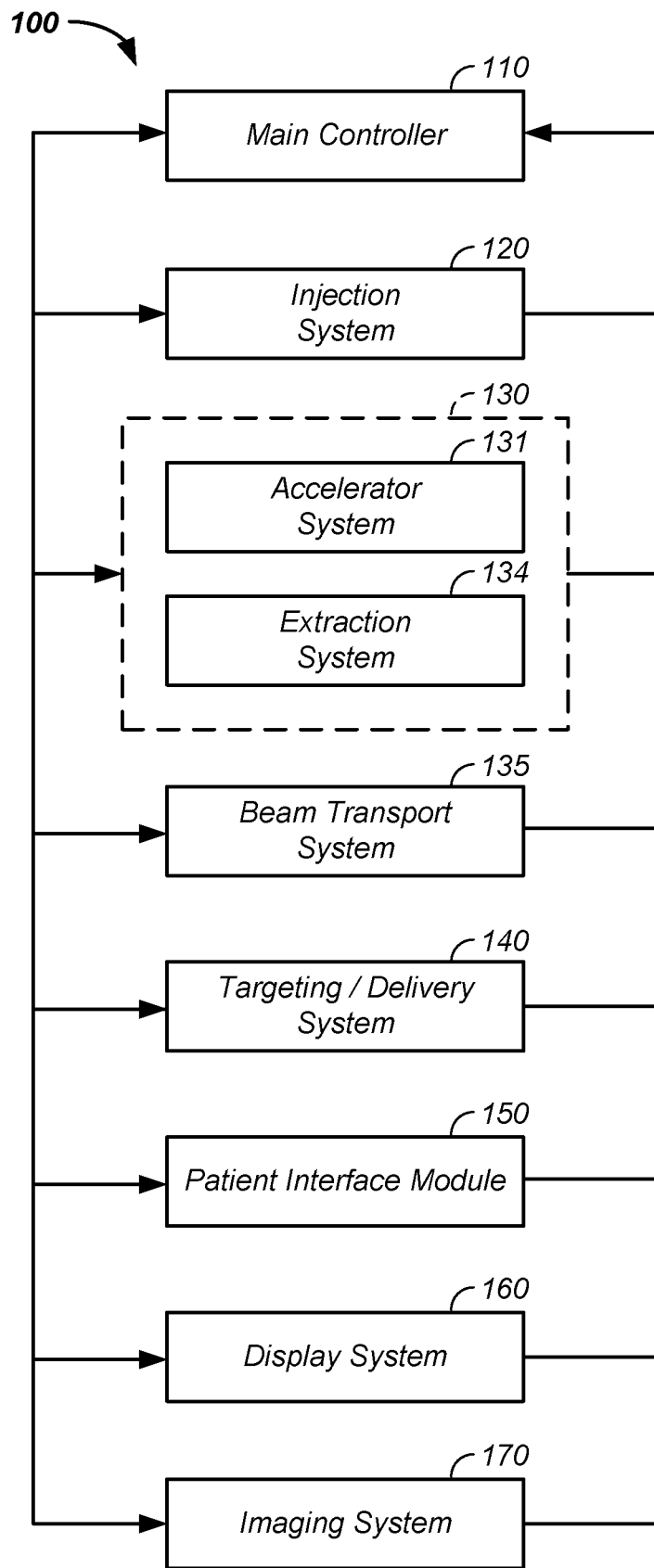
FIG. 1A and FIG. 1B illustrate component connections of a charged particle beam therapy system.

Elements and steps in the figures are illustrated for simplicity and clarity and have not necessarily been rendered according to any particular sequence. For example, steps that are performed concurrently or in different order are illustrated in the figures to help improve understanding of embodiments of the present invention.

DETAILED DESCRIPTION OF THE INVENTION

The invention comprises a method and apparatus for imaging a tumor with X-rays while, simultaneously or alternatingly, treating or imaging the tumor with positively charged particles.

In one embodiment, the X-ray imaging and charged particle beam treatment or imaging system comprising the steps of: rotating an X-ray imaging system, configured to deliver the X-rays, around both a first rotation axis and the patient; imaging the patient using X-rays from the X-ray imaging system; and passing the positively charged particles through an exit port of a nozzle system, the nozzle system connected to a synchrotron via a first beam transport line, the positively charged particles passing into the patient from the exit port along a z-axis and at least one of: (1) treating the tumor with the positively charged particles and (2) imaging the patient with residual charged particles comprising the positively charged particles after transmitting through the patient. In one case, a first cone beam X-ray source and a second cone beam X-ray source are positioned on a first side of the patient and at least one two-dimensional X-ray detector is positioned on an opposite side of the patient from the first cone beam X-ray source.

In combination a multiplexed proton tomography imaging apparatus and method of use thereof is used with the X-ray/proton beam imaging system. For example, a method for imaging a tumor of a patient comprises the steps of: (1) simultaneously detecting spatially resolved positively charged particle positions passing through each of a set of cross-section planes, where the cross-section planes are both prior to and posterior to the patient along a path of the positively charged particles; (2) determining a prior vector for each of the individual positively charged particles entering a patient using the detected positions; (3) determining a posterior vector for each of the individual positively charged particles exiting the patient using the detected positions; (4) generating a path, a best path, and/or a probable path of each positively charged particle through the patient; and (5) generating an image of the patient using the n probable proton paths. In one case, an imaging system: (1) delivers a set of n protons from a synchrotron: through a beam transport system exit nozzle, through a proton radial cross-section beam expander, through a first prior imaging sheet, through a second prior imaging sheet, through a patient position, through at least one posterior imaging sheet, and into a scintillation material of a beam energy scintillation detector system, where the first prior imaging sheet is positioned between the proton radial cross-section beam expander and the patient position, where the second prior imaging sheet is positioned between the proton radial cross-section beam expander and the patient position; (2) simultaneously detects spatially resolved both prior and posterior position photon emissions, resultant from passage of multiple protons; (4) determines both a prior vector and a posterior vector for each proton; and (5) determines a path for each proton through the patient and uses the determined paths, optionally and preferably with residual energy determinations, to generate an image of the patient.

In combination, a method of double exposure imaging of a tumor of a patient is performed using hardware, using a detector responsive to both X-rays and positively charged particles, simultaneously, and/or in either order. The preferably near-simultaneous double exposure yields enhanced resolution due to the imaging rate versus patient movement, no requirement of a software overlay step, and associated errors, of the X-ray based image and the positively charged particle based image, and enhancement of an X-ray image, the enhancement resultant from a differing physical interaction of the positively charged particles with the patient compared to interactions of X-rays and the patient. Further, resolution enhancements utilize individual particle tracking, as measured using detection screens, to determine a probable intra-patient path. Optionally, residual energy positively charged particles, having passed through a primarily X-ray detector, are used to generate a second/dual image at a secondary detector, such as a detector based on scintillation resultant from proton absorbance.

In combination, a method for imaging a tumor of a patient using X-rays and positively charged particles comprises the steps of: (1) generating an X-ray image using the X-rays directed from an X-ray source, through the patient, and to an X-ray detector, (2) generating a positively charged particle image: (a) using the positively charged particles directed from an exit nozzle, through the patient, through the X-ray detector, and to a scintillator, the scintillator emitting photons when struck by the positively charged particles and (b) generating the positively charged particle image of the tumor using a photon detector configured to detect the emitted photons, where the X-ray detector maintains a static position between said the nozzle and the scintillator during the step of generating a positively charged particle image. Individual images are optionally and preferably collected as a function of relative rotation of the patient and the imaging elements to form a three-dimensional image, such as via tomography.

In combination, a method and apparatus is described for determining a position of a tumor in a patient for treatment of the tumor using positively charged particles in a treatment room. More particularly, the method and apparatus use a set of fiducial markers and fiducial detectors to mark/determine relative position of static and/or moveable objects in a treatment room using photons passing from the markers to the detectors. Further, position and orientation of at least one of the objects is calibrated to a reference line, such as a zero-offset beam treatment line passing through an exit nozzle, which yields a relative position of each fiducially marked object in the treatment room. Treatment calculations are subsequently determined using the reference line and/or points thereon. The inventor notes that the treatment calculations are optionally and preferably performed without use of an isocenter point, such as a central point about which a treatment room gantry rotates, which eliminates mechanical errors associated with the isocenter point being an isocenter volume in practice.

For example, a set of fiducial marker detectors detect photons emitted from and/or reflected off of a set of fiducial markers positioned on one or more objects in a treatment room and resultant determined distances and/or calculated angles are used to determine relative positions of multiple objects or elements in the treatment room. Generally, in an iterative process, at a first time objects, such as a treatment beamline output nozzle, a specific portion of a patient relative to a tumor, a scintillation detection material, an X-ray system element, and/or a detection element, are mapped and relative positions and/or angles therebetween are determined. At a second time, the position of the mapped objects is used in: (1) imaging, such as X-ray, positron emission tomography, and/or proton beam imaging and/or (2) beam targeting and treatment, such as positively charged particle based cancer treatment. As relative positions of objects in the treatment room are dynamically determined using the fiducial marking system, engineering and/or mathematical constraints of a treatment beamline isocenter is removed.

In combination, a method and apparatus for imaging a tumor of a patient using positively charged particles, comprising the steps of: (1) sequentially delivering from an output nozzle, connected to a first beam transport line, to the patient: a first set of the positively charged particles comprising a first mean energy and a second set of the positively charged particles comprising a second mean energy, the second mean energy at least two mega electron Volts different from the first mean energy; (2) after transmission through the patient, sequentially detecting: a first residual energy of the first set of the positively charged particles and a second residual energy of the second set of the positively charged particles; and (3) determining a water equivalent thickness of a probed path of the patient using the first residual energy and the second residual energy. The detection step optionally uses a scintillation material and/or an X-ray detector material to detect the residual energy positively charged particles. Use of a half-maximum of a Gaussian fit to output of the detection material as a function of energy, preferably using three of more detected residual energies, yields a water equivalent thickness of the sampled beam path.

In combination, an apparatus and method of use thereof are used for directing positively charged particle beams into a patient from several directions. In one example, a charged particle delivery system, comprising: a controller, an accelerator, a beam path switching magnet, a primary beam line from the accelerator to the path switching magnet, and a plurality of physically separated beam transport lines from the beam path switching magnet to a single patient treatment position is used, where the controller and beam switching magnet are used to direct sets of the positively charged particles through alternatingly selected beam transport lines to the patient, tumor, and/or an imaging detector. Optionally, during a single session and at separate times, a single repositionable treatment nozzle is repositioned to interface with each beam transport line, such as to a terminus of each beam transport line, which allows the charged particle delivery system to use one and/or fewer beam output nozzles that are moved with nozzle gantries. A single nozzle with first and second axis scanning capability along with beam transport lines leading to various sides of a patient allow the charged particle delivery system to operate without movement and/or rotation of a beam transport gantry and an associated beam transport gantry. Beam transport line gantries are optional as one or more of the beam transport lines are preferably statically positioned.

In combination, a beam adjustment system is used to perform energy adjustments on circulating charged particles in a synchrotron previously accelerated to a starting energy with a traditional accelerator of the synchrotron or related devices, such as a cyclotron. The beam adjustment system uses a radio-frequency modulated potential difference applied along a longitudinal path of the circulating charged particles to accelerate or decelerate the circulating charged particles. Optionally, the beam adjustment system phase shifts the applied radio-frequency field to accelerate or decelerate the circulating charged particle while spatially longitudinally tightening a grouped bunch of the circulating charged particles. The beam adjustment system facilitates treating multiple layers or depths of the tumor between the slow step of reloading the synchrotron.

Optionally, the potential differences across a gap described herein are used to accelerate or decelerate the charged particle after extraction from the synchrotron without use of the radio-frequency modulation.

In combination, an imaging system, such as a positron emission tracking system, optionally used to control the beam adjustment system, is used to: dynamically determine a treatment beam position, track a history of treatment beam positions, guide the treatment beam, and/or image a tumor before, during, and/or after treatment with the charged particle beam.

In combination, an imaging system translating on a linear path past a patient operates alternatingly with and/or during a gantry rotating a treatment beam around the patient. More particularly, a method for both imaging a tumor and treating the tumor of a patient using positively charged particles includes the steps of: (1) rotating a gantry support and/or gantry, connected to at least a portion of a beam transport system configured to pass a charged particle treatment beam, circumferentially about the patient and a gantry rotation axis; (2) translating a translatable imaging system past the patient on a path parallel to an axis perpendicular to the gantry rotation axis; (3) imaging the tumor using the translatable imaging system; and (4) treating the tumor using the treatment beam.

In combination, a method for imaging and treating a tumor of a patient with positively charged particles, comprises the steps of: (1) using a rotatable gantry support to support and rotate a section of a positively charged particle beam transport line about a rotation axis and a tumor of a patient; (2) using a rotatable and optionally extendable secondary support to support, circumferentially position, and laterally position a primary and optional secondary imaging system about the tumor; (3) image the tumor using the primary and optional secondary imaging system as a function of rotation and/or translation of the secondary support; and (4) treat, optionally concurrently, the tumor using the positively charged particles as a function of circumferential position of the section of the charged particle beam about the tumor.

In combination, a method and apparatus for imaging a tumor of a patient using positively charged particles and X-rays, comprises the steps of: (1) transporting the positively charged particles from an accelerator to a patient position using a beam transport line, where the beam transport line comprises a positively charged particle beam path and an X-ray beam path; (2) detecting scintillation induced by the positively charged particles using a scintillation detector system; (3) detecting X-rays using an X-ray detector system; (4) positioning a mounting rail through linear extension/retraction to: at a first time and at a first extension position of the mounting rail, position the scintillation detector system opposite the patient position from the exit nozzle and at a second time and at a second extension position of the mounting rail, position the X-ray detector system opposite the patient position from the exit nozzle; (5) generating an image of the tumor using output of the scintillation detector system and the X-ray detector system; and (6) alternating between the step of detecting scintillation and treating the tumor via irradiation of the tumor using the positively charged particles.

In combination, a method or apparatus for tomographically imaging a sample, such as a tumor of a patient, using positively charged particles is described. Position, energy, and/or vectors of the positively charged particles are determined using a plurality of scintillators, such as layers of chemically distinct scintillators where each chemically distinct scintillator emits photons of differing wavelengths upon energy transfer from the positively charged particles. Knowledge of position of a given scintillator type and a color of the emitted photon from the scintillator type allows a determination of residual energy of the charged particle energy in a scintillator detector. Optionally, a two-dimensional detector array additionally yields x/y-plane information, coupled with the z-axis energy information, about state of the positively charged particles. State of the positively charged particles as a function of relative sample/particle beam rotation is used in tomographic reconstruction of an image of the sample or the tumor.

In another example, a method or apparatus for tomographic imaging of a tumor of a patient using positively charged particles respectively positions a plurality of two-dimensional detector arrays on multiple surfaces of a scintillation material or scintillator. For instance, a first two-dimensional detector array is optically coupled to a first side or surface of a scintillation material, a second two-dimensional detector array is optically coupled to a second side of the scintillation material, and a third two-dimensional detector array is optically coupled to a third side of the scintillation material. Secondary photons emitted from the scintillation material, resultant from energy transfer from the positively charged particles, are detected by the plurality of two-dimensional detector arrays, where each detector array images the scintillation material. Combining signals from the plurality of two-dimensional detector arrays, the path, position, energy, and/or state of the positively charged particle beam as a function of time and/or rotation of the patient relative to the positively charged particle beam is determined and used in tomographic reconstruction of an image of the tumor in the patient or a sample. Particularly, a probabilistic pathway of the positively charged particles through the sample, which is altered by sample constituents, is constrained, which yields a higher resolution, a more accurate and/or a more precise image.

In another example, a scintillation material is longitudinally packaged in a circumferentially surrounding sheath, where the sheath has a lower index of refraction than the scintillation material. The scintillation material yields emitted secondary photons upon passage of a charged particle beam, such as a positively charged residual particle beam having transmitted through a sample. The internally generated secondary photons within the sheath are guided to a detector element by the difference in index of refraction between the sheath and the scintillation material, similar to a light pipe or fiber optic. The coated scintillation material or fiber is referred to herein as a scintillation optic. Multiple scintillation optics are assembled to form a two-dimensional scintillation array. The scintillation array is optionally and preferably coupled to a detector or two-dimensional detector array, such as via a coupling optic, an array of focusing optics, and/or a color filter array.

In combination, an ion source is coupled to the apparatus. The ion source extraction system facilitates on demand extraction of charged particles at relatively low voltage levels and from a stable ion source. For example, a triode extraction system allows extraction of charged particles, such as protons, from a maintained temperature plasma source, which reduces emittance of the extracted particles and allows use of lower, more maintainable downstream potentials to control an ion beam path of the extracted ions. The reduced emittance facilitates ion beam precision in applications, such as in imaging, tumor imaging, tomographic imaging, and/or cancer treatment.

In combination, a state of a charged particle beam is monitored and/or checked, such as against a previously established radiation plan, in a position just prior to the beam entering the patient. In one example, the charged particle beam state is measured after a final manipulation of intensity, energy, shape, and/or position, such as via use of an insert, a range filter, a collimator, an aperture, and/or a compensator. In one case, one or more beam crossing elements, sheets, coatings, or layers, configured to emit photons upon passage therethrough by the charged particle beam, are positioned between the final manipulation apparatus, such as the insert, and prior to entry into the patient.

In combination, a patient specific tray insert is inserted into a tray frame to form a beam control tray assembly, the beam control tray assembly is inserted into a slot of a tray receiver assembly, and the tray assembly is positioned relative to a gantry nozzle. Optionally, multiple tray inserts, each used to control a beam state parameter, are inserted into slots of the tray receiver assembly. The beam control tray assembling includes an identifier, such as an electromechanical identifier, of the particular insert type, which is communicated to a main controller, such as via the tray receiver assembly. Optionally and preferably, a hand control pendant is used in loading and/or positioning the tray receiver assembly.

In combination, a gantry positions both: (1) a section of a beam transport system, such as a terminal section, used to transport and direct positively charged particles to a tumor and (2) at least one imaging system. In one case, the imaging system is orientated on a same axis as the positively charged particle, such as at a different time through rotation of the gantry. In another case, the imaging system uses at least two crossing beamlines, each beamline coupled to a respective detector, to yield multiple views of the patient. In another case, one or more imaging subsystem yields a two-dimensional image of the patient, such as for position confirmation and/or as part of a set of images used to develop a three-dimensional image of the patient.

In combination, multiple linked control stations are used to control position of elements of a beam transport system, nozzle, and/or patient specific beam shaping element relative to a dynamically controlled patient position and/or an imaging surface, element, or system.

In combination, a tomography system is optionally used in combination with a charged particle cancer therapy system. The tomography system uses tomography or tomographic imaging, which refers to imaging by sections or sectioning through the use of a penetrating wave, such as a positively charge particle from an injector and/or accelerator. Optionally and preferably, a common injector, accelerator, and beam transport system is used for both charged particle based tomographic imaging and charged particle cancer therapy. In one case, an output nozzle of the beam transport system is positioned with a gantry system while the gantry system and/or a patient support maintains a scintillation plate of the tomography system on the opposite side of the patient from the output nozzle.

In another example, a charged particle state determination system, of a cancer therapy system or tomographic imaging system, uses one or more coated layers in conjunction with a scintillation material, scintillation detector and/or a tomographic imaging system at time of tumor and surrounding tissue sample mapping and/or at time of tumor treatment, such as to determine an input vector of the charged particle beam into a patient and/or an output vector of the charged particle beam from the patient.

In another example, the charged particle tomography apparatus is used in combination with a charged particle cancer therapy system. For example, tomographic imaging of a cancerous tumor is performed using charged particles generated with an injector, accelerator, and guided with a delivery system. The cancer therapy system uses the same injector, accelerator, and guided delivery system in delivering charged particles to the cancerous tumor. For example, the tomography apparatus and cancer therapy system use a common raster beam method and apparatus for treatment of solid cancers. More particularly, the invention comprises a multi-axis and/or multi-field raster beam charged particle accelerator used in: (1) tomography and (2) cancer therapy. Optionally, the system independently controls patient translation position, patient rotation position, two-dimensional beam trajectory, delivered radiation beam energy, delivered radiation beam intensity, beam velocity, timing of charged particle delivery, and/or distribution of radiation striking healthy tissue. The system operates in conjunction with a negative ion beam source, synchrotron, patient positioning, imaging, and/or targeting method and apparatus to deliver an effective and uniform dose of radiation to a tumor while distributing radiation striking healthy tissue.

In combination, a treatment delivery control system (TDCS) or main controller is used to control multiple aspects of the cancer therapy system, including one or more of: an imaging system, such as a CT or PET; a positioner, such as a couch or patient interface module; an injector or injection system; a radio-frequency quadrupole system; a ring accelerator or synchrotron; an extraction system; an irradiation plan; and a display system. The TDCS is preferably a control system for automated cancer therapy once the patient is positioned. The TDCS integrates output of one or more of the below described cancer therapy system elements with inputs of one or more of the below described cancer therapy system elements. More generally, the TDCS controls or manages input and/or output of imaging, an irradiation plan, and charged particle delivery.

In combination, one or more trays are inserted into the positively charged particle beam path, such as at or near the exit port of a gantry nozzle in close proximity to the patient. Each tray holds an insert, such as a patient specific insert for controlling the energy, focus depth, and/or shape of the charged particle beam. Examples of inserts include a range shifter, a compensator, an aperture, a ridge filter, and a blank. Optionally and preferably, each tray communicates a held and positioned insert to a main controller of the charged particle cancer therapy system. The trays optionally hold one or more of the imaging sheets configured to emit light upon transmission of the charged particle beam through a corresponding localized position of the one or more imaging sheets.

For clarity of presentation and without loss of generality, throughout this document, treatment systems and imaging systems are described relative to a tumor of a patient. However, more generally any sample is imaged with any of the imaging systems described herein and/or any element of the sample is treated with the positively charged particle beam(s) described herein.

Charged Particle Beam Therapy

Throughout this document, a charged particle beam therapy system, such as a proton beam, hydrogen ion beam, or carbon ion beam, is described. Herein, the charged particle beam therapy system is described using a proton beam. However, the aspects taught and described in terms of a proton beam are not intended to be limiting to that of a proton beam and are illustrative of a charged particle beam system, a positively charged beam system, and/or a multiply charged particle beam system, such as $C^{4+}$ or $C^{6+}$. Any of the techniques described herein are equally applicable to any charged particle beam system.

Referring now to FIG. 1A, a charged particle beam system 100 is illustrated. The charged particle beam preferably comprises a number of subsystems including any of: a main controller 110; an injection system 120; a synchrotron 130 that typically includes: (1) an accelerator system 131 and (2) an internal or connected extraction system 134; a beam transport system 135; a scanning/targeting/delivery system 140; a nozzle system 146; a patient interface module 150; a display system 160; and/or an imaging system 170.

An exemplary method of use of the charged particle beam system 100 is provided. The main controller 110 controls one or more of the subsystems to accurately and precisely deliver protons to a tumor of a patient. For example, the main controller 110 obtains an image, such as a portion of a body and/or of a tumor, from the imaging system 170. The main controller 110 also obtains position and/or timing information from the patient interface module 150. The main controller 110 optionally controls the injection system 120 to inject a proton into a synchrotron 130. The synchrotron typically contains at least an accelerator system 131 and an extraction system 134. The main controller 110 preferably controls the proton beam within the accelerator system, such as by controlling speed, trajectory, and timing of the proton beam. The main controller then controls extraction of a proton beam from the accelerator through the extraction system 134. For example, the controller controls timing, energy, and/or intensity of the extracted beam. The controller 110 also preferably controls targeting of the proton beam through the scanning/targeting/delivery system 140 to the patient interface module 150. One or more components of the patient interface module 150, such as translational and rotational position of the patient, are preferably controlled by the main controller 110. Further, display elements of the display system 160 are preferably controlled via the main controller 110. Displays, such as display screens, are typically provided to one or more operators and/or to one or more patients. In one embodiment, the main controller 110 times the delivery of the proton beam from all systems, such that protons are delivered in an optimal therapeutic manner to the tumor of the patient.

Herein, the main controller 110 refers to a single system controlling the charged particle beam system 100, to a single controller controlling a plurality of subsystems controlling the charged particle beam system 100, or to a plurality of individual controllers controlling one or more sub-systems of the charged particle beam system 100.

Example I

Charged Particle Cancer Therapy System Control

Figure 1B:
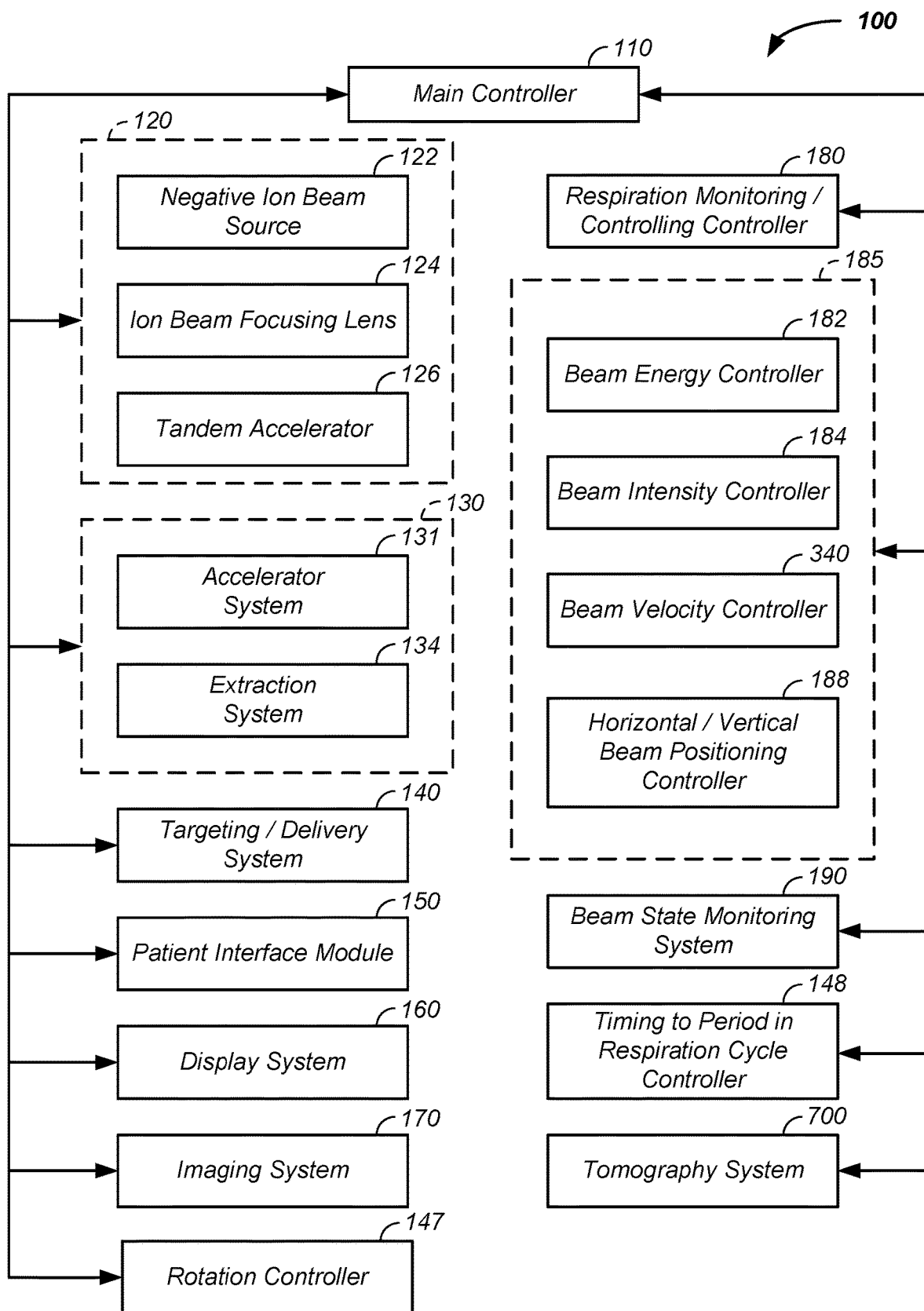

Referring now to FIG. 1B, an example of a charged particle cancer therapy system 100 is provided. A main controller receives input from one, two, three, or four of a respiration monitoring and/or controlling controller 180, a beam controller 185, a rotation controller 147, and/or a timing to a time period in a respiration cycle controller 148. The beam controller 185 preferably includes one or more or a beam energy controller 182, the beam intensity controller 340, a beam velocity controller 186, and/or a horizontal/vertical beam positioning controller 188. The main controller 110 controls any element of the injection system 120; the synchrotron 130; the scanning/targeting/delivery system 140; the patient interface module 150; the display system 160; and/or the imaging system 170. For example, the respiration monitoring/controlling controller 180 controls any element or method associated with the respiration of the patient; the beam controller 185 controls any of the elements controlling acceleration and/or extraction of the charged particle beam; the rotation controller 147 controls any element associated with rotation of the patient 830 or gantry; and the timing to a period in respiration cycle controller 148 controls any aspects affecting delivery time of the charged particle beam to the patient. As a further example, the beam controller 185 optionally controls any magnetic and/or electric field about any magnet in the charged particle cancer therapy system 100. One or more beam state sensors 190 sense position, direction, intensity, and/or energy of the charged particles at one or more positions in the charged particle beam path. A tomography system 700, described infra, is optionally used to monitor intensity and/or position of the charged particle beam.

Figure 1C:
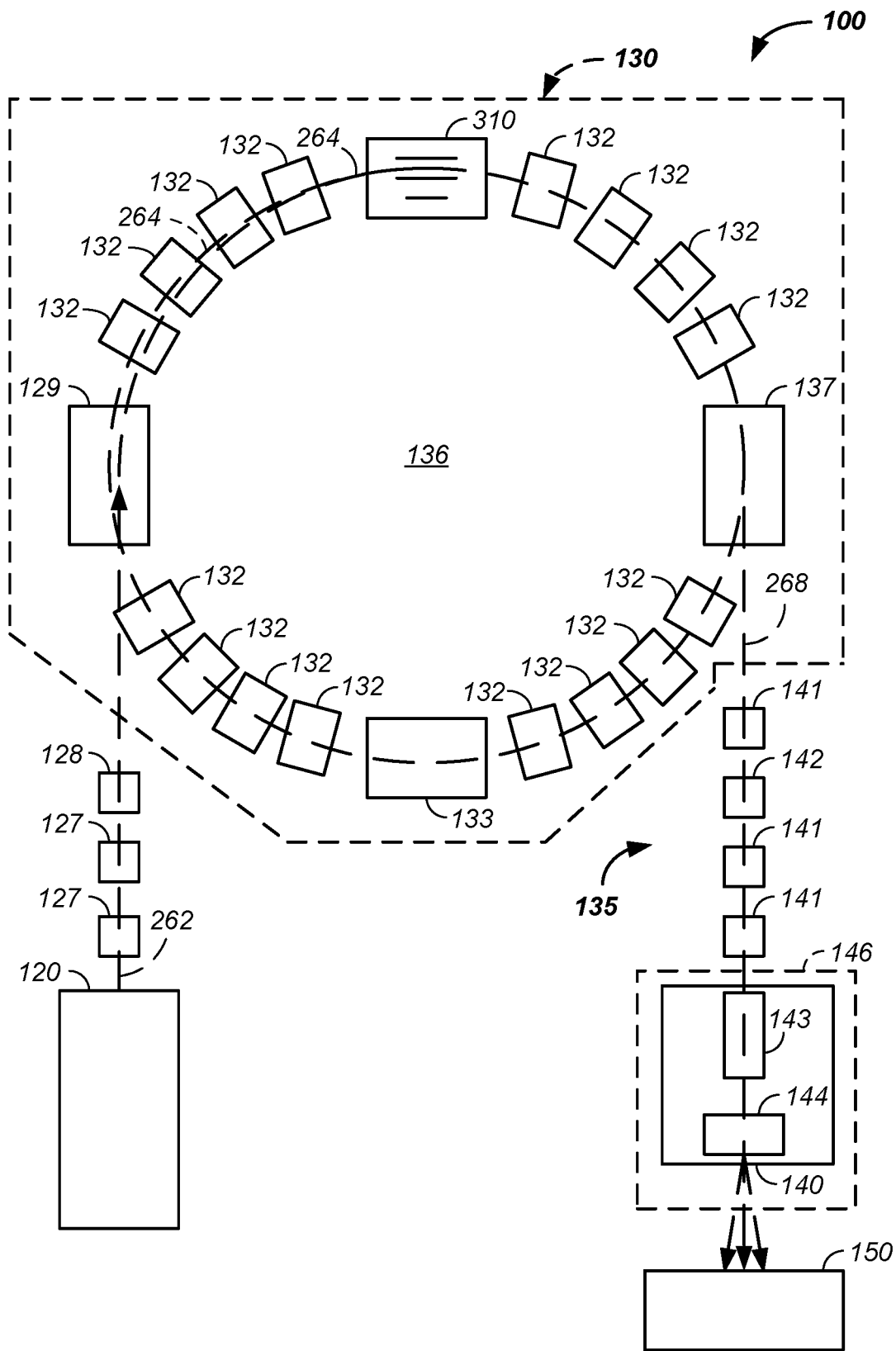
FIG. 1C illustrates a charged particle therapy system.

Referring now to FIG. 1C, an illustrative exemplary embodiment of one version of the charged particle beam system 100 is provided. The number, position, and described type of components is illustrative and non-limiting in nature. In the illustrated embodiment, the injection system 120 or ion source or charged particle beam source generates protons. The injection system 120 optionally includes one or more of: a negative ion beam source, an ion beam focusing lens, and a tandem accelerator. The protons are delivered into a vacuum tube that runs into, through, and out of the synchrotron. The generated protons are delivered along an initial path 262. Optionally, focusing magnets 127, such as quadrupole magnets or injection quadrupole magnets, are used to focus the proton beam path. A quadrupole magnet is a focusing magnet. An injector bending magnet 128 bends the proton beam toward a plane of the synchrotron 130. The focused protons having an initial energy are introduced into an injector magnet 129, which is preferably an injection Lambertson magnet. Typically, the initial beam path 262 is along an axis off of, such as above, a circulating plane of the synchrotron 130. The injector bending magnet 128 and injector magnet 129 combine to move the protons into the synchrotron 130. Main bending magnets, dipole magnets, turning magnets, or circulating magnets 132 are used to turn the protons along a circulating beam path 264. A dipole magnet is a bending magnet. The main bending magnets 132 bend the initial beam path 262 into a circulating beam path 264. In this example, the main bending magnets 132 or circulating magnets are represented as four sets of four magnets to maintain the circulating beam path 264 into a stable circulating beam path. However, any number of magnets or sets of magnets are optionally used to move the protons around a single orbit in the circulation process. The protons pass through an accelerator 133. The accelerator accelerates the protons in the circulating beam path 264. As the protons are accelerated, the fields applied by the magnets are increased. Particularly, the speed of the protons achieved by the accelerator 133 are synchronized with magnetic fields of the main bending magnets 132 or circulating magnets to maintain stable circulation of the protons about a central point or region 136 of the synchrotron. At separate points in time the accelerator 133/main bending magnet 132 combination is used to accelerate and/or decelerate the circulating protons while maintaining the protons in the circulating path or orbit. An extraction element of an inflector/deflector system is used in combination with a Lambertson extraction magnet 137 to remove protons from their circulating beam path 264 within the synchrotron 130. One example of a deflector component is a Lambertson magnet. Typically the deflector moves the protons from the circulating plane to an axis off of the circulating plane, such as above the circulating plane. Extracted protons are preferably directed and/or focused using an extraction bending magnet 142 and optional extraction focusing magnets 141, such as quadrupole magnets, and optional bending magnets along a positively charged particle beam transport path 268 in a beam transport system 135, such as a beam path or proton beam path, into the scanning/targeting/delivery system 140. Two components of a scanning system 140 or targeting system typically include a first axis control 143, such as a vertical control, and a second axis control 144, such as a horizontal control. In one embodiment, the first axis control 143 allows for about 100 mm of vertical or y-axis scanning of the proton beam 268 and the second axis control 144 allows for about 700 mm of horizontal or x-axis scanning of the proton beam 268. A nozzle system 146 is used for directing the proton beam, for imaging the proton beam, for defining shape of the proton beam, and/or as a vacuum barrier between the low pressure beam path of the synchrotron and the atmosphere. Protons are delivered with control to the patient interface module 150 and to a tumor of a patient. All of the above listed elements are optional and may be used in various permutations and combinations.

Ion Extraction from Ion Source

A method and apparatus are described for extraction of ions from an ion source.

For clarity of presentation and without loss of generality, examples focus on extraction of protons from the ion source. However, more generally cations of any charge are optionally extracted from a corresponding ion source with the techniques described herein. For instance, $C^{4+}$ or $C^{6+}$ are optionally extracted using the ion extraction methods and apparatus described herein. Further, by reversing polarity of the system, anions are optionally extracted from an anion source, where the anion is of any charge.

Herein, for clarity of presentation and without loss of generality, ion extraction is coupled with tumor treatment and/or tumor imaging. However, the ion extraction is optional used in any method or apparatus using a stream or time discrete bunches of ions.

Diode Extraction

Figure 2A:
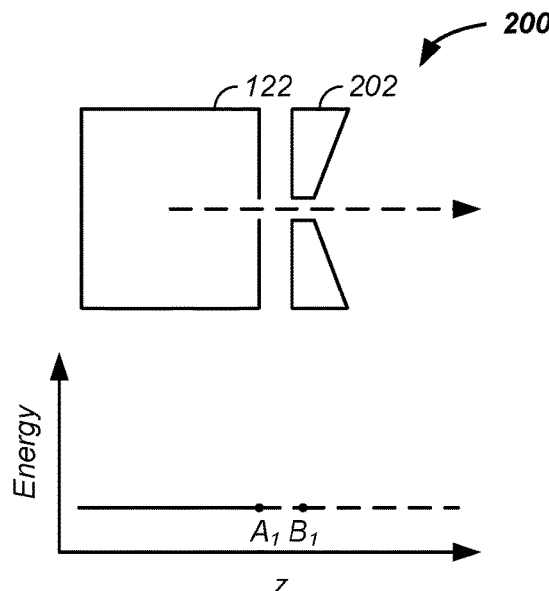
FIG. 2A and FIG. 2B illustrate a diode extraction system in standby and functional mode.
Figure 2C:
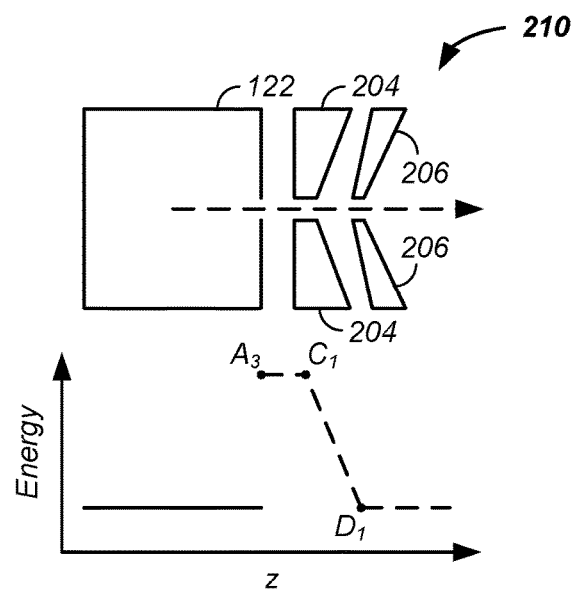
FIG. 2C and FIG. 2D illustrate a triode in standby and operational mode, respectively.
Figure 2B:
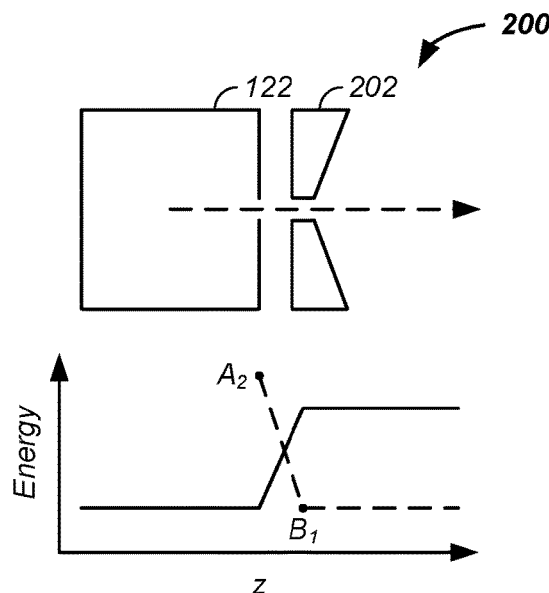

Referring now to FIG. 2A and FIG. 2B, a first ion extraction system is illustrated. The first ion extraction system uses a diode extraction system 200, where a first element of the diode extraction system is an ion source 122 or first electrode at a first potential and a second element 202 of the diode extraction system is at a second potential. Generally, the first potential is raised or lowered relative to the second potential to extract ions from the ion source 122 along the z-axis or the second potential is raised or lowered relative to the first potential to extract ions from the ion source 122 along the z-axis, where polarity of the potential difference determines if anions or cations are extracted from the ion source 122.

Still referring to FIG. 2A and FIG. 2B, an example of ion extraction from the ion source 122 is described. As illustrated in FIG. 2A, in a non-extraction time period, a non-extraction diode potential, $A_1$, of the ion source 122 is held at a potential equal to a potential, $B_1$, of the second element 202. Referring now to FIG. 2B, during an extraction time period, a diode extraction potential, $A_2$, of the ion source 122 is raised, causing a positively charged cation, such as the proton, to be drawn out of the ion chamber toward the lower potential of the second element 202. Similarly, if the diode extraction potential, $A_2$, of the ion source is lowered relative a potential, $B_1$, then an anion is extracted from the ion source 122 toward a higher potential of the second element 202. In the diode extraction system 200, the voltage of a large mass and corresponding large capacitance of the ion source 122 is raised or lowered, which takes time, has an RC time constant, and results in a range of temperatures of the plasma during the extraction time period, which is typically pulsed on and off with time. Particularly, as the potential of the ion source 122 is cycled with time, the ion source 122 temperature cycles, which results in a range of emittance values, resultant from conservation of momentum, and a corresponding less precise extraction beam. Alternatively, potential of the second element 202 is varied, altered, pulsed, or cycled, which reduces a range of emittance values during the extraction process.

Triode Extraction

Figure 2D:
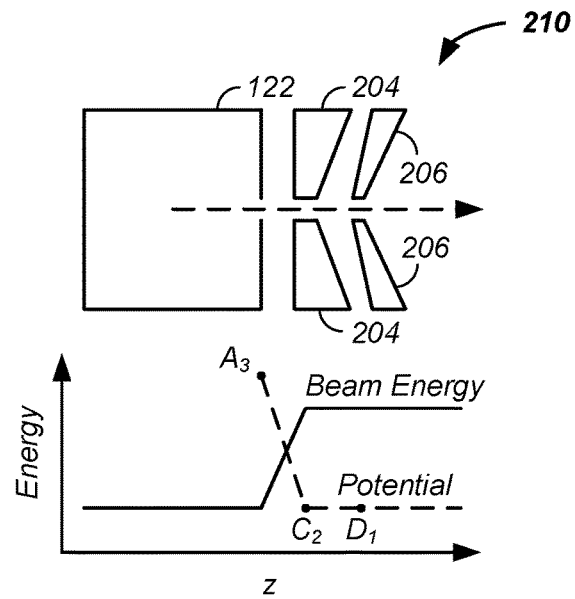

Referring now to FIG. 2C and FIG. 2D, a second ion extraction system is illustrated. The second ion extraction system uses a triode extraction system 210. The triode extraction system 210 uses: (1) an ion source 122, (2) a gating electrode 204 also referred to as a suppression electrode, and (3) an extraction electrode 206. Optionally, a first electrode of the triode extraction system 210 is positioned proximate the ion source 122 and is maintained at a potential as described, infra, using the ion source as the first electrode of the triode extraction system. Generally, potential of the gating electrode 204 is raised and lowered to, as illustrated, stop and start extraction of a positive ion. Varying the potential of the gating electrode 204 has the advantages of altering the potential of a small mass with a correspondingly small capacitance and small RC time constant, which via conservation of momentum, reduces emittance of the extracted ions. Optionally, a first electrode maintained at the first potential of the ion source is used as the first element of the triode extraction system in place of the ion source 122 while also optionally further accelerating and/or focusing the extracted ions or set of ions using the extraction electrode 206. Several example further describe the triode extraction system 210.

Example I

Still referring to FIG. 2C and FIG. 2D, a first example of ion beam extraction using the triode extraction system 210 is provided. Optionally and preferably, the ion source 122 is maintained at a stable temperature. Maintaining the ion source 122 at a stable temperature, such as with a constant applied voltage, results in ions with more uniform energy and thus velocity. Hence, extraction of ions from the stable temperature plasma results in extracted ions with more uniform energy or velocity and smaller emittance, where emittance is a property of a charged particle beam in a particle accelerator. Emittance is a measure for the average spread of particle coordinates in position-and-momentum phase space and has the dimension of length, such as meters, or length times angle, such as meters times radians.

Example II

Still referring to FIG. 2C and FIG. 2D, a second example of ion beam extraction using the triode extraction system 210 is provided illustrating voltages of the triode elements for extraction of cations, such as protons. Optionally and preferably, the extraction electrode 206 is grounded at zero volts or is near ground, which allows downstream elements about an ion beam path of the extracted ions to be held at ground or near ground. The ability to maintain downstream elements about the beam path at ground greatly eases design as the downstream elements are often of high mass with high capacitance, thus requiring large power supplies to maintain at positive or negative potentials. The ion source 122, for proton ion formation and extraction therefrom, is optionally maintained at 10 to 100 kV, more preferably at 20 to 80 kV, and most preferably at 30 kV ±less than 1, 5, or 10 kV. The gating electrode 204 is maintained at a non-extraction potential at or above the potential of the ion source 122 and is maintained at an extraction potential of less than the potential of the ion source and/or greater than or equal to the potential of the extraction electrode 206.

Example III

Still referring to FIG. 2C and FIG. 2D, a third example of anion beam extraction using the triode extraction system 210 is provided. Generally, for extraction of anions the potentials of the second example are inverted and/or multiplied by negative one. For instance, if the extraction electrode 206 is held at ground, then the ion source 122 is maintained with a negative voltage, such as at −30 kV, and the gating electrode cycles between the voltage of the ion source 122 and the potential of the extraction electrode 206 to turn off and on extraction of anions from the ion source 122 along the extraction beamline.

Example IV

Still referring to FIG. 2C and FIG. 2D, a fourth example of extraction suppression is provided. As illustrated in FIG. 2C, in the non-extraction mode the ion source potential, $A_3$, is equal to the gating electrode potential, $C_1$. However, the gating electrode 204, which is also referred to as a suppression electrode, is optionally held at a higher potential than the ion source potential so as to provide a suppression barrier or a potential resistance barrier keeping cations in the ion source 122. For instance, for cation extraction, if the ion source potential is +30 kV, then the gating electrode potential is greater than +30 kV, such as +32 kV±1, 1.5, or 2 kV. In a case of the ion source 122 forming anions, the gating electrode potential, $C_1$, is optionally held at a lower potential than the ion source potential, $A_3$. Generally, during the non-extraction phase, the gating electrode 204 is optionally maintained at a gating potential close to the ion source potential with a bias in voltage relative to the ion source potential repelling ions back into the ion source 122.

Example V

Still referring to FIG. 2C and FIG. 2D, a fifth example of using the triode extraction system 210 with varying types of ion sources is provided. The triode extraction system 210 is optionally used with an electron cyclotron resonance (ECR) ion source, a dual plasmatron ion source, an indirectly heated cathode ion source, a Freeman type ion source, or a Bernas type ion source.

Example VI

Herein, for clarity of presentation and without loss of generality, the triode extraction system 210 is integrated with an electron cyclotron resonance source. Generally, the electron resonance source generates an ionized plasma by heating or superimposing a static magnetic field and a high-frequency electromagnetic field at an electron cyclotron resonance frequency, which functions to form a localized plasma, where the heating power is optionally varied to yield differing initial energy levels of the ions. As the electron resonance source: (1) moves ions in an arc in a given direction and (2) is tunable in temperature, described infra, emittance of the electron resonance source is low and has an initial beam in a same mean cycling or arc following direction. The temperature of the electron cyclotron resonance ion source is optionally controlled through an external input, such as a tunable or adjustable microwave power, a controllable and variable gas pressure, and/or a controllable and alterable arc voltage. The external input allows the plasma density in the electron cyclotron resonance source to be controlled.

In a sixth example, an electron resonance source is the ion source 122 of the triode extraction system 210. Optionally and preferably, the gating electrode 204 of the triode extraction system is oscillated, such as from about the ion source potential toward the extraction electrode potential, which is preferably grounded. In this manner, the extracted electron beam along the initial path 262 is bunches of ions that have peak intensities alternating with low or zero intensities, such as in an AC wave as opposed to a continuous beam, such as a DC wave.

Example VII

Still referring to FIG. 2C and FIG. 2D, optionally and preferably geometries of the gating electrode 204 and/or the extraction electrode 206 are used to focus the extracted ions along the initial ion beam path 262.

Example VIII

Still referring to FIG. 2C and FIG. 2D, the lower emittance of the electron cyclotron resonance triode extraction system is optionally and preferably coupled with a downbeam or downstream radio-frequency quadrupole, used to focus the beam, and/or a synchrotron, used to accelerate the beam.

Example IX

Still referring to FIG. 2C and FIG. 2D, the lower emittance of the electron cyclotron resonance triode extraction system is maintained through the synchrotron 130 and to the tumor of the patient resulting in a more accurate, precise, smaller, and/or tighter treatment voxel of the charged particle beam or charged particle pulse striking the tumor.

Example X

Still referring to FIG. 2C and FIG. 2D, the lower emittance of the electron cyclotron resonance triode extraction system reduces total beam spread through the synchrotron 130 and the tumor to one or more imaging elements, such as an optical imaging sheet or scintillation material emitting photons upon passage of the charged particle beam or striking of the charged particle beam, respectively. The lower emittance of the charged particle beam, optionally and preferably maintained through the accelerator system 134 and beam transport system yields a tighter, more accurate, more precise, and/or smaller particle beam or particle burst diameter at the imaging surfaces and/or imaging elements, which facilitates more accurate and precise tumor imaging, such as for subsequent tumor treatment or to adjust, while the patient waits in a treatment position, the charged particle treatment beam position.

Any feature or features of any of the above provided examples are optionally and preferably combined with any feature described in other examples provided, supra, or herein.

Ion Extraction from Accelerator

Figure 3:
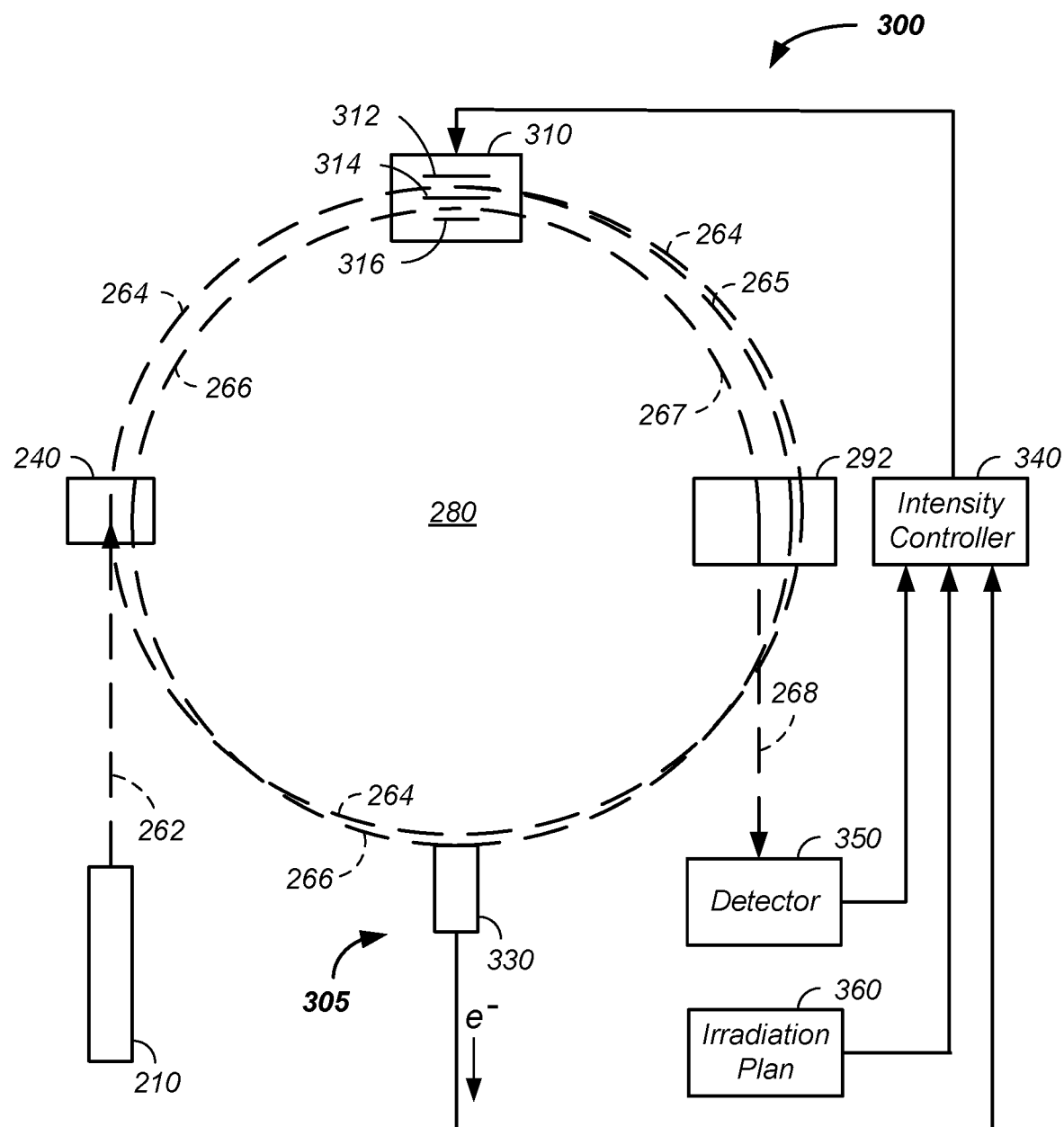
FIG. 3 illustrates a method of multi-axis charged particle beam irradiation control.

Referring now to FIG. 3, both: (1) an exemplary proton beam extraction system 300 from the synchrotron 130 and (2) a charged particle beam intensity control system 305 are illustrated. For clarity, FIG. 3 removes elements represented in FIG. 1C, such as the turning magnets, which allows for greater clarity of presentation of the proton beam path as a function of time. Generally, protons are extracted from the synchrotron 130 by slowing the protons. As described, supra, the protons were initially accelerated in a circulating path, which is maintained with a plurality of main bending magnets 132. The circulating path is referred to herein as an original central beamline 264. The protons repeatedly cycle around a central point in the synchrotron 136. The proton path traverses through a radio frequency (RF) cavity system 310. To initiate extraction, an RF field is applied across a first blade 312 and a second blade 314, in the RF cavity system 310. The first blade 312 and second blade 314 are referred to herein as a first pair of blades.

In the proton extraction process, an RF voltage is applied across the first pair of blades, where the first blade 312 of the first pair of blades is on one side of the circulating proton beam path 264 and the second blade 314 of the first pair of blades is on an opposite side of the circulating proton beam path 264. The applied RF field applies energy to the circulating charged-particle beam. The applied RF field alters the orbiting or circulating beam path slightly of the protons from the original central beamline 264 to an altered circulating beam path 265.

Upon a second pass of the protons through the RF cavity system, the RF field further moves the protons off of the original proton beamline 264. For example, if the original beamline is considered as a circular path, then the altered beamline is slightly elliptical. The frequency of the applied RF field is timed to apply outward or inward movement to a given band of protons circulating in the synchrotron accelerator. Orbits of the protons are slightly more off axis compared to the original circulating beam path 264. Successive passes of the protons through the RF cavity system are forced further and further from the original central beamline 264 by altering the direction and/or intensity of the RF field with each successive pass of the proton beam through the RF field. Timing of application of the RF field and/or frequency of the RF field is related to the circulating charged particles circulation pathlength in the synchrotron 130 and the velocity of the charged particles so that the applied RF field has a period, with a peak-to-peak time period, equal to a period of time of beam circulation in the synchrotron 130 about the center 136 or an integer multiple of the time period of beam circulation about the center 136 of the synchrotron 130. Alternatively, the time period of beam circulation about the center 136 of the synchrotron 130 is an integer multiple of the RF period time. The RF period is optionally used to calculated the velocity of the charged particles, which relates directly to the energy of the circulating charged particles.

The RF voltage is frequency modulated at a frequency about equal to the period of one proton cycling around the synchrotron for one revolution or at a frequency than is an integral multiplier of the period of one proton cycling about the synchrotron. The applied RF frequency modulated voltage excites a betatron oscillation. For example, the oscillation is a sine wave motion of the protons. The process of timing the RF field to a given proton beam within the RF cavity system is repeated thousands of times with each successive pass of the protons being moved approximately one micrometer further off of the original central beamline 264. For clarity, the approximately 1000 changing beam paths with each successive path of a given band of protons through the RF field are illustrated as the altered beam path 265. The RF time period is process is known, thus energy of the charged particles at time of hitting the extraction material or material 330, described infra, is known.

With a sufficient sine wave betatron amplitude, the altered circulating beam path 265 touches and/or traverses a material 330, such as a foil or a sheet of foil. The foil is preferably a lightweight material, such as beryllium, a lithium hydride, a carbon sheet, or a material having low nuclear charge components. Herein, a material of low nuclear charge is a material composed of atoms consisting essentially of atoms having six or fewer protons. The foil is preferably about 10 to 150 microns thick, is more preferably about 30 to 100 microns thick, and is still more preferably about 40 to 60 microns thick. In one example, the foil is beryllium with a thickness of about 50 microns. When the protons traverse through the foil, energy of the protons is lost and the speed of the protons is reduced. Typically, a current is also generated, described infra. Protons moving at the slower speed travel in the synchrotron with a reduced radius of curvature 266 compared to either the original central beamline 264 or the altered circulating path 265. The reduced radius of curvature 266 path is also referred to herein as a path having a smaller diameter of trajectory or a path having protons with reduced energy. The reduced radius of curvature 266 is typically about two millimeters less than a radius of curvature of the last pass of the protons along the altered proton beam path 265.

The thickness of the material 330 is optionally adjusted to create a change in the radius of curvature, such as about ½, 1, 2, 3, or 4 mm less than the last pass of the protons 265 or original radius of curvature 264. The reduction in velocity of the charged particles transmitting through the material 330 is calculable, such as by using the pathlength of the betatron oscillating charged particle beam through the material 330 and/or using the density of the material 330. Protons moving with the smaller radius of curvature travel between a second pair of blades. In one case, the second pair of blades is physically distinct and/or is separated from the first pair of blades. In a second case, one of the first pair of blades is also a member of the second pair of blades. For example, the second pair of blades is the second blade 314 and a third blade 316 in the RF cavity system 310. A high voltage DC signal, such as about 1 to 5 kV, is then applied across the second pair of blades, which directs the protons out of the synchrotron through an extraction magnet 137, such as a Lambertson extraction magnet, into a transport path 268.

Control of acceleration of the charged particle beam path in the synchrotron with the accelerator and/or applied fields of the turning magnets in combination with the above described extraction system allows for control of the intensity of the extracted proton beam, where intensity is a proton flux per unit time or the number of protons extracted as a function of time. For example, when a current is measured beyond a threshold, the RF field modulation in the RF cavity system is terminated or reinitiated to establish a subsequent cycle of proton beam extraction. This process is repeated to yield many cycles of proton beam extraction from the synchrotron accelerator.

In another embodiment, instead of moving the charged particles to the material 330, the material 330 is mechanically moved to the circulating charged particles. Particularly, the material 330 is mechanically or electromechanically translated into the path of the circulating charged particles to induce the extraction process, described supra. In this case, the velocity or energy of the circulating charged particle beam is calculable using the pathlength of the beam path about the center 136 of the synchrotron 130 and from the force applied by the bending magnets 132.

In either case, because the extraction system does not depend on any change in magnetic field properties, it allows the synchrotron to continue to operate in acceleration or deceleration mode during the extraction process. Stated differently, the extraction process does not interfere with synchrotron acceleration. In stark contrast, traditional extraction systems introduce a new magnetic field, such as via a hexapole, during the extraction process. More particularly, traditional synchrotrons have a magnet, such as a hexapole magnet, that is off during an acceleration stage. During the extraction phase, the hexapole magnetic field is introduced to the circulating path of the synchrotron. The introduction of the magnetic field necessitates two distinct modes, an acceleration mode and an extraction mode, which are mutually exclusive in time. The herein described system allows for acceleration and/or deceleration of the proton during the extraction step and tumor treatment without the use of a newly introduced magnetic field, such as by a hexapole magnet.

Charged Particle Beam Intensity Control

Control of applied field, such as a radio-frequency (RF) field, frequency and magnitude in the RF cavity system 310 allows for intensity control of the extracted proton beam, where intensity is extracted proton flux per unit time or the number of protons extracted as a function of time.

Still referring FIG. 3, the intensity control system 305 is further described. In this example, an intensity control feedback loop is added to the extraction system, described supra. When protons in the proton beam hit the material 330 electrons are given off from the material 330 resulting in a current. The resulting current is converted to a voltage and is used as part of an ion beam intensity monitoring system or as part of an ion beam feedback loop for controlling beam intensity. The voltage is optionally measured and sent to the main controller 110 or to an intensity controller subsystem 340, which is preferably in communication or under the direction of the main controller 110. More particularly, when protons in the charged particle beam path pass through the material 330, some of the protons lose a small fraction of their energy, such as about one-tenth of a percent, which results in a secondary electron. That is, protons in the charged particle beam push some electrons when passing through material 330 giving the electrons enough energy to cause secondary emission. The resulting electron flow results in a current or signal that is proportional to the number of protons going through the target or extraction material 330. The resulting current is preferably converted to voltage and amplified. The resulting signal is referred to as a measured intensity signal.

The amplified signal or measured intensity signal resulting from the protons passing through the material 330 is optionally used in monitoring the intensity of the extracted protons and is preferably used in controlling the intensity of the extracted protons. For example, the measured intensity signal is compared to a goal signal, which is predetermined in an irradiation of the tumor plan. The difference between the measured intensity signal and the planned for goal signal is calculated. The difference is used as a control to the RF generator. Hence, the measured flow of current resulting from the protons passing through the material 330 is used as a control in the RF generator to increase or decrease the number of protons undergoing betatron oscillation and striking the material 330.

Hence, the voltage determined off of the material 330 is used as a measure of the orbital path and is used as a feedback control to control the RF cavity system.

In one example, the intensity controller subsystem 340 preferably additionally receives input from: (1) a detector 350, which provides a reading of the actual intensity of the proton beam and/or (2) an irradiation plan 360. The irradiation plan provides the desired intensity of the proton beam for each x, y, energy, and/or rotational position of the patient/tumor as a function of time. Thus, the intensity controller 340 receives the desired intensity from the irradiation plan 350, the actual intensity from the detector 350 and/or a measure of intensity from the material 330, and adjusts the amplitude and/or the duration of application of the applied radio-frequency field in the RF cavity system 310 to yield an intensity of the proton beam that matches the desired intensity from the irradiation plan 360.

As described, supra, the protons striking the material 330 is a step in the extraction of the protons from the synchrotron 130. Hence, the measured intensity signal is used to change the number of protons per unit time being extracted, which is referred to as intensity of the proton beam. The intensity of the proton beam is thus under algorithm control. Further, the intensity of the proton beam is controlled separately from the velocity of the protons in the synchrotron 130. Hence, intensity of the protons extracted and the energy of the protons extracted are independently variable. Still further, the intensity of the extracted protons is controllably variable while scanning the charged particles beam in the tumor from one voxel to an adjacent voxel as a separate hexapole and separated time period from acceleration and/or treatment is not required, as described supra.

For example, protons initially move at an equilibrium trajectory in the synchrotron 130. An RF field is used to excite or move the protons into a betatron oscillation. In one case, the frequency of the protons orbit is about 10 MHz. In one example, in about one millisecond or after about 10,000 orbits, the first protons hit an outer edge of the target material 130. The specific frequency is dependent upon the period of the orbit. Upon hitting the material 130, the protons push electrons through the foil to produce a current. The current is converted to voltage and amplified to yield a measured intensity signal. The measured intensity signal is used as a feedback input to control the applied RF magnitude or RF field. An energy beam sensor, described infra, is optionally used as a feedback control to the RF field frequency or RF field of the RF field extraction system 310 to dynamically control, modify, and/or alter the delivered charge particle beam energy, such as in a continuous pencil beam scanning system operating to treat tumor voxels without alternating between an extraction phase and a treatment phase. Preferably, the measured intensity signal is compared to a target signal and a measure of the difference between the measured intensity signal and target signal is used to adjust the applied RF field in the RF cavity system 310 in the extraction system to control the intensity of the protons in the extraction step. Stated again, the signal resulting from the protons striking and/or passing through the material 130 is used as an input in RF field modulation. An increase in the magnitude of the RF modulation results in protons hitting the foil or material 130 sooner. By increasing the RF, more protons are pushed into the foil, which results in an increased intensity, or more protons per unit time, of protons extracted from the synchrotron 130.

In another example, a detector 350 external to the synchrotron 130 is used to determine the flux of protons extracted from the synchrotron and a signal from the external detector is used to alter the RF field, RF intensity, RF amplitude, and/or RF modulation in the RF cavity system 310. Here the external detector generates an external signal, which is used in a manner similar to the measured intensity signal, described in the preceding paragraphs. Preferably, an algorithm or irradiation plan 360 is used as an input to the intensity controller 340, which controls the RF field modulation by directing the RF signal in the betatron oscillation generation in the RF cavity system 310. The irradiation plan 360 preferably includes the desired intensity of the charged particle beam as a function of time and/or energy of the charged particle beam as a function of time, for each patient rotation position, and/or for each x-, y-position of the charged particle beam.

In yet another example, when a current from material 330 resulting from protons passing through or hitting material is measured beyond a threshold, the RF field modulation in the RF cavity system is terminated or reinitiated to establish a subsequent cycle of proton beam extraction. This process is repeated to yield many cycles of proton beam extraction from the synchrotron accelerator.

In still yet another embodiment, intensity modulation of the extracted proton beam is controlled by the main controller 110. The main controller 110 optionally and/or additionally controls timing of extraction of the charged particle beam and energy of the extracted proton beam.

The benefits of the system include a multi-dimensional scanning system. Particularly, the system allows independence in: (1) energy of the protons extracted and (2) intensity of the protons extracted. That is, energy of the protons extracted is controlled by an energy control system and an intensity control system controls the intensity of the extracted protons. The energy control system and intensity control system are optionally independently controlled. Preferably, the main controller 110 controls the energy control system and the main controller 110 simultaneously controls the intensity control system to yield an extracted proton beam with controlled energy and controlled intensity where the controlled energy and controlled intensity are independently variable and/or continually available as a separate extraction phase and acceleration phase are not required, as described supra. Thus the irradiation spot hitting the tumor is under independent control of:
time;
energy;
intensity;
x-axis position, where the x-axis represents horizontal movement of the proton beam relative to the patient, and
y-axis position, where the y-axis represents vertical movement of the proton beam relative to the patient.

In addition, the patient is optionally independently translated and/or rotated relative to a translational axis of the proton beam at the same time.

Beam Transport

The beam transport system 135 is used to move the charged particles from the accelerator to the patient, such as via a nozzle in a gantry, described infra.

Charged Particle Energy

The beam transport system 135 optionally includes means for determining an energy of the charged particles in the charged particle beam. For example, an energy of the charged particle beam is determined via calculation, such as via equation 1, using knowledge of a magnet geometry and applied magnetic field to determine mass and/or energy. Referring now to equation 1, for a known magnet geometry, charge, q, and magnetic field, B, the Larmor radius, $\rho_L$, or magnet bend radius is defined as:

$$\rho_L = \frac{v_\perp}{\Omega_c} = \frac{\sqrt{2Em}}{qB} \qquad (\text{eq. 1})$$

where: $v_\perp$ is the ion velocity perpendicular to the magnetic field, $\Omega_c$ is the cyclotron frequency, q is the charge of the ion, B is the magnetic field, m is the mass of the charge particle, and E is the charged particle energy. Solving for the charged particle energy yields equation 2.

$$E = \frac{(\rho_L qB)^2}{2m} \qquad (\text{eq. 2})$$

Thus, an energy of the charged particle in the charged particle beam in the beam transport system 135 is calculable from the know magnet geometry, known or measured magnetic field, charged particle mass, charged particle charge, and the known magnet bend radius, which is proportional to and/or equivalent to the Larmor radius.

Nozzle

After extraction from the synchrotron 130 and transport of the charged particle beam along the proton beam path 268 in the beam transport system 135, the charged particle beam exits through the nozzle system 146. In one example, the nozzle system includes a nozzle foil covering an end of the nozzle system 146 or a cross-sectional area within the nozzle system forming a vacuum seal. The nozzle system includes a nozzle that expands in x/y-cross-sectional area along the z-axis of the proton beam path 268 to allow the proton beam 268 to be scanned along the x-axis and y-axis by the vertical control element and horizontal control element, respectively. The nozzle foil is preferably mechanically supported by the outer edges of an exit port of the nozzle or nozzle system 146. An example of a nozzle foil is a sheet of about 0.1 inch thick aluminum foil. Generally, the nozzle foil separates atmosphere pressures on the patient side of the nozzle foil from the low pressure region, such as about $10^{-5}$ to $10^{-7}$ torr region, on the synchrotron 130 side of the nozzle foil. The low pressure region is maintained to reduce scattering of the circulating charged particle beam in the synchrotron. Herein, the exit foil of the nozzle is optionally the first sheet 760 of the charged particle beam state determination system 750, described infra.

Charged Particle Control

Referring now to FIG. 4A, FIG. 4B, FIG. 5, FIG. 6A, and FIG. 6B, a charged particle beam control system is described where one or more patient specific beam control assemblies are removably inserted into the charged particle beam path proximate the nozzle of the charged particle cancer therapy system 100, where the patient specific beam control assemblies adjust the beam energy, diameter, cross-sectional shape, focal point, and/or beam state of the charged particle beam to properly couple energy of the charged particle beam to the individual's specific tumor.

Beam Control Tray

Referring now to FIG. 4A and FIG. 4B, a beam control tray assembly 400 is illustrated in a top view and side view, respectively. The beam control tray assembly 400 optionally comprises any of a tray frame 410, a tray aperture 412, a tray handle 420, a tray connector/communicator 430, and means for holding a patient specific tray insert 510, described infra. Generally, the beam control tray assembly 400 is used to: (1) hold the patient specific tray insert 510 in a rigid location relative to the beam control tray 400, (2) electronically identify the held patient specific tray insert 510 to the main controller 110, and (3) removably insert the patient specific tray insert 510 into an accurate and precise fixed location relative to the charged particle beam, such as the proton beam path 268 at the nozzle of the charged particle cancer therapy system 100.

For clarity of presentation and without loss of generality, the means for holding the patient specific tray insert 510 in the tray frame 410 of the beam control tray assembly 400 is illustrated as a set of recessed set screws 415. However, the means for holding the patient specific tray insert 510 relative to the rest of the beam control tray assembly 400 is optionally any mechanical and/or electromechanical positioning element, such as a latch, clamp, fastener, clip, slide, strap, or the like. Generally, the means for holding the patient specific tray insert 510 in the beam control tray 400 fixes the tray insert and tray frame relative to one another even when rotated along and/or around multiple axes, such as when attached to a charged particle cancer therapy system 100, nozzle system 146, dynamic gantry nozzle, or gantry nozzle, which is an optional element of the nozzle system 146, that moves in three-dimensional space relative to a fixed point in the beamline, proton beam path 268, and/or a given patient position. As illustrated in FIG. 4A and FIG. 4B, the recessed set screws 415 fix the patient specific tray insert 510 into the aperture 412 of the tray frame 410. The tray frame 410 is illustrated as circumferentially surrounding the patient specific tray insert 510, which aids in structural stability of the beam control tray assembly 400. However, generally the tray frame 410 is of any geometry that forms a stable beam control tray assembly 400.

Figure 5:
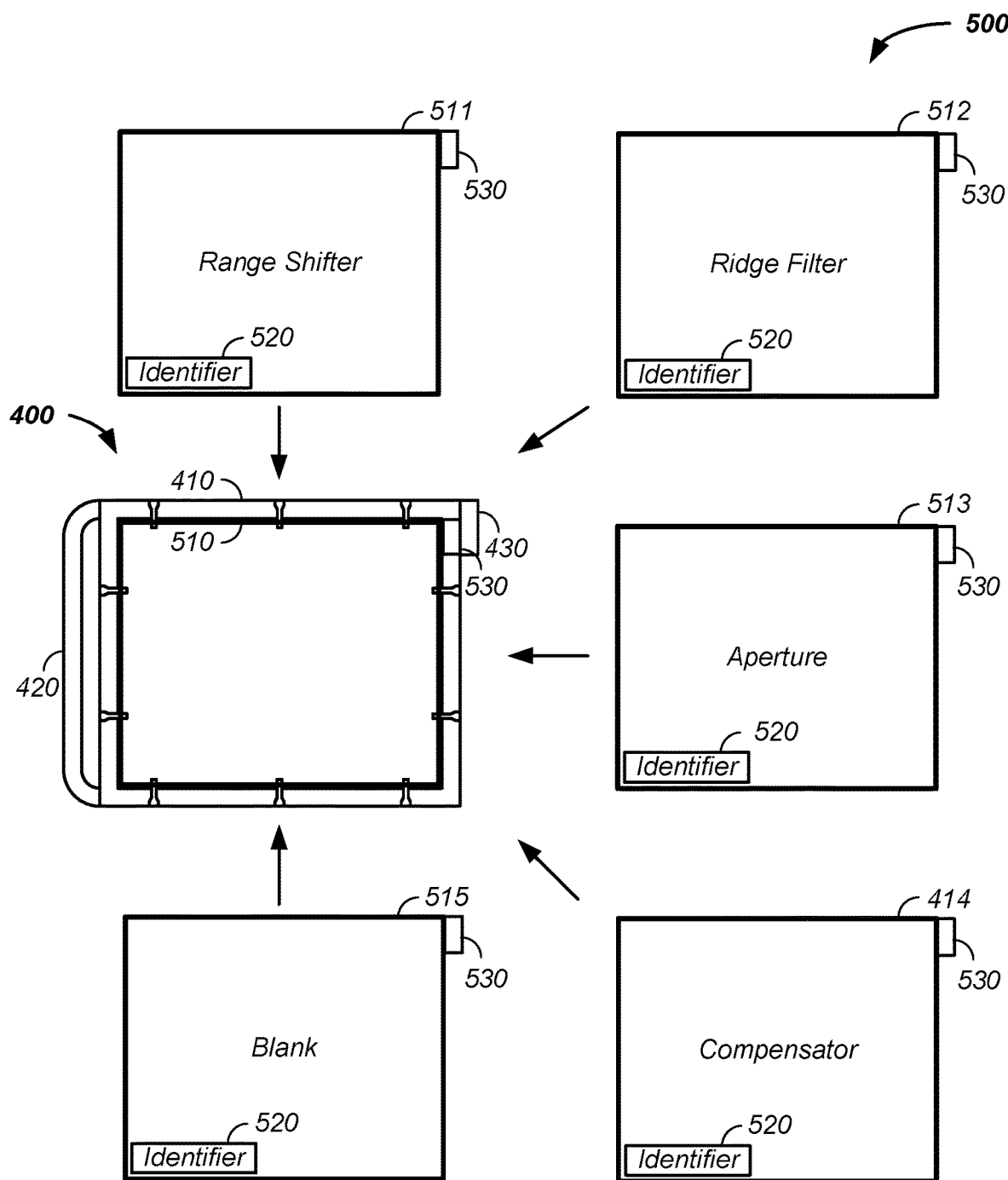
FIG. 5 illustrates patient specific tray inserts for insertion into the beam control tray.
Figure 6A:
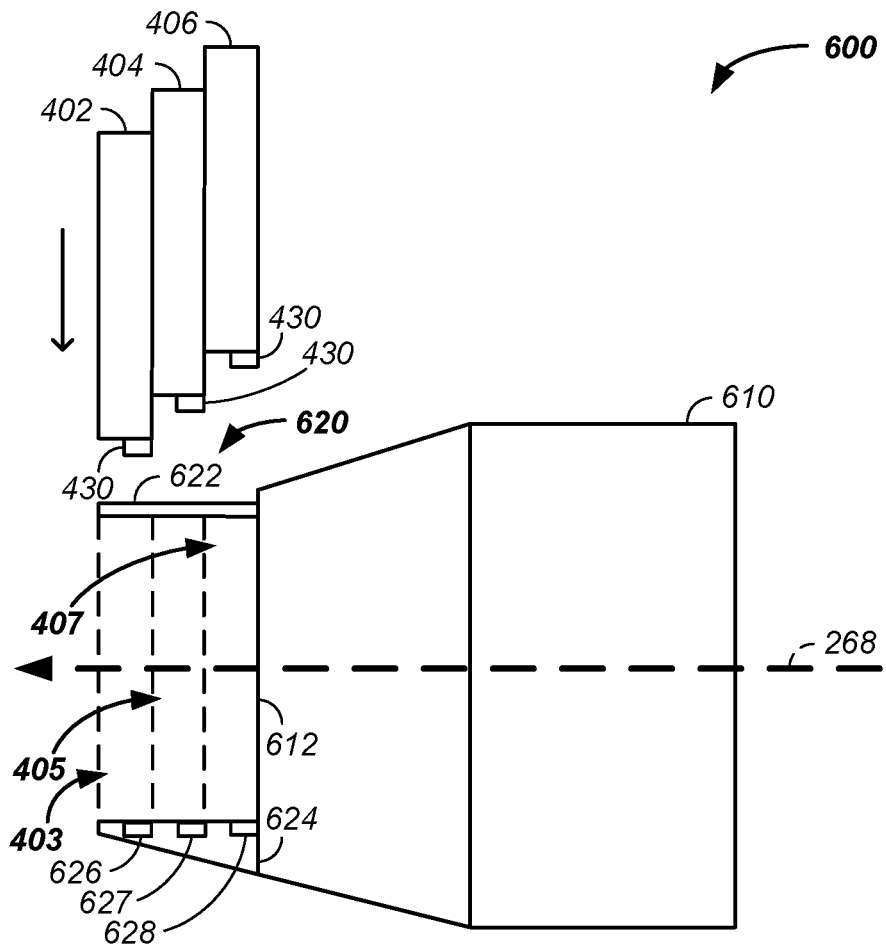
FIG. 6A illustrates insertion of the individualized tray assembly into the beam path and FIG. 6B illustrates retraction of the tray assembly into a nozzle of the charged particle cancer therapy system.

Still referring to FIG. 4A and now referring to FIG. 5 and FIG. 6A, the optional tray handle 420 is used to manually insert/retract the beam control tray assembly 400 into a receiving element of the gantry nozzle, nozzle system 146, or dynamic gantry nozzle. While the beam control tray assembly 400 is optionally inserted into the charged particle beam path 268 at any point after extraction from the synchrotron 130, the beam control tray assembly 400 is preferably inserted into the positively charged particle beam proximate the nozzle system 146 or dynamic gantry nozzle as control of the beam shape is preferably done with little space for the beam shape to defocus before striking the tumor. Optionally, insertion and/or retraction of the beam control tray assembly 400 is semi-automated, such as in a manner of a digital-video disk player receiving a digital-video disk, with a selected auto load and/or a selected auto unload feature.

Patient Specific Tray Insert

Referring again to FIG. 5, a system of assembling trays 500 is described. The beam control tray assembly 400 optionally and preferably has interchangeable patient specific tray inserts 510, such as a range shifter insert 511, a patient specific ridge filter insert 512, an aperture insert 513, a compensator insert 514, or a blank insert 515. As described, supra, any of the range shifter insert 511, the patient specific ridge filter insert 512, the aperture insert 513, the compensator insert 514, or the blank insert 515 after insertion into the tray frame 410 are inserted as the beam control tray assembly 400 into the positively charged particle beam path 268, such as proximate the nozzle system 146 or dynamic gantry nozzle.

Still referring to FIG. 5, the patient specific tray inserts 510 are further described. The patient specific tray inserts 510 comprise a combination of any of: (1) a standardized beam control insert and (2) a patient specific beam control insert. For example, the range shifter insert or 511 or compensator insert 514 used to control the depth of penetration of the charged particle beam into the patient is optionally: (a) a standard thickness of a beam slowing material, such as a first thickness of Lucite, an acrylic, a clear plastic, and/or a thermoplastic material, (b) one member of a set of members of varying thicknesses and/or densities where each member of the set of members slows the charged particles in the beam path by a known amount, or (c) is a material with a density and thickness designed to slow the charged particles by a customized amount for the individual patient being treated, based on the depth of the individual's tumor in the tissue, the thickness of intervening tissue, and/or the density of intervening bone/tissue. Similarly, the ridge filter insert 512 used to change the focal point or shape of the beam as a function of depth is optionally: (1) selected from a set of ridge filters where different members of the set of ridge filters yield different focal depths or (2) customized for treatment of the individual's tumor based on position of the tumor in the tissue of the individual. Similarly, the aperture insert is: (1) optionally selected from a set of aperture shapes or (2) is a customized individual aperture insert 513 designed for the specific shape of the individual's tumor. The blank insert 515 is an open slot, but serves the purpose of identifying slot occupancy, as described infra.

Slot Occupancy/Identification

Referring again to FIG. 4A, FIG. 4B, and FIG. 5, occupancy and identification of the particular patient specific tray insert 510 into the beam control tray assembly 400 is described. Generally, the beam control tray assembly 400 optionally contains means for identifying, to the main controller 110 and/or a treatment delivery control system described infra, the specific patient tray insert 510 and its location in the charged particle beam path 268. First, the particular tray insert is optionally labeled and/or communicated to the beam control tray assembly 400 or directly to the main controller 110. Second, the beam control tray assembly 400 optionally communicates the tray type and/or tray insert to the main controller 110. In various embodiments, communication of the particular tray insert to the main controller 110 is performed: (1) directly from the tray insert, (2) from the tray insert 510 to the tray assembly 400 and subsequently to the main controller 110, and/or (3) directly from the tray assembly 400. Generally, communication is performed wirelessly and/or via an established electromechanical link. Identification is optionally performed using a radio-frequency identification label, use of a barcode, or the like, and/or via operator input. Examples are provided to further clarify identification of the patient specific tray insert 510 in a given beam control tray assembly 400 to the main controller.

In a first example, one or more of the patient specific tray inserts 510, such as the range shifter insert 511, the patient specific ridge filter insert 512, the aperture insert 513, the compensator insert 514, or the blank insert 515 include an identifier 520 and/or and a first electromechanical identifier plug 530. The identifier 520 is optionally a label, a radio-frequency identification tag, a barcode, a 2-dimensional bar-code, a matrix-code, or the like. The first electromechanical identifier plug 530 optionally includes memory programmed with the particular patient specific tray insert information and a connector used to communicate the information to the beam control tray assembly 400 and/or to the main controller 110. As illustrated in FIG. 5, the first electromechanical identifier plug 530 affixed to the patient specific tray insert 510 plugs into a second electromechanical identifier plug, such as the tray connector/communicator 430, of the beam control tray assembly 400, which is described infra.

In a second example, the beam control tray assembly 400 uses the second electromechanical identifier plug to send occupancy, position, and/or identification information related to the type of tray insert or the patient specific tray insert 510 associated with the beam control tray assembly to the main controller 110. For example, a first tray assembly is configured with a first tray insert and a second tray assembly is configured with a second tray insert. The first tray assembly sends information to the main controller 110 that the first tray assembly holds the first tray insert, such as a range shifter, and the second tray assembly sends information to the main controller 110 that the second tray assembly holds the second tray insert, such as an aperture. The second electromechanical identifier plug optionally contains programmable memory for the operator to input the specific tray insert type, a selection switch for the operator to select the tray insert type, and/or an electromechanical connection to the main controller. The second electromechanical identifier plug associated with the beam control tray assembly 400 is optionally used without use of the first electromechanical identifier plug 530 associated with the tray insert 510.

In a third example, one type of tray connector/communicator 430 is used for each type of patient specific tray insert 510. For example, a first connector/communicator type is used for holding a range shifter insert 511, while a second, third, fourth, and fifth connector/communicator type is used for trays respectively holding a patient specific ridge filter insert 512, an aperture insert 513, a compensator insert 514, or a blank insert 515. In one case, the tray communicates tray type with the main controller. In a second case, the tray communicates patient specific tray insert information with the main controller, such as an aperture identifier custom built for the individual patient being treated.

Tray Insertion/Coupling

Figure 6B:
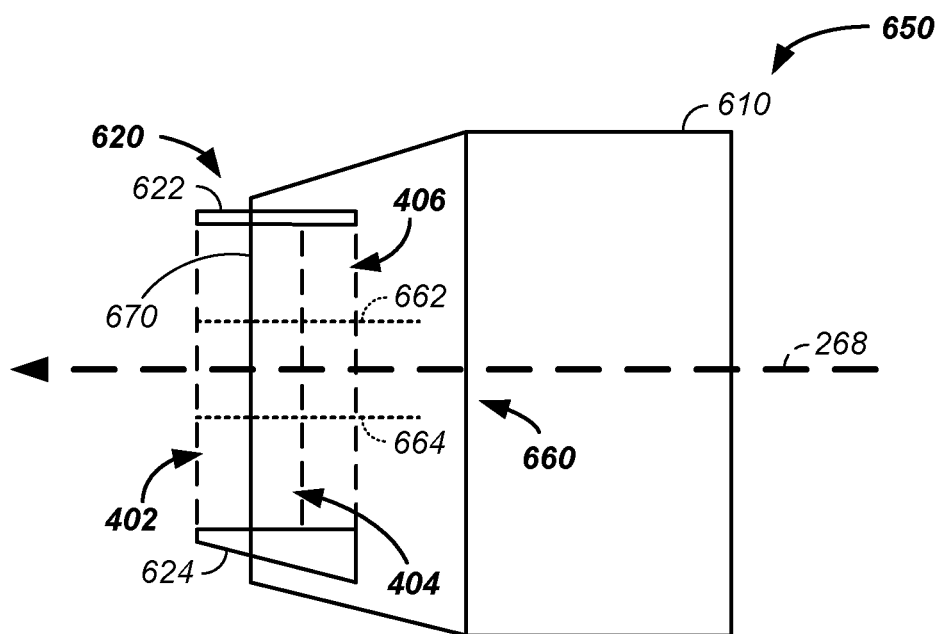

Referring now to FIG. 6A and FIG. 6B a beam control insertion process 600 is described. The beam control insertion process 600 comprises: (1) insertion of the beam control tray assembly 400 and the associated patient specific tray insert 510 into the charged particle beam path 268 and/or dynamic gantry nozzle 610, such as into a tray assembly receiver 620 and (2) an optional partial or total retraction of beam of the tray assembly receiver 620 into the dynamic gantry nozzle 610.

Referring now to FIG. 6A, insertion of one or more of the beam control tray assemblies 400 and the associated patient specific tray inserts 510 into the dynamic gantry nozzle 610 is further described. In FIG. 6A, three beam control tray assemblies, of a possible n tray assemblies, are illustrated, a first tray assembly 402, a second tray assembly 404, and a third tray assembly 406, where n is a positive integer of 1, 2, 3, 4, 5 or more. As illustrated, the first tray assembly 402 slides into a first receiving slot 403, the second tray assembly 404 slides into a second receiving slot 405, and the third tray assembly 406 slides into a third receiving slot 407. Generally, any tray optionally inserts into any slot or tray types are limited to particular slots through use of a mechanical, physical, positional, and/or steric constraints, such as a first tray type configured for a first insert type having a first size and a second tray type configured for a second insert type having a second distinct size at least ten percent different from the first size.

Still referring to FIG. 6A, identification of individual tray inserts inserted into individual receiving slots is further described. As illustrated, sliding the first tray assembly 402 into the first receiving slot 403 connects the associated electromechanical connector/communicator 430 of the first tray assembly 402 to a first receptor 626. The electromechanical connector/communicator 430 of the first tray assembly communicates tray insert information of the first beam control tray assembly to the main controller 110 via the first receptor 626. Similarly, sliding the second tray assembly 404 into the second receiving slot 405 connects the associated electromechanical connector/communicator 430 of the second tray assembly 404 into a second receptor 627, which links communication of the associated electromechanical connector/communicator 430 with the main controller 110 via the second receptor 627, while a third receptor 628 connects to the electromechanical connected placed into the third slot 407. The non-wireless/direct connection is preferred due to the high radiation levels within the treatment room and the high shielding of the treatment room, which both hinder wireless communication. The connection of the communicator and the receptor is optionally of any configuration and/or orientation.

Tray Receiver Assembly Retraction

Referring again to FIG. 6A and FIG. 6B, retraction of the tray receiver assembly 620 relative to a nozzle end 612 of the dynamic gantry nozzle 610 is described. The tray receiver assembly 620 comprises a framework to hold one or more of the beam control tray assemblies 400 in one or more slots, such as through use of a first tray receiver assembly side 622 through which the beam control tray assemblies 400 are inserted and/or through use of a second tray receiver assembly side 624 used as a backstop, as illustrated holding the plugin receptors configured to receive associated tray connector/communicators 430, such as the first, second, and third receptors 626, 627, 628. Optionally, the tray receiver assembly 620 retracts partially or completely into the dynamic gantry nozzle 610 using a retraction mechanism 660 configured to alternately retract and extend the tray receiver assembly 620 relative to a nozzle end 612 of the gantry nozzle 610, such as along a first retraction track 662 and a second retraction track 664 using one or more motors and computer control. Optionally the tray receiver assembly 620 is partially or fully retracted when moving the gantry, nozzle, and/or gantry nozzle 610 to avoid physical constraints of movement, such as potential collision with another object in the patient treatment room.

For clarity of presentation and without loss of generality, several examples of loading patient specific tray inserts into tray assemblies with subsequent insertion into an positively charged particle beam path proximate a gantry nozzle 610 are provided.

In a first example, a single beam control tray assembly 400 is used to control the charged particle beam 268 in the charged particle cancer therapy system 100. In this example, a patient specific range shifter insert 511, which is custom fabricated for a patient, is loaded into a patient specific tray insert 510 to form a first tray assembly 402, where the first tray assembly 402 is loaded into the third receptor 628, which is fully retracted into the gantry nozzle 610.

In a second example, two beam control assemblies 400 are used to control the charged particle beam 268 in the charged particle cancer therapy system 100. In this example, a patient specific ridge filter 512 is loaded into a first tray assembly 402, which is loaded into the second receptor 627 and a patient specific aperture 513 is loaded into a second tray assembly 404, which is loaded into the first receptor 626 and the two associated tray connector/communicators 430 using the first receptor 626 and second receptor 627 communicate to the main controller 110 the patient specific tray inserts 510. The tray receiver assembly 620 is subsequently retracted one slot so that the patient specific ridge filter 512 and the patient specific aperture reside outside of and at the nozzle end 612 of the gantry nozzle 610.

In a third example, three beam control tray assemblies 400 are used, such as a range shifter 511 in a first tray inserted into the first receiving slot 403, a compensator in a second tray inserted into the second receiving slot 405, and an aperture in a third tray inserted into the third receiving slot 407.

Generally, any patient specific tray insert 510 is inserted into a tray frame 410 to form a beam control tray assembly 400 inserted into any slot of the tray receiver assembly 620 and the tray assembly is not retracted or retracted any distance into the gantry nozzle 610.

Tomography/Beam State

In one embodiment, the charged particle tomography apparatus is used to image a tumor in a patient. As current beam position determination/verification is used in both tomography and cancer therapy treatment, for clarity of presentation and without limitation beam state determination is also addressed in this section. However, beam state determination is optionally used separately and without tomography.

In another example, the charged particle tomography apparatus is used in combination with a charged particle cancer therapy system using common elements. For example, tomographic imaging of a cancerous tumor is performed using charged particles generated with an injector, accelerator, and guided with a delivery system that are part of the cancer therapy system, described supra.

In various examples, the tomography imaging system is optionally simultaneously operational with a charged particle cancer therapy system using common elements, allows tomographic imaging with rotation of the patient, is operational on a patient in an upright, semi-upright, and/or horizontal position, is simultaneously operational with X-ray imaging, and/or allows use of adaptive charged particle cancer therapy. Further, the common tomography and cancer therapy apparatus elements are optionally operational in a multi-axis and/or multi-field raster beam mode.

In conventional medical X-ray tomography, a sectional image through a body is made by moving one or both of an X-ray source and the X-ray film in opposite directions during the exposure. By modifying the direction and extent of the movement, operators can select different focal planes, which contain the structures of interest. More modern variations of tomography involve gathering projection data from multiple directions by moving the X-ray source and feeding the data into a tomographic reconstruction software algorithm processed by a computer. Herein, in stark contrast to known methods, the radiation source is a charged particle, such as a proton ion beam or a carbon ion beam. A proton beam is used herein to describe the tomography system, but the description applies to a heavier ion beam, such as a carbon ion beam. Further, in stark contrast to known techniques, herein the radiation source is preferably stationary while the patient is rotated.

Figure 7:
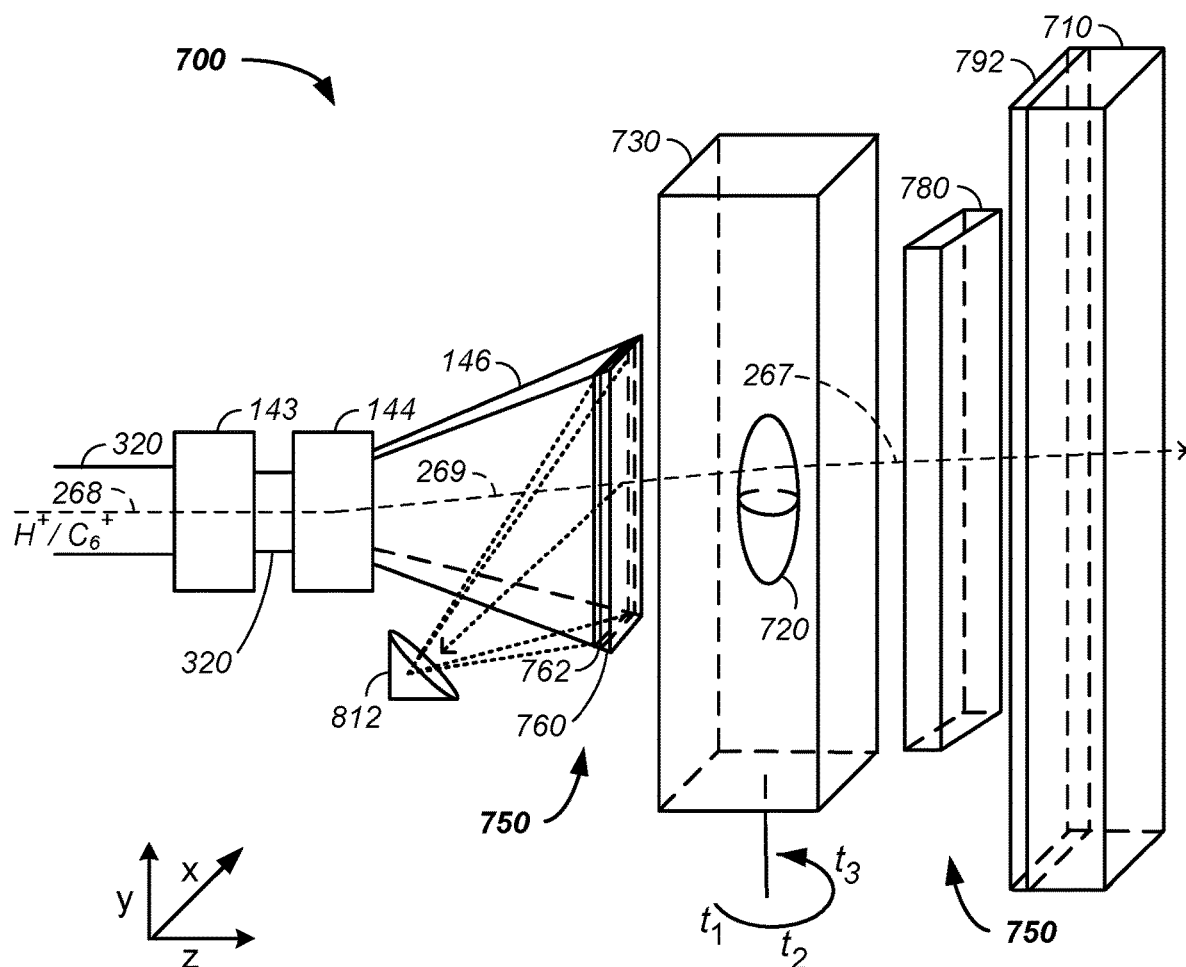
FIG. 7 illustrates a tomography system.

Referring now to FIG. 7, an example of a tomography apparatus is described and an example of a beam state determination is described. In this example, the tomography system 700 uses elements in common with the charged particle beam system 100, including elements of one or more of the injection system 120, the accelerator 130, a positively charged particle beam transport path 268 within a beam transport housing 320 in the beam transport system 135, the targeting/delivery system 140, the patient interface module 150, the display system 160, and/or the imaging system 170, such as the X-ray imaging system. The scintillation material is optionally one or more scintillation plates, such as a scintillating plastic, used to measure energy, intensity, and/or position of the charged particle beam. For instance, a scintillation material 710 or scintillation plate is positioned behind the patient 730 relative to the targeting/delivery system 140 elements, which is optionally used to measure intensity and/or position of the charged particle beam after transmitting through the patient. Optionally, a second scintillation plate or a charged particle induced photon emitting sheet, described infra, is positioned prior to the patient 730 relative to the targeting/delivery system 140 elements, which is optionally used to measure incident intensity and/or position of the charged particle beam prior to transmitting through the patient. The charged particle beam system 100 as described has proven operation at up to and including 330 MeV, which is sufficient to send protons through the body and into contact with the scintillation material. Particularly, 250 MeV to 330 MeV are used to pass the beam through a standard sized patient with a standard sized pathlength, such as through the chest. The intensity or count of protons hitting the plate as a function of position is used to create an image. The velocity or energy of the proton hitting the scintillation plate is also used in creation of an image of the tumor 720 and/or an image of the patient 730. The patient 730 is rotated about the y-axis and a new image is collected. Preferably, a new image is collected with about every one degree of rotation of the patient resulting in about 360 images that are combined into a tomogram using tomographic reconstruction software. The tomographic reconstruction software uses overlapping rotationally varied images in the reconstruction. Optionally, a new image is collected at about every 2, 3, 4, 5, 10, 15, 30, or 45 degrees of rotation of the patient.

Herein, the scintillation material 710 or scintillator is any material that emits a photon when struck by a positively charged particle or when a positively charged particle transfers energy to the scintillation material sufficient to cause emission of light. Optionally, the scintillation material emits the photon after a delay, such as in fluorescence or phosphorescence. However, preferably, the scintillator has a fast fifty percent quench time, such as less than 0.0001, 0.001, 0.01, 0.1, 1, 10, 100, or 1,000 milliseconds, so that the light emission goes dark, falls off, or terminates quickly. Preferred scintillation materials include sodium iodide, potassium iodide, cesium iodide, an iodide salt, and/or a doped iodide salt. Additional examples of the scintillation materials include, but are not limited to: an organic crystal, a plastic, a glass, an organic liquid, a luminophor, and/or an inorganic material or inorganic crystal, such as barium fluoride, $BaF_2$; calcium fluoride, $CaF_2$, doped calcium fluoride, sodium iodide, NaI; doped sodium iodide, sodium iodide doped with thallium, NaI(Tl); cadmium tungstate, $CdWO_4$; bismuth germanate; cadmium tungstate, $CdWO_4$; calcium tungstate, $CaWO_4$; cesium iodide, CsI; doped cesium iodide; cesium iodide doped with thallium, CsI(Tl); cesium iodide doped with sodium CsI(Na); potassium iodide, KI; doped potassium iodide, gadolinium oxysulfide, $Gd_2O_2S$; lanthanum bromide doped with cerium, $LaBr_3(Ce)$; lanthanum chloride, $LaCl_3$; cesium doped lanthanum chloride, $LaCl_3(Ce)$; lead tungstate, $PbWO_4$; LSO or lutetium oxyorthosilicate $(Lu_2SiO_5)$; LYSO, $Lu_{1.8}Y_{0.2}SiO_5(Ce)$; yttrium aluminum garnet, YAG(Ce); zinc sulfide, ZnS(Ag); and zinc tungstate, $ZnWO_4$.

In one embodiment, a tomogram or an individual tomogram section image is collected at about the same time as cancer therapy occurs using the charged particle beam system 100. For example, a tomogram is collected and cancer therapy is subsequently performed: without the patient moving from the positioning systems, such as in a semi-vertical partial immobilization system, a sitting partial immobilization system, or the a laying position. In a second example, an individual tomogram slice is collected using a first cycle of the accelerator 130 and using a following cycle of the accelerator 130, the tumor 720 is irradiated, such as within about 1, 2, 5, 10, 15 or 30 seconds. In a third case, about 2, 3, 4, or 5 tomogram slices are collected using 1, 2, 3, 4, or more rotation positions of the patient 730 within about 5, 10, 15, 30, or 60 seconds of subsequent tumor irradiation therapy.

In another embodiment, the independent control of the tomographic imaging process and X-ray collection process allows simultaneous single and/or multi-field collection of X-ray images and tomographic images easing interpretation of multiple images. Indeed, the X-ray and tomographic images are optionally overlaid to from a hybrid X-ray/proton beam tomographic image as the patient 730 is optionally in the same position for each image.

In still another embodiment, the tomogram is collected with the patient 730 in the about the same position as when the patient's tumor is treated using subsequent irradiation therapy. For some tumors, the patient being positioned in the same upright or semi-upright position allows the tumor 720 to be separated from surrounding organs or tissue of the patient 730 better than in a laying position. Positioning of the scintillation material 710 behind the patient 730 allows the tomographic imaging to occur while the patient is in the same upright or semi-upright position.

The use of common elements in the tomographic imaging and in the charged particle cancer therapy allows benefits of the cancer therapy, described supra, to optionally be used with the tomographic imaging, such as proton beam x-axis control, proton beam y-axis control, control of proton beam energy, control of proton beam intensity, timing control of beam delivery to the patient, rotation control of the patient, and control of patient translation all in a raster beam mode of proton energy delivery. The use of a single proton or cation beamline for both imaging and treatment facilitates eases patient setup, reduces alignment uncertainties, reduces beam sate uncertainties, and eases quality assurance.

In yet still another embodiment, initially a three-dimensional tomographic proton based reference image is collected, such as with hundreds of individual rotation images of the tumor 720 and patient 730. Subsequently, just prior to proton treatment of the cancer, just a few 2-dimensional control tomographic images of the patient are collected, such as with a stationary patient or at just a few rotation positions, such as an image straight on to the patient, with the patient rotated about 45 degrees each way, and/or the patient rotated about 90 degrees each way about the y-axis. The individual control images are compared with the 3-dimensional reference image. An adaptive proton therapy is subsequently performed where: (1) the proton cancer therapy is not used for a given position based on the differences between the 3-dimensional reference image and one or more of the 2-dimensional control images and/or (2) the proton cancer therapy is modified in real time based on the differences between the 3-dimensional reference image and one or more of the 2-dimensional control images.

Charged Particle State Determination/Verification/Photonic Monitoring

Still referring to FIG. 7, the tomography system 700 is optionally used with a charged particle beam state determination system 750, optionally used as a charged particle verification system. The charged particle state determination system 750 optionally measures, determines, and/or verifies one of more of: (1) position of the charged particle beam, such as the treatment beam 269, (2) direction of the treatment beam 269, (3) intensity of the treatment beam 269, (4) energy of the treatment beam 269, (5) position, direction, intensity, and/or energy of the charged particle beam, such as a residual charged particle beam 267 after passing through a sample or the patient 730, and (6) a history of the charged particle beam.

Figure 8:
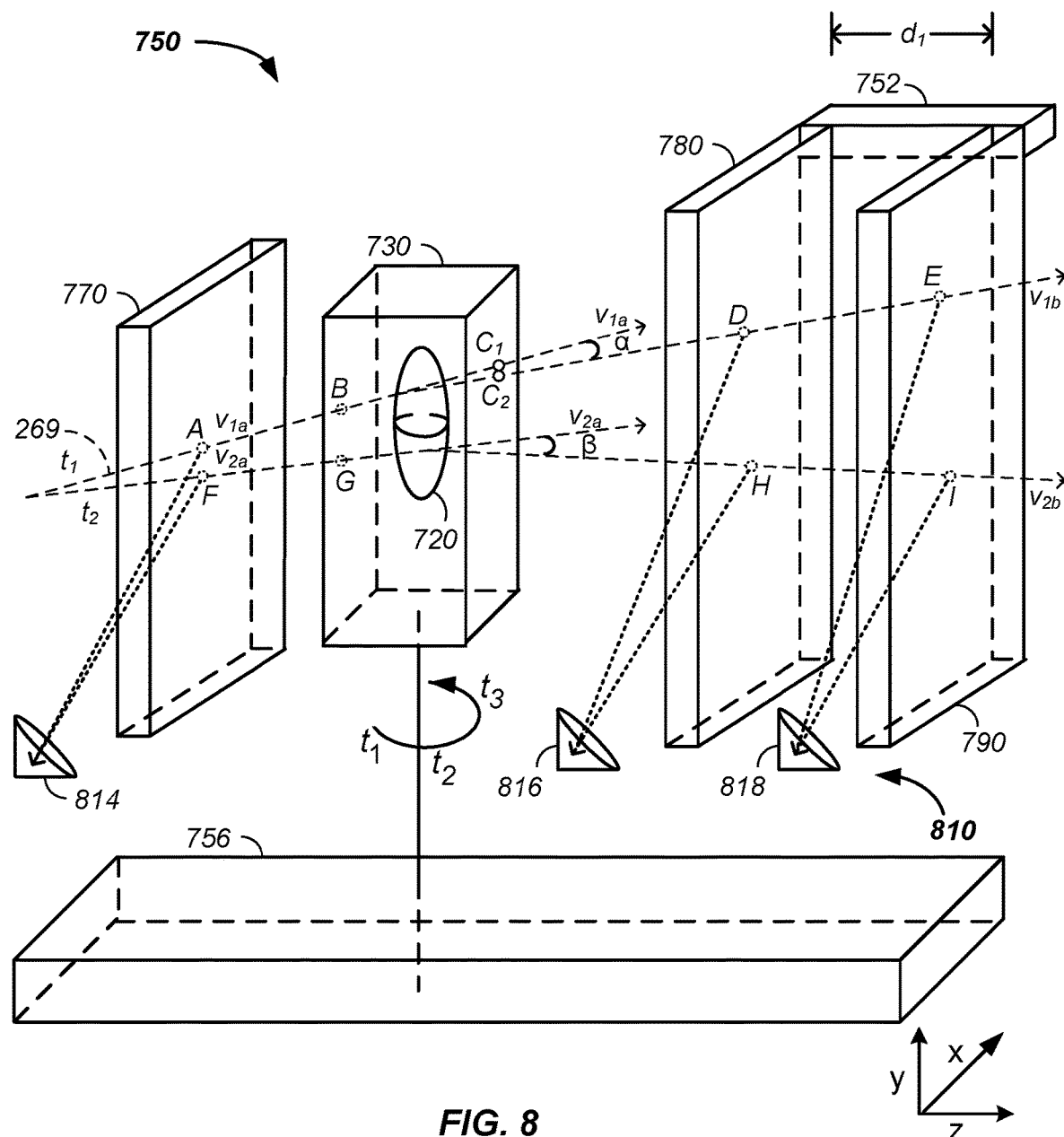
FIG. 8 illustrates a beam path identification system.
Figure 9A:
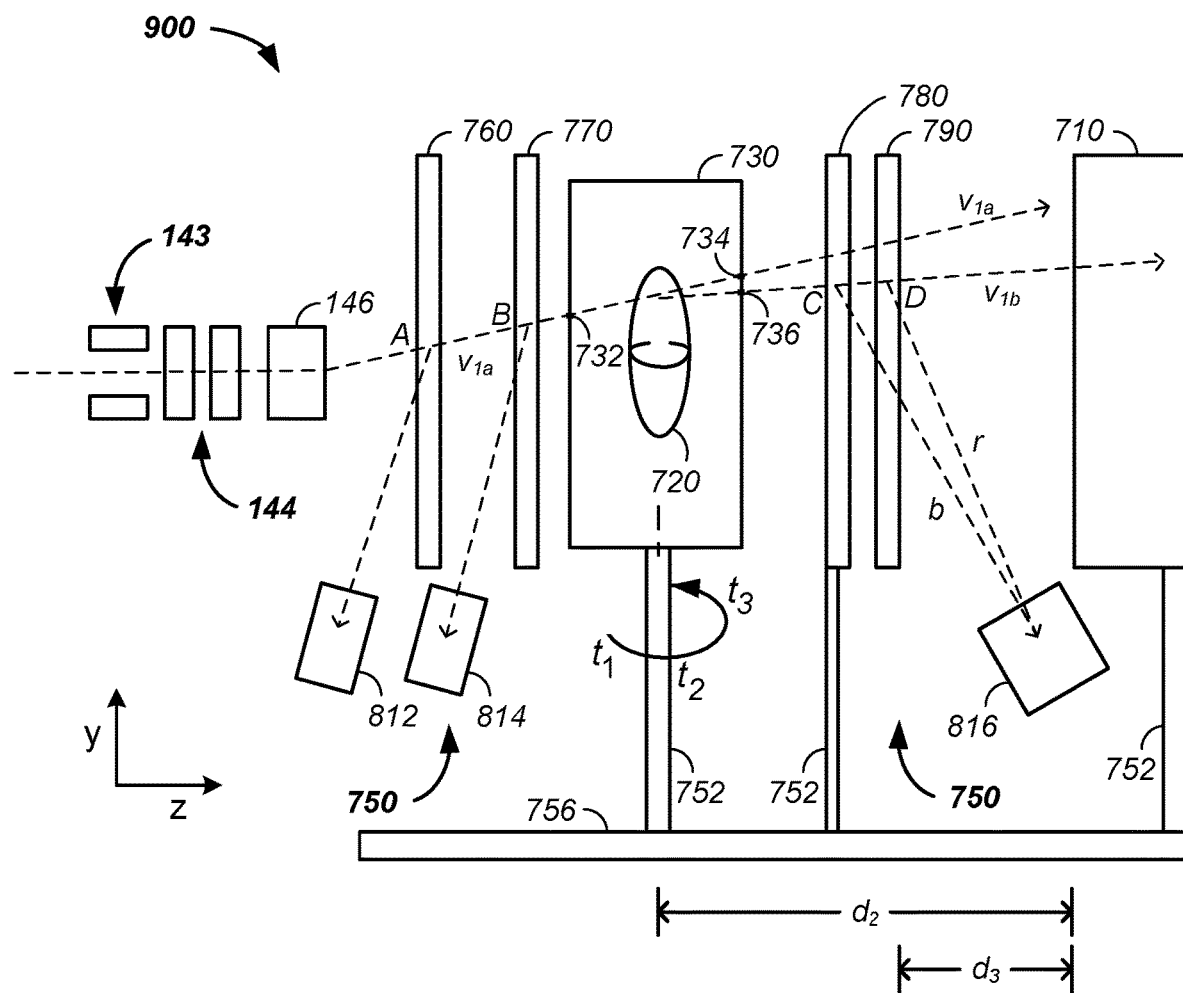
FIG. 9A illustrates a beam path identification system coupled to a beam transport system and a tomography scintillation detector and FIG. 9B illustrates the scintillation detector rotating with the patient and gantry nozzle.

For clarity of presentation and without loss of generality, a description of the charged particle beam state determination system 750 is described and illustrated separately in FIG. 8 and FIG. 9A; however, as described herein elements of the charged particle beam state determination system 750 are optionally and preferably integrated into the nozzle system 146 and/or the tomography system 700 of the charged particle treatment system 100. More particularly, any element of the charged particle beam state determination system 750 is integrated into the nozzle system 146, the dynamic gantry nozzle 610, and/or tomography system 700, such as a surface of the scintillation material 710 or a surface of a scintillation detector, plate, or system. The nozzle system 146 or the dynamic gantry nozzle 610 provides an outlet of the charged particle beam from the vacuum tube initiating at the injection system 120 and passing through the synchrotron 130 and beam transport system 135. Any plate, sheet, fluorophore, or detector of the charged particle beam state determination system is optionally integrated into the nozzle system 146. For example, an exit foil of the nozzle 610 is optionally a first sheet 760 of the charged particle beam state determination system 750 and a first coating 762 is optionally coated onto the exit foil, as illustrated in FIG. 7. Similarly, optionally a surface of the scintillation material 710 is a support surface for a fourth coating 792, as illustrated in FIG. 7. The charged particle beam state determination system 750 is further described, infra.

Referring now to FIG. 7, FIG. 8, and FIG. 9A, four sheets, a first sheet 760, a second sheet 770, a third sheet 780, and a fourth sheet 790 are used to illustrated detection sheets and/or photon emitting sheets upon transmittance of a charged particle beam. Each sheet is optionally coated with a photon emitter, such as a fluorophore, such as the first sheet 760 is optionally coated with a first coating 762. Without loss of generality and for clarity of presentation, the four sheets are each illustrated as units, where the light emitting layer is not illustrated. Thus, for example, the second sheet 770 optionally refers to a support sheet, a light emitting sheet, and/or a support sheet coated by a light emitting element. The four sheets are representative of n sheets, where n is a positive integer.

Referring now to FIG. 7 and FIG. 8, the charged particle beam state verification system 750 is a system that allows for monitoring of the actual charged particle beam position in real-time without destruction of the charged particle beam. The charged particle beam state verification system 750 preferably includes a first position element or first beam verification layer, which is also referred to herein as a coating, luminescent, fluorescent, phosphorescent, radiance, or viewing layer. The first position element optionally and preferably includes a coating or thin layer substantially in contact with a sheet, such as an inside surface of the nozzle foil, where the inside surface is on the synchrotron side of the nozzle foil. Less preferably, the verification layer or coating layer is substantially in contact with an outer surface of the nozzle foil, where the outer surface is on the patient treatment side of the nozzle foil. Preferably, the nozzle foil provides a substrate surface for coating by the coating layer. Optionally, a binding layer is located between the coating layer and the nozzle foil, substrate, or support sheet. Optionally, the position element is placed anywhere in the charged particle beam path. Optionally, more than one position element on more than one sheet, respectively, is used in the charged particle beam path and is used to determine a state property of the charged particle beam, as described infra.

Still referring to FIG. 7 and FIG. 8, the coating, referred to as a fluorophore, yields a measurable spectroscopic response, spatially viewable by a detector or camera, as a result of transmission by the proton beam. The coating is preferably a phosphor, but is optionally any material that is viewable or imaged by a detector where the material changes spectroscopically as a result of the charged particle beam hitting or transmitting through the coating or coating layer. A detector or camera views secondary photons emitted from the coating layer and determines a position of a treatment beam 269, which is also referred to as a current position of the charged particle beam or final treatment vector of the charged particle beam, by the spectroscopic differences resulting from protons and/or charged particle beam passing through the coating layer. For example, the camera views a surface of the coating surface as the proton beam or positively charged cation beam is being scanned by the first axis control 143, vertical control, and the second axis control 144, horizontal control, beam position control elements during treatment of the tumor 720. The camera views the current position of the charged particle beam or treatment beam 269 as measured by spectroscopic response. The coating layer is preferably a phosphor or luminescent material that glows and/or emits photons for a short period of time, such as less than 5 seconds for a 50% intensity, as a result of excitation by the charged particle beam. The detector observes the temperature change and/or observe photons emitted from the charged particle beam traversed spot. Optionally, a plurality of cameras or detectors are used, where each detector views all or a portion of the coating layer. For example, two detectors are used where a first detector views a first half of the coating layer and the second detector views a second half of the coating layer. Preferably, at least a portion of the detector is mounted into the nozzle system to view the proton beam position after passing through the first axis and second axis controllers 143, 144. Preferably, the coating layer is positioned in the proton beam path 268 in a position prior to the protons striking the patient 730.

Figure 10:
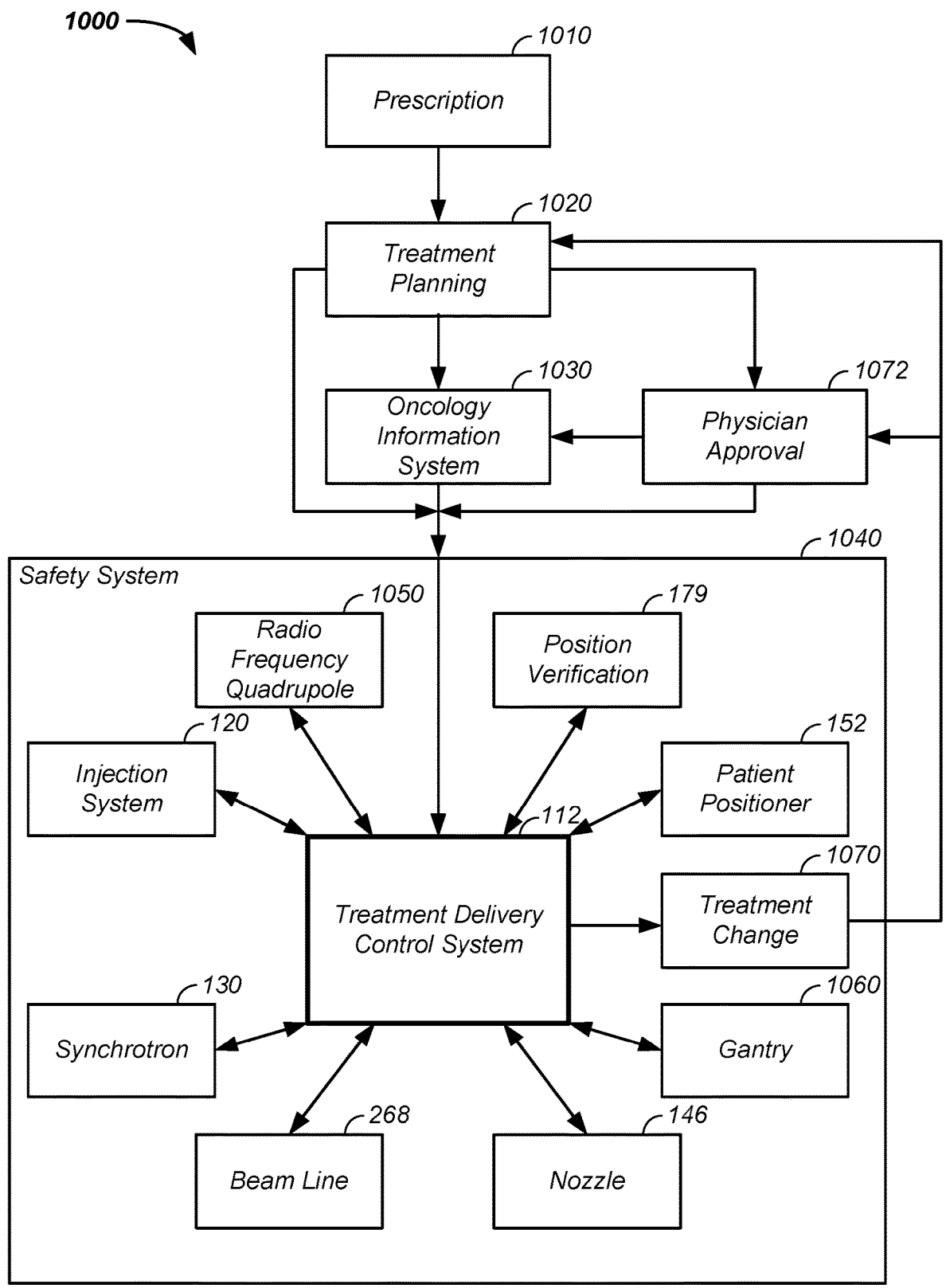
FIG. 10 illustrates a treatment delivery control system.

Referring now to FIG. 1 and FIG. 7, the main controller 110, connected to the camera or detector output, optionally and preferably compares the final proton beam position or position of the treatment beam 269 with the planned proton beam position and/or a calibration reference to determine if the actual proton beam position or position of the treatment beam 269 is within tolerance. The charged particle beam state determination system 750 preferably is used in one or more phases, such as a calibration phase, a mapping phase, a beam position verification phase, a treatment phase, and a treatment plan modification phase. The calibration phase is used to correlate, as a function of x-, y-position of the glowing response the actual x-, y-position of the proton beam at the patient interface. During the treatment phase, the charged particle beam position is monitored and compared to the calibration and/or treatment plan to verify accurate proton delivery to the tumor 720 and/or as a charged particle beam shutoff safety indicator. Referring now to FIG. 10, the position verification system 179 and/or the treatment delivery control system 112, upon determination of a tumor shift, an unpredicted tumor distortion upon treatment, and/or a treatment anomaly optionally generates and or provides a recommended treatment change 1070. The treatment change 1070 is optionally sent out while the patient 730 is still in the treatment position, such as to a proximate physician or over the internet to a remote physician, for physician approval 1072, receipt of which allows continuation of the now modified and approved treatment plan.

Example I

Referring now to FIG. 7, a first example of the charged particle beam state determination system 750 is illustrated using two cation induced signal generation surfaces, referred to herein as the first sheet 760 and a third sheet 780. Each sheet is described below.

Still referring to FIG. 7, in the first example, the optional first sheet 760, located in the charged particle beam path prior to the patient 730, is coated with a first fluorophore coating 762, wherein a cation, such as in the charged particle beam, transmitting through the first sheet 760 excites localized fluorophores of the first fluorophore coating 762 with resultant emission of one or more photons. In this example, a first detector 812 images the first fluorophore coating 762 and the main controller 110 determines a current position of the charged particle beam using the image of the fluorophore coating 762 and the detected photon(s). The intensity of the detected photons emitted from the first fluorophore coating 762 is optionally used to determine the intensity of the charged particle beam used in treatment of the tumor 720 or detected by the tomography system 700 in generation of a tomogram and/or tomographic image of the tumor 720 of the patient 730. Thus, a first position and/or a first intensity of the charged particle beam is determined using the position and/or intensity of the emitted photons, respectively.

Still referring to FIG. 7, in the first example, the optional third sheet 780, positioned posterior to the patient 730, is optionally a cation induced photon emitting sheet as described in the previous paragraph. However, as illustrated, the third sheet 780 is a solid state beam detection surface, such as a detector array. For instance, the detector array is optionally a charge coupled device, a charge induced device, CMOS, or camera detector where elements of the detector array are read directly, as does a commercial camera, without the secondary emission of photons. Similar to the detection described for the first sheet, the third sheet 780 is used to determine a position of the charged particle beam and/or an intensity of the charged particle beam using signal position and/or signal intensity from the detector array, respectively.

Still referring to FIG. 7, in the first example, signals from the first sheet 760 and third sheet 780 yield a position before and after the patient 730 allowing a more accurate determination of the charged particle beam through the patient 730 therebetween. Optionally, knowledge of the charged particle beam path in the targeting/delivery system 740, such as determined via a first magnetic field strength across the first axis control 143 or a second magnetic field strength across the second axis control 144 is combined with signal derived from the first sheet 760 to yield a first vector of the charged particles prior to entering the patient 730 and/or an input point of the charged particle beam into the patient 730, which also aids in: (1) controlling, monitoring, and/or recording tumor treatment and/or (2) tomography development/interpretation. Optionally, signal derived from use of the third sheet 780, posterior to the patient 730, is combined with signal derived from tomography system 700, such as the scintillation material 710, to yield a second vector of the charged particles posterior to the patient 730 and/or an output point of the charged particle beam from the patient 730, which also aids in: (1) controlling, monitoring, deciphering, and/or (2) interpreting a tomogram or a tomographic image.

For clarity of presentation and without loss of generality, detection of photons emitted from sheets is used to further describe the charged particle beam state determination system 750. However, any of the cation induced photon emission sheets described herein are alternatively detector arrays. Further, any number of cation induced photon emission sheets are used prior to the patient 730 and/or posterior to the patient 730, such a 1, 2, 3, 4, 6, 8, 10, or more. Still further, any of the cation induced photon emission sheets are place anywhere in the charged particle beam, such as in the synchrotron 130, in the beam transport system 135, in the targeting/delivery system 140, the nozzle system 146, in the gantry room, and/or in the tomography system 700. Any of the cation induced photon emission sheets are used in generation of a beam state signal as a function of time, which is optionally recorded, such as for an accurate history of treatment of the tumor 720 of the patient 730 and/or for aiding generation of a tomographic image.

Example II

Referring now to FIG. 8, a second example of the charged particle beam state determination system 750 is illustrated using three cation induced signal generation surfaces, referred to herein as the second sheet 770, the third sheet 780, and the fourth sheet 790. Any of the second sheet 770, the third sheet 780, and the fourth sheet 790 contain any of the features of the sheets described supra.

Still referring to FIG. 8, in the second example, the second sheet 770, positioned prior to the patient 730, is optionally integrated into the nozzle and/or the nozzle system 146, but is illustrated as a separate sheet. Signal derived from the second sheet 770, such as at point A, is optionally combined with signal from the first sheet 760 and/or state of the targeting/delivery system 140 to yield a first vector, $v_{1a}$, from point A to point B of the charged particle beam prior to the sample or patient 730 at a first time, $t_1$, and a second vector, $v_{2a}$, from point F to point G of the charged particle beam prior to the sample at a second time, $t_2$.

Still referring to FIG. 8, in the second example, the third sheet 780 and the fourth sheet 790, positioned posterior to the patient 730, are optionally integrated into the tomography system 700, but are illustrated as a separate sheets. Signal derived from the third sheet 780, such as at point D, is optionally combined with signal from the fourth sheet 790 and/or signal from the tomography system 700 to yield a first vector, $v_{1b}$, from point $C_2$ to point D and/or from point D to point E of the charged particle beam posterior to the patient 730 at the first time, $t_1$, and a second vector, $v_{2a}$, such as from point H to point I of the charged particle beam posterior to the sample at a second time, $t_2$. Signal derived from the third sheet 780 and/or from the fourth sheet 790 and the corresponding first vector at the second time, $t_2$, is used to determine an output point, $C_2$, which may and often does differ from an extension of the first vector, $v_{1a}$, from point A to point B through the patient to a non-scattered beam path of point $C_1$. The difference between point $C_1$ and point $C_2$ and/or an angle, $\alpha$, between the first vector at the first time, $v_{1a}$, and the first vector at the second time, $v_{1b}$, is used to determine/map/identify, such as via tomographic analysis, internal structure of the patient 730, sample, and/or the tumor 720, especially when combined with scanning the charged particle beam in the x/y-plane as a function of time, such as illustrated by the second vector at the first time, $v_{2a}$, and the second vector at the second time, $v_{2b}$, forming angle $\beta$ and/or with rotation of the patient 730, such as about the y-axis, as a function of time.

Still referring to FIG. 8, multiple detectors/detector arrays are illustrated for detection of signals from multiple sheets, respectively. However, a single detector/detector array is optionally used to detect signals from multiple sheets, as further described infra. As illustrated, a set of detectors 810 is illustrated, including a second detector 814 imaging the second sheet 770, a third detector 816 imaging the third sheet 780, and a fourth detector 818 imaging the fourth sheet 790. Any of the detectors described herein are optionally detector arrays, are optionally coupled with any optical filter, and/or optionally use one or more intervening optics to image any of the four sheets 760, 770, 780, 790. Further, two or more detectors optionally image a single sheet, such as a region of the sheet, to aid optical coupling, such as F-number optical coupling.

Still referring to FIG. 8, a vector of the charged particle beam is determined. Particularly, in the illustrated example, the third detector 816, determines, via detection of secondary emitted photons, that the charged particle beam transmitted through point D and the fourth detector 818 determines that the charged particle beam transmitted through point E, where points D and E are used to determine the first vector at the second time, $v_{1b}$, as described supra. To increase accuracy and precision of a determined vector of the charged particle beam, a first determined beam position and a second determined beam position are optionally and preferably separated by a distance, $d_1$, such as greater than 0.1, 0.5, 1, 2, 3, 5, 10, or more centimeters. A support element 752 is illustrated that optionally connects any two or more elements of the charged particle beam state determination system 750 to each other and/or to any element of the charged particle beam system 100, such as a rotating platform 756 used to co-rotate the patient 730 and any element of the tomography system 700.

Example III

Still referring to FIG. 9A, a third example of the charged particle beam state determination system 750 is illustrated in an integrated tomography-cancer therapy system 900.

Referring to FIG. 9A, multiple sheets and multiple detectors are illustrated determining a charged particle beam state prior to the patient 730. As illustrated, a first camera 812 spatially images photons emitted from the first sheet 760 at point A, resultant from energy transfer from the passing charged particle beam, to yield a first signal and a second camera 814 spatially images photons emitted from the second sheet 770 at point B, resultant from energy transfer from the passing charged particle beam, to yield a second signal. The first and second signals allow calculation of the first vector, $v_{1a}$, with a subsequent determination of an entry point 732 of the charged particle beam into the patient 730. Determination of the first vector, $v_{1a}$, is optionally supplemented with information derived from states of the magnetic fields about the first axis control 143, the vertical control, and the second axis control 144, the horizontal axis control, as described supra.

Still referring to FIG. 9A, the charged particle beam state determination system is illustrated with multiple resolvable wavelengths of light emitted as a result of the charged particle beam transmitting through more than one molecule type, light emission center, and/or fluorophore type. For clarity of presentation and without loss of generality a first fluorophore in the third sheet 780 is illustrated as emitting blue light, b, and a second fluorophore in the fourth sheet 790 is illustrated as emitting red light, r, that are both detected by the third detector 816. The third detector is optionally coupled with any wavelength separation device, such as an optical filter, grating, or Fourier transform device. For clarity of presentation, the system is described with the red light passing through a red transmission filter blocking blue light and the blue light passing through a blue transmission filter blocking red light. Wavelength separation, using any means, allows one detector to detect a position of the charged particle beam resultant in a first secondary emission at a first wavelength, such as at point C, and a second secondary emission at a second wavelength, such as at point D. By extension, with appropriate optics, one camera is optionally used to image multiple sheets and/or sheets both prior to and posterior to the sample. Spatial determination of origin of the red light and the blue light allow calculation of the first vector at the second time, $v_{1b}$, and an actual exit point 736 from the patient 730 as compared to a non-scattered exit point 734 from the patient 730 as determined from the first vector at the first time, $v_{1a}$.

Figure 9B:
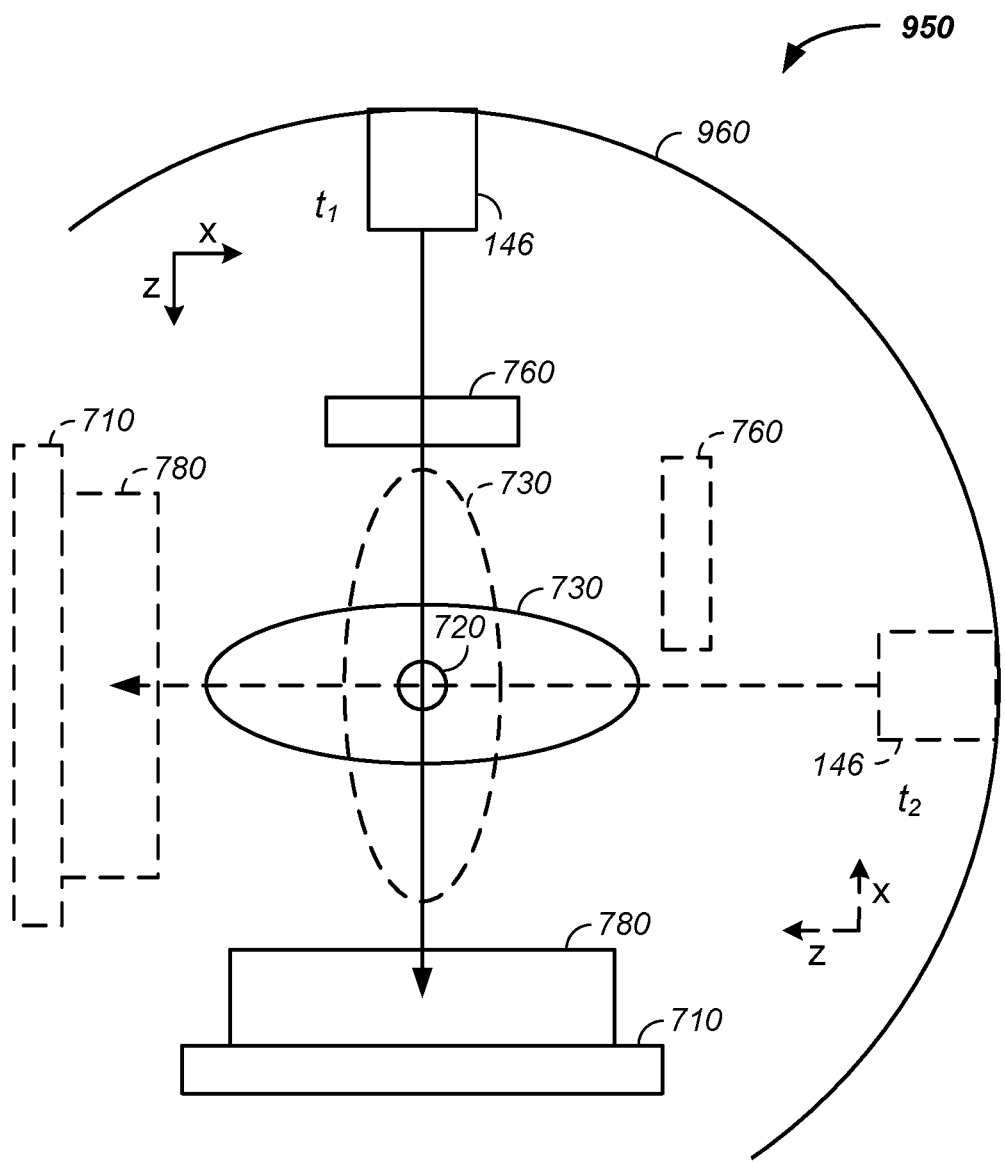

Still referring to FIG. 9A and referring now to FIG. 9B, the integrated tomography-cancer therapy system 900 is illustrated with an optional configuration of elements of the charged particle beam state determination system 750 being co-rotatable with the nozzle system 146 of the cancer therapy system 100. More particularly, in one case sheets of the charged particle beam state determination system 750 positioned prior to, posterior to, or on both sides of the patient 730 co-rotate with the scintillation material 710 about any axis, such as illustrated with rotation about the y-axis. Further, any element of the charged particle beam state determination system 750, such as a detector, two-dimensional detector, multiple two-dimensional detectors, and/or light coupling optic move as the gantry moves, such as along a common arc of movement of the nozzle system 146 and/or at a fixed distance to the common arc. For instance, as the gantry moves, a monitoring camera positioned on the opposite side of the tumor 720 or patient 730 from the nozzle system 146 maintains a position on the opposite side of the tumor 720 or patient 730. In various cases, co-rotation is achieved by co-rotation of the gantry of the charged particle beam system and a support of the patient, such as the rotatable platform 756, which is also referred to herein as a movable or dynamically positionable patient platform, patient chair, or patient couch. Mechanical elements, such as the support element 752 affix the various elements of the charged particle beam state determination system 750 relative to each other, relative to the nozzle system 146, and/or relative to the patient 730. For example, the support elements 752 maintain a second distance, $d_2$, between a position of the tumor 720 and the third sheet 780 and/or maintain a third distance, $d_3$, between a position of the third sheet 780 and the scintillation material 710. More generally, support elements 752 optionally dynamically position any element about the patient 730 relative to one another or in x,y,z-space in a patient diagnostic/treatment room, such as via computer control.

Referring now to FIG. 9B, positioning the nozzle system 146 of a gantry 960 on an opposite side of the patient 730 from a detection surface, such as the scintillation material 710, in a gantry movement system 950 is described. Generally, in the gantry movement system 950, as the gantry 960 rotates about an axis the nozzle/nozzle system 146 and/or one or more magnets of the beam transport system 135 are repositioned. As illustrated, the nozzle system 146 is positioned by the gantry 960 in a first position at a first time, $t_1$, and in a second position at a second time, $t_2$, where n positions are optionally possible. An electromechanical system, such as a patient table, patient couch, patient couch, patient rotation device, and/or a scintillation plate holder maintains the patient 730 between the nozzle system 146 and the scintillation material 710 of the tomography system 700. Similarly, not illustrated for clarity of presentation, the electromechanical system maintains a position of the third sheet 780 and/or a position of the fourth sheet 790 on a posterior or opposite side of the patient 730 from the nozzle 1 system 46 as the gantry 960 rotates or moves the nozzle system 146. Similarly, the electromechanical system maintains a position of the first sheet 760 or first screen and/or a position of the second sheet 770 or second screen on a same or prior side of the patient 730 from the nozzle system 146 as the gantry 960 rotates or moves the nozzle system 146. As illustrated, the electromechanical system optionally positions the first sheet 760 in the positively charged particle path at the first time, $t_1$, and rotates, pivots, and/or slides the first sheet 760 out of the positively charged particle path at the second time, $t_2$. The electromechanical system is optionally and preferably connected to the main controller 110 and/or the treatment delivery control system 112. The electromechanical system optionally maintains a fixed distance between: (1) the patient and the nozzle system 146 or the nozzle end 612, (2) the patient 730 or tumor 720 and the scintillation material 710, and/or (3) the nozzle system 146 and the scintillation material 710 at a first treatment time with the gantry 960 in a first position and at a second treatment time with the gantry 960 in a second position. Use of a common charged particle beam path for both imaging and cancer treatment and/or maintaining known or fixed distances between beam transport/guide elements and treatment and/or detection surface enhances precision and/or accuracy of a resultant image and/or tumor treatment, such as described supra.

System Integration

Any of the systems and/or elements described herein are optionally integrated together and/or are optionally integrated with known systems.

Treatment Delivery Control System

Referring now to FIG. 10, a centralized charged particle treatment system 1000 is illustrated. Generally, once a charged particle therapy plan is devised, a central control system or treatment delivery control system 112 is used to control sub-systems while reducing and/or eliminating direct communication between major subsystems. Generally, the treatment delivery control system 112 is used to directly control multiple subsystems of the cancer therapy system without direct communication between selected subsystems, which enhances safety, simplifies quality assurance and quality control, and facilitates programming. For example, the treatment delivery control system 112 directly controls one or more of: an imaging system, a positioning system, an injection system, a radio-frequency quadrupole system, a linear accelerator, a ring accelerator or synchrotron, an extraction system, a beam line, an irradiation nozzle, a gantry, a display system, a targeting system, and a verification system. Generally, the control system integrates sub-systems and/or integrates output of one or more of the above described cancer therapy system elements with inputs of one or more of the above described cancer therapy system elements.

Still referring to FIG. 10, an example of the centralized charged particle treatment system 1000 is provided. Initially, a doctor, such as an oncologist, prescribes 1010 or recommends tumor therapy using charged particles. Subsequently, treatment planning 1020 is initiated and output of the treatment planning step 1020 is sent to an oncology information system 1030 and/or is directly sent to the treatment delivery system 112, which is an example of the main controller 110.

Still referring to FIG. 10, the treatment planning step 1020 is further described. Generally, radiation treatment planning is a process where a team of oncologist, radiation therapists, medical physicists, and/or medical dosimetrists plan appropriate charged particle treatment of a cancer in a patient. Typically, one or more imaging systems 170 are used to image the tumor and/or the patient, described infra. Planning is optionally: (1) forward planning and/or (2) inverse planning. Cancer therapy plans are optionally assessed with the aid of a dose-volume histogram, which allows the clinician to evaluate the uniformity of the dose to the tumor and surrounding healthy structures. Typically, treatment planning is almost entirely computer based using patient computed tomography data sets using multimodality image matching, image coregistration, or fusion.

Forward Planning

In forward planning, a treatment oncologist places beams into a radiotherapy treatment planning system including: how many radiation beams to use and which angles to deliver each of the beams from. This type of planning is used for relatively simple cases where the tumor has a simple shape and is not near any critical organs.

Inverse Planning

In inverse planning, a radiation oncologist defines a patient's critical organs and tumor and gives target doses and importance factors for each. Subsequently, an optimization program is run to find the treatment plan which best matches all of the input criteria.

Oncology Information System

Still referring to FIG. 10, the oncology information system 1030 is further described. Generally, the oncology information system 1030 is one or more of: (1) an oncology-specific electronic medical record, which manages clinical, financial, and administrative processes in medical, radiation, and surgical oncology departments; (2) a comprehensive information and image management system; and (3) a complete patient information management system that centralizes patient data; and (4) a treatment plan provided to the charged particle beam system 100, main controller 110, and/or the treatment delivery control system 112. Generally, the oncology information system 1030 interfaces with commercial charged particle treatment systems.

Safety System/Treatment Delivery Control System

Still referring to FIG. 10, the treatment delivery control system 112 is further described. Generally, the treatment delivery control system 112 receives treatment input, such as a charged particle cancer treatment plan from the treatment planning step 1020 and/or from the oncology information system 1030 and uses the treatment input and/or treatment plan to control one or more subsystems of the charged particle beam system 100. The treatment delivery control system 112 is an example of the main controller 110, where the treatment delivery control system receives subsystem input from a first subsystem of the charged particle beam system 100 and provides to a second subsystem of the charged particle beam system 100: (1) the received subsystem input directly, (2) a processed version of the received subsystem input, and/or (3) a command, such as used to fulfill requisites of the treatment planning step 1020 or direction of the oncology information system 1030. Generally, most or all of the communication between subsystems of the charged particle beam system 100 go to and from the treatment delivery control system 112 and not directly to another subsystem of the charged particle beam system 100. Use of a logically centralized treatment delivery control system has many benefits, including: (1) a single centralized code to maintain, debug, secure, update, and to perform checks on, such as quality assurance and quality control checks; (2) a controlled logical flow of information between subsystems; (3) an ability to replace a subsystem with only one interfacing code revision; (4) room security; (5) software access control; (6) a single centralized control for safety monitoring; and (7) that the centralized code results in an integrated safety system 1040 encompassing a majority or all of the subsystems of the charged particle beam system 100.

Examples of subsystems of the charged particle cancer therapy system 100 include: a radio frequency quadrupole 1050, a radio frequency quadrupole linear accelerator, the injection system 120, the synchrotron 130, the accelerator system 131, the extraction system 134, any controllable or monitorable element of the beam line 268, the targeting/delivery system 140, the nozzle system 146, a gantry 1060 or an element of the gantry 1060, the patient interface module 150, a patient positioner 152, the display system 160, the imaging system 170, a patient position verification system 179, any element described supra, and/or any subsystem element. A treatment change 1070 at time of treatment is optionally computer generated with or without the aid of a technician or physician and approved while the patient is still in the treatment room, in the treatment chair, and/or in a treatment position.

Safety

Figure 11:
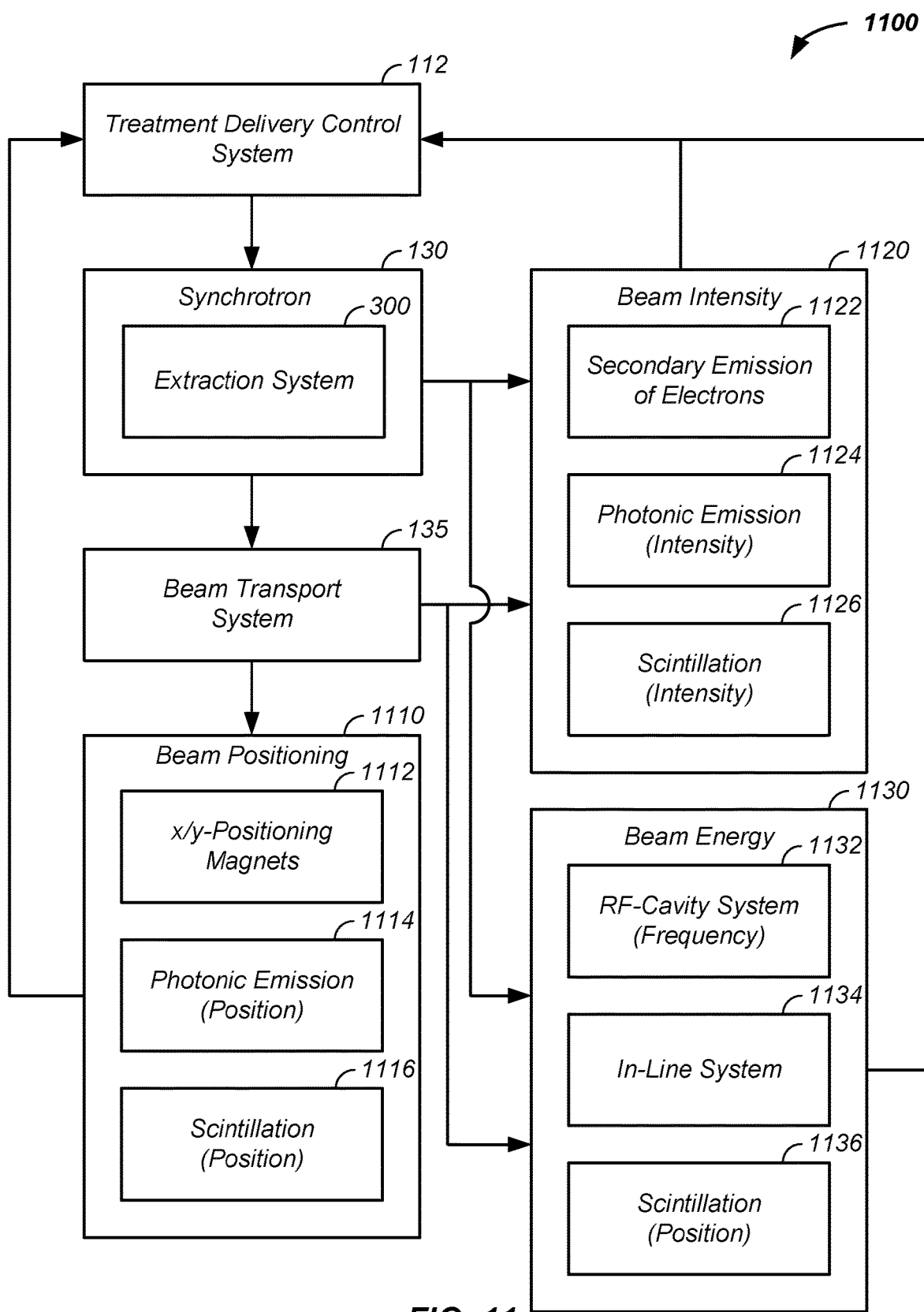
FIG. 11 illustrates beam state determination systems.

Referring now to FIG. 11, a redundant safety system 1100 is described. In one optional and preferred embodiment, the charged particle beam system 100 includes redundant systems for determination of one or more of: (1) beam position, (2) beam direction, (3) beam intensity, (4) beam energy, and (5) beam shape. The redundant safety system 1000 is further described herein.

Beam Position

A beam positioning system 1110 or beam position determination/verification system is linked to the main controller 100 or treatment delivery control system 112. The beam positioning system 1110 includes any electromechanical system, optical system, and/or calculation for determining a current position of the charged particle beam. In a first case, after calibration, the scanning/targeting/delivery system 140 uses x/y-positioning magnets, such as in the first axis control 143 and the second axis control 144, to position the charged particle beam. In a second case, a photonic emission position system 1114 is used to measure a position of the charged particle beam, where the photonic emission system 1114 uses a secondary emission of a photon upon passage of the charged particle beam, such as described supra for the first sheet 760, the second sheet 770, the third sheet 780, and the fourth sheet 790. In a third case, a scintillation positioning system 1116, such as via use of a detector element in the tomography system 700, is used to measure a position of the charged particle beam. Any permutation or combination of the three cases described herein yield multiple or redundant measures of the charged particle beam position and therefrom one or more measures of a charged particle beam vector during a period of time.

Beam Intensity

A beam intensity system 1120 or beam intensity determination/verification system is linked to the main controller 100 or treatment delivery control system 112. Herein, intensity is a number of positively charged particles passing a point or plane as a function of time. The beam intensity system 1110 includes any electromechanical system, optical system, and/or calculation for determining a current intensity of the charged particle beam. In a first case, the extraction system 134 uses an electron emission system 1122, such as a secondary emission of electrons upon passage of the charged particle beam through the extraction material 330, to determine an intensity of the charged particle beam. In a second case, the duration of the applied RF-field and/or a magnitude of the RF-field applied in the RF-cavity system 310 is used to calculate the intensity of the charged particle beam, as described supra. In a third case, a photon emission system 1124, such as a magnitude of a signal representing the emitted photons from the photonic emission system 1114, is used to measure the intensity of the charged particle beam. In a fourth case, a scintillation intensity determination system 1126 measures the intensity of the charged particle beam, such as with a detector of the tomography system 700.

Beam Energy

A beam energy system 1130 or beam energy determination/verification system is linked to the main controller 100 or treatment delivery control system 112. Herein, energy is optionally referred to as a velocity of the positively charged particles passing a point, where energy is dependent upon mass of the charged particles. The beam energy system 1110 includes any electromechanical system, optical system, and/or calculation for determining a current energy of the charged particle beam. In a first case, an RF-cavity energy system 1132 calculates an energy of the charged particles in the charged particle beam, such as via relating a period of an applied RF-field in the RF-cavity system 310 to energy, such as described supra. In a second case, an in-line energy system 1134 is used to measure a value related to beam energy, such as described above in equations 1 and 2. In a third case, a scintillation energy system 1136 is used to measure an energy of the charged particle beam, such as via use of a detector in the tomography system 700.

Optionally and preferably, two or more measures/determination/calculations of a beam state property, such as position, direction, shape, intensity, and/or energy yield a redundant measure of the measured state for use in a beam safety system and/or an emergency beam shut-off system. Optionally and preferably, the two or more measures of a beam state property are used to enhance precision and/or accuracy of determination of the beam state property through statistical means. Optionally and preferably, any of the beam state properties are recorded and/or used to predict a future state, such as position, intensity, and/or energy of the charged particle beam, such as in a neighboring voxel in the tumor 720 adjacent to a currently treated voxel in the tumor 720 of the patient 730.

Motion Control System

Figure 12A:
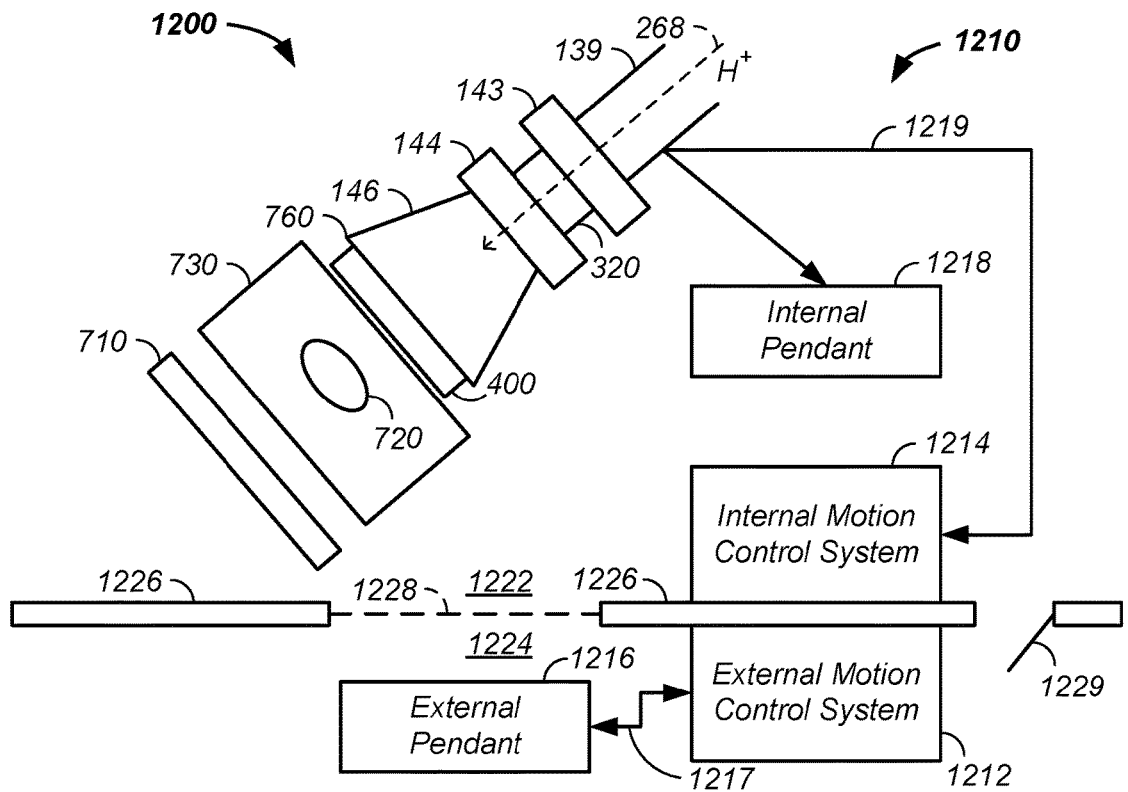
FIG. 12A and FIG. 12B illustrate control of a patient interface system with a pendant and work-flow control system, respectively.

Referring now to FIG. 12A, a motion control system 1200 is illustrated. Generally, the motion control system controls, as a function of time: (1) the charged particle beam state, such as direction, shape, intensity, and/or energy; (2) a patient position; and/or (3) an imaging system. The motion control system 1200 is further described herein.

The motion control system 1200 optionally uses one or more patient interface controllers 1210, such as an external motion control system 1212, an internal motion control system 1214, an external pendant 1216, and an internal pendant 1218. As illustrated, the patient 730 is in a treatment room 1222 separated from a control room 1224 by a radiation shielded wall 1226 and a window 1228 or view port. The external motion control system 1212, internal motion control system 1214, external pendant 1216, and the internal pendant 1218 optionally and preferably control the same elements, allowing one or more operators control of the motion control system. Any of the patient interface controllers 1210 are optionally linked to each other or to the main controller 110 via wireless means; however, interconnections of the patient interface controllers 1210 to each other and/or to the main controller 110 are preferably hard-wired due to high radiation levels in the treatment room 1222. For example, the external pendant 1216 is linked via a first communication bundle 1217 to the external motion control system 1212, the internal pendant 1218 is linked via a second communication bundle 1219 to the internal motion system controller 1214, and/or the internal and external motion control system 1212, 1214 are hardwired to each other and/or to the main controller 110. The first communication bundle 1217 and the second communication bundle 1219 optionally provide power to the external pendant 1216 and the internal pendant 1218, respectively. The second communication bundle 1219 is optionally attached and/or linked to the nozzle system 146 and/or an element of the beam transport system 135 to keep the second communication bundle: (1) accessible to the operator, (2) out of the way of the charged particle beam, and/or (3) out of the way of motion of the patient 730/patient interface module 150. Optionally, a patient specific treatment module 1290 is replaceably plugged into and/or attached to the one or more patient interface controllers 1210, such as the internal pendant 1218. The patient treatment module 1290 optionally contains one or more of: image information about the individual being treated and/or preprogrammed treatment steps for the individual being treated, where some controls of the charged particle beam system 100, such as related to charged particle beam aiming and/or patient positioning are optionally limited by the preprogrammed treatment steps of any information/hardware of the patient treatment module. Optionally, the internal pendant 1218 replaceably mounts to a bracket, hook, slot, or the like mounted on the nozzle system 146 or the beam transport system 135 to maintain close access for the operator when not in use. The operator optionally and preferably uses, at times, a mobile control pendant, such as the external pendant 1216 or the internal pendant 1218. The operator optionally has access via a direct doorway 1229 between treatment room 1222 and the control room 1224. Use of multiple patient interface controllers 1210 gives flexibility to an operator of the motion control system 1200, as further described infra.

Example I

In a first example, the operator of the motion control system 1200 is optionally seated or standing by a fixed position controller, such as by a desktop or wall mounted version of the external motion control system 1212. Similarly, the internal motion control system 1214 is optionally and preferably in a fixed position, such as at a desktop system or wall mounted system.

Example II

In a second example, the operator optionally and preferably uses, at times, the external pendant 1216, which allows the operator to view the patient 730, the beam transport system 135, beam path housing 139, the patient interface module 150, and/or the imaging system 170 through the safety of the window 1228. Optionally and preferably, the beam transport system 135 is configured with one or more mechanical stops to not allow the charged particle beam to aim at the window 1228, thereby providing a continuously safe zone for the operator. Direct viewing and control of the charged particle beam system 100, imaging system 170, and/or tomography system 700 relative to the current position of the patient 730 allows backup security in terms of unexpected aim of a treatment beam and/or movement of the patient 730. Controlled elements and/or processes of the charged particle beam system 100 via the pendants is further described, infra.

Example III

In a third example, the operator optionally and preferably uses, at times, the internal pendant 1218, which allows the operator both direct access and view of: (1) the patient 730, (2) the beam transport system 135, (3) the patient interface module 150, and/or (4) the imaging system 170, which has multiple benefits. In a first case, the operator can adjust any element of the patient interface module 150, such as a patient positioning device and/or patient motion constraint device. In a second case, the operator has access to load/unload: (1) the patient specific tray insert 510 into the beam control tray assembly 400; (2) the beam control tray assembly 400 into the nozzle system 146, as described supra; and/or (3) any imaging material, such as an X-ray film.

Example IV

In a fourth example, the gantry comprises at least two imaging devices, where each imaging device moves with rotation of the gantry and where the two imaging devices view the patient 730 along two axes forming an angle of ninety degrees, in the range of eighty-five to ninety-five degrees, and/or in the range of seventy-five to one hundred five degrees.

Pendant

Figure 12B:
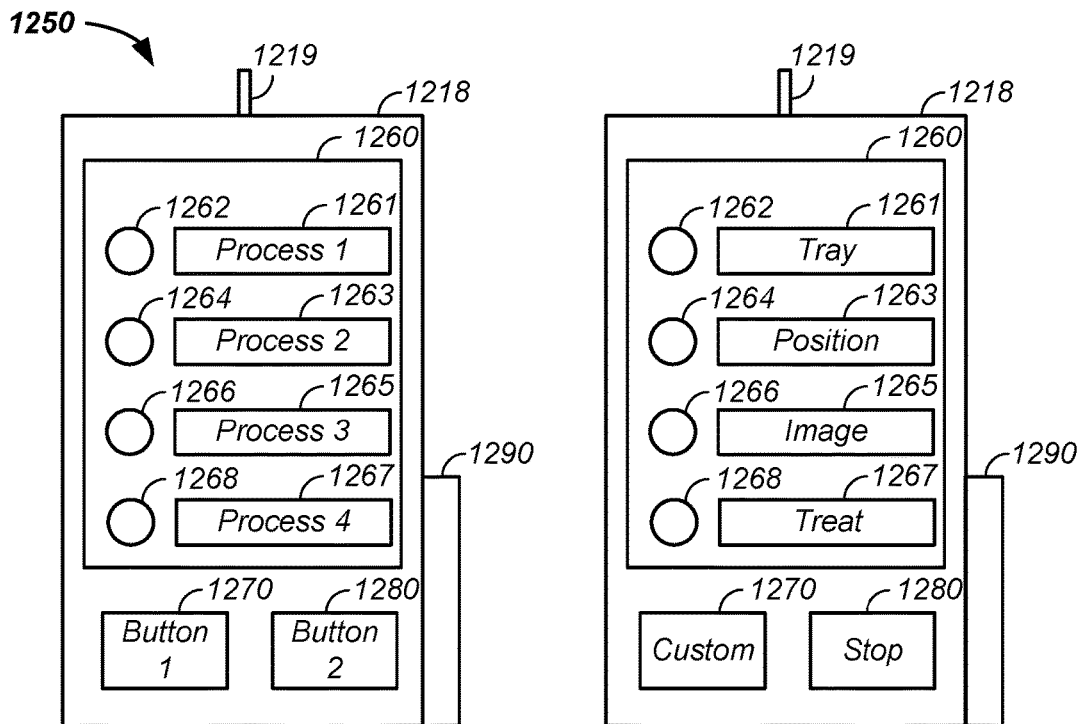

Referring still to FIG. 12A and referring now to FIG. 12B, a pendant system 1250, such as a system using the external pendant 1216 and/or internal pendent 1218 is described. In a first case, the external pendant 1216 and internal pendant 1218 have identical controls. In a second case, controls and/or functions of the external pendant 1216 intersect with controls and/or function of the internal pendant 1218. Particular processes and functions of the internal pendant 1218 are provided below, without loss of generality, to facilitate description of the external and internal pendants 1216, 1218. The internal pendant 1218 optionally comprises any number of input buttons, screens, tabs, switches, or the like. The pendant system 1250 is further described, infra.

Example I

Referring now to FIG. 12B, a first example of the internal pendant 1218 is provided. In this example, in place of and/or in conjunction with a particular button, such as a first button 1270 and/or a second button 1280, moving or selecting a particular element, processes are optionally described, displayed, and/or selected within a flow process control unit 1260 of the internal pendant 1218. For example, one or more display screens and/or printed elements describe a set of processes, such as a first process 1261, a second process 1263, a third process 1265, and a fourth process 1267 and are selected through a touch screen selection process or via a selection button, such as a corresponding first selector 1262, second selector 1264, third selector 1266, and fourth selector 1268. Optionally, a next button a-priori or previously scheduled in treatment planning to select a next process is lit up on the pendant.

Example II

Referring still to FIG. 12B, a second example of the internal pendant 1218 is provided. In this example, one or more buttons or the like, such as the first button 1270, and/or one or more of the processes, such as the first process 1261, are customizable, such as to an often repeated set of steps and/or to steps particular to treatment of a given patient 730. The customizable element, such as the first button 1270, is optionally further setup, programmed, controlled, and/or limited via information received from the patient treatment module 1290. In this example, a button, or the like, operates as an emergency all stop button, which at the minimum shuts down the accelerator, redirects the charged particle beam to a beam stop separate from a path through the patient, or stops moving the patient 730.

Example III

In place of and/or in conjunction with a particular button, such as the first button 1270 and/or the second button 1280, moving or selecting a particular element, processes are optionally described, displayed, and/or selected within a flow process control unit 1260 of the internal pendant 1218. For example, one or more display screens and/or printed elements describe a set of processes, such as a first process 1261, a second process 1263, a third process 1265, and a fourth process 1267 and are selected through a touch screen selection process or via a selection button, such as a corresponding first selector 1262, second selector 1264, third selector 1266, and fourth selector 1268.

Referring still to FIG. 12B, as illustrated for clarity and without loss or generalization, the first process 1261 and/or a display screen thereof operable by the first selector 1262 selects, initiates, and/or processes a set of steps related to the beam control tray assembly 400. For instance, the first selector 1262, functioning as a tray button: (1) confirms presence a requested patient specific tray insert 510 in a requested tray assembly; (2) confirms presence of a request patient specific tray insert in a receiving slot of the control tray assembly; (3) retracts the beam control tray assembly 400 into the nozzle system 146; (4) confirms information using the electromechanical identifier plug, such as the first electromechanical identifier plug 530; (5) confirms information using the patient treatment module 1290; and/or (6) performs a set of commands and/or movements identified with the first selector 1262 and/or identified with the first process 1261. Similarly, the second process 1263, corresponding to a second process display screen and/or the second selector 1264; the third process 1265, corresponding to a third process display screen and/or the third selector 1266; and the fourth process 1267, corresponding to a fourth process display screen and/or the fourth selector 1268 control and/or activate a set of actions, movements, and/or commands related to positioning the patient 730, imaging the patient 730, and treating the patient 730, respectively.

Integrated Cancer Treatment—Imaging System

One or more imaging systems 170 are optionally used in a fixed position in a cancer treatment room and/or are moved with a gantry system, such as a gantry system supporting: a portion of the beam transport system 135, the targeting/delivery control system 140, and/or moving or rotating around a patient positioning system, such as in the patient interface module. Without loss of generality and to facilitate description of the invention, examples follow of an integrated cancer treatment—imaging system. In each system, the beam transport system 135 and/or the nozzle system 146 indicates a positively charged beam path, such as from the synchrotron, for tumor treatment and/or for tomography, as described supra.

Example I

Figure 13A:
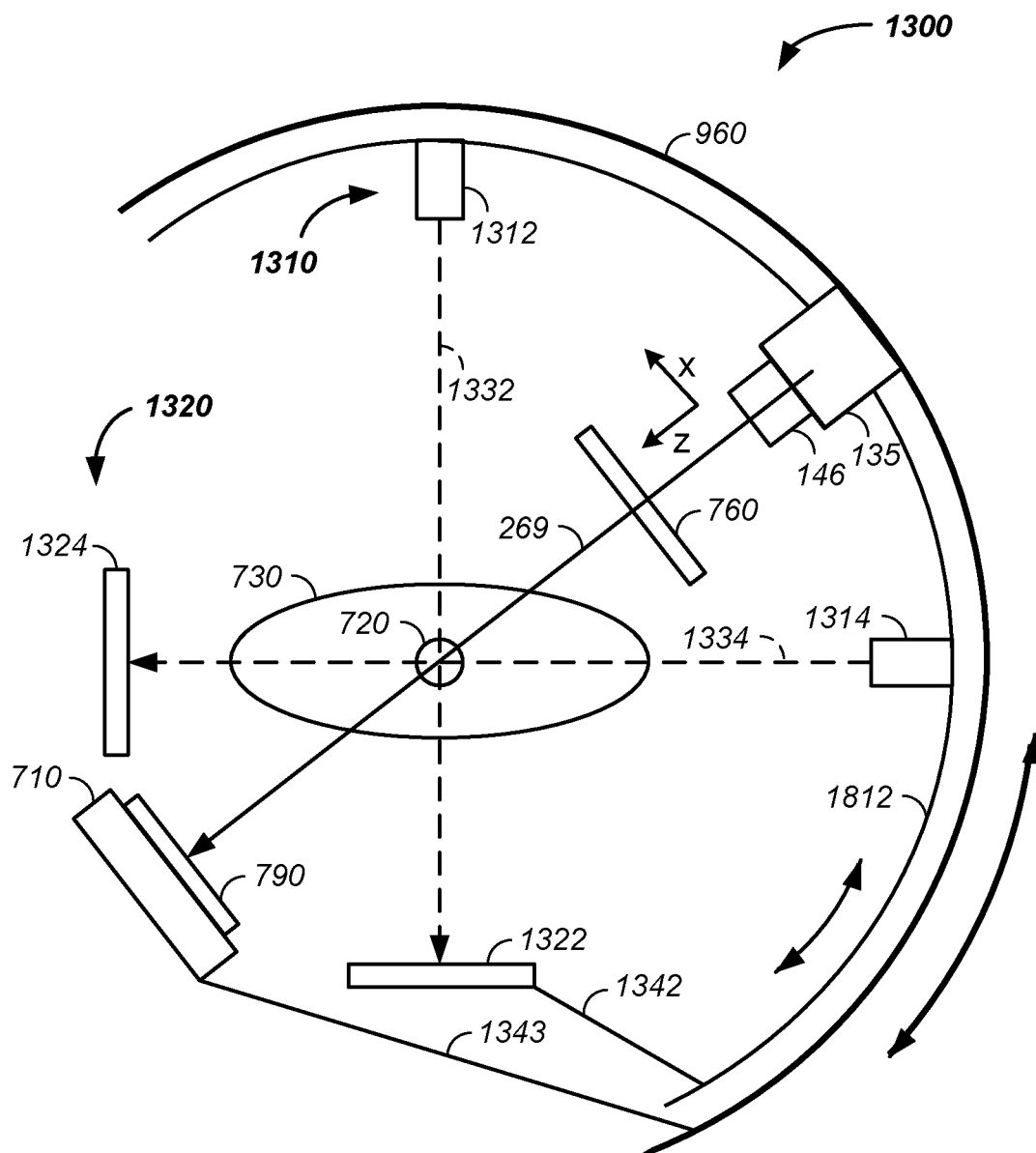
FIG. 13A illustrates a two-dimensional—two-dimensional imaging system relative to a cancer treatment beam.

Referring now to FIG. 13A, a first example of an integrated cancer treatment—imaging system 1300 is illustrated. In this example, the charged particle beam system 100 is illustrated with a treatment beam 269 directed to the tumor 720 of the patient 730 along the z-axis. Also illustrated is a set of imaging sources 1310, imaging system elements, and/or paths therefrom and a set of detectors 1320 corresponding to a respective element of the set of imaging sources 1310. Herein, the set of imaging sources 1310 are referred to as sources, but are optionally any point or element of the beam train prior to the tumor or a center point about which the gantry rotates. Hence, a given imaging source is optionally a dispersion element used to form cone beam. As illustrated, a first imaging source 1312 yields a first beam path 1332 and a second imaging source 1314 yields a second beam path 1334, where each path passes at least into the tumor 720 and optionally and preferably to a first detector array 1322 and a second detector array 1324, respectively, of the set of detectors 1320. Herein, the first beam path 1332 and the second beam path 1334 are illustrated as forming a ninety degree angle, which yields complementary images of the tumor 720 and/or the patient 730. However, the formed angle is optionally any angle from ten to three hundred fifty degrees. Herein, for clarity of presentation, the first beam path 1332 and the second beam path 1334 are illustrated as single lines, which optionally is an expanding, uniform diameter, or focusing beam. Herein, the first beam path 1332 and the second beam path 1334 are illustrated in transmission mode with their respective sources and detectors on opposite sides of the patient 730. However, a beam path from a source to a detector is optionally a scattered path and/or a diffuse reflectance path. Optionally, one or more detectors of the set of detectors 1320 are a single detector element, a line of detector elements, or preferably a two-dimensional detector array. Use of two two-dimensional detector arrays is referred to herein as a two-dimensional—two-dimensional imaging system or a 2D-2D imaging system.

Still referring to FIG. 13A, the first imaging source 1312 and the second imaging source 1314 are illustrated at a first position and a second position, respectively. Each of the first imaging source 1312 and the second imaging source 1322 optionally: (1) maintain a fixed position; (2) provide the first beam path(s) 1332 and the second beam path(s) 1334, respectively, such as to an imaging system detector 1340 or through the gantry 960, such as through a set of one or more holes or slits; (3) provide the first beam path 1332 and the second beam path 1334, respectively, off axis to a plane of movement of the nozzle system 146; (4) move with the gantry 960 as the gantry 960 rotates about at least a first axis; (5) move with a secondary imaging system independent of movement of the gantry, as described supra; and/or (6) represent a narrow cross-diameter section of an expanding cone beam path.

Figure 13B:
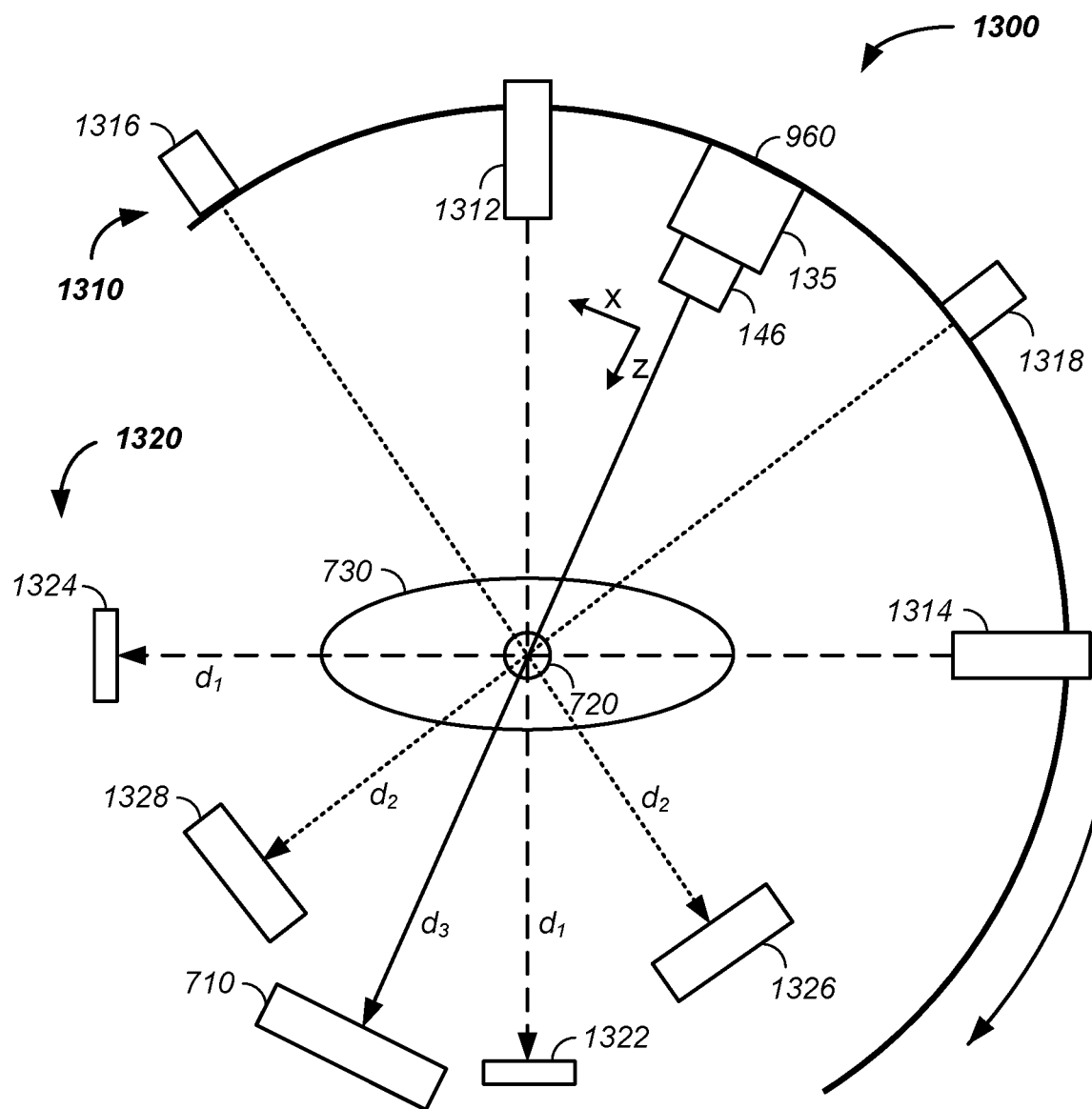
FIG. 13B illustrates multiple gantry supported imaging systems.

Still referring to FIG. 13A, the set of detectors 1320 are illustrated as coupling with respective elements of the set of sources 1310. Each member of the set of detectors 1320 optionally and preferably co-moves/and/or co-rotates with a respective member of the set of sources 1310. Thus, if the first imaging source 1312 is statically positioned, then the first detector 1322 is optionally and preferably statically positioned. Similarly, to facilitate imaging, if the first imaging source 1312 moves along a first arc as the gantry 960 moves, then the first detector 1322 optionally and preferably moves along the first arc or a second arc as the gantry 960 moves, where relative positions of the first imaging source 1312 on the first arc, a point that the gantry 960 moves about, and relative positions of the first detector 1322 along the second arc are constant. To facilitate the process, the detectors are optionally mechanically linked, such as with a mechanical support to the gantry 960 in a manner that when the gantry 960 moves, the gantry moves both the source and the corresponding detector. Optionally, the source moves and a series of detectors, such as along the second arc, capture a set of images. As illustrated in FIG. 13A, the first imaging source 1312, the first detector array 1322, the second imaging source 1314, and the second detector array 1324 are coupled to a rotatable imaging system support 1812, which optionally rotates independently of the gantry 960 as further described infra. As illustrated in FIG. 13B, the first imaging source 1312, the first detector array 1322, the second imaging source 1314, and the second detector array 1324 are coupled to the gantry 960, which in this case is a rotatable gantry.

Still referring to FIG. 13A, optionally and preferably, elements of the set of sources 1310 combined with elements of the set of detectors 1320 are used to collect a series of responses, such as one source and one detector yielding a detected intensity and rotatable imaging system support 1812 preferably a set of detected intensities to form an image. For instance, the first imaging source 1312, such as a first X-ray source or first cone beam X-ray source, and the first detector 1322, such as an X-ray film, digital X-ray detector, or two-dimensional detector, yield a first X-ray image of the patient at a first time and a second X-ray image of the patient at a second time, such as to confirm a maintained location of a tumor or after movement of the gantry and/or nozzle system 146 or rotation of the patient 730. A set of n images using the first imaging source 1312 and the first detector 1322 collected as a function of movement of the gantry and/or the nozzle system 146 supported by the gantry and/or as a function of movement and/or rotation of the patient 730 are optionally and preferably combined to yield a three-dimensional image of the patient 730, such as a three-dimensional X-ray image of the patient 730, where n is a positive integer, such as greater than 1, 2, 3, 4, 5, 10, 15, 25, 50, or 100. The set of n images is optionally gathered as described in combination with images gathered using the second imaging source 1314, such as a second X-ray source or second cone beam X-ray source, and the second detector 1324, such as a second X-ray detector, where the use of two, or multiple, source/detector combinations are combined to yield images where the patient 730 has not moved between images as the two, or the multiple, images are optionally and preferably collected at the same time, such as with a difference in time of less than 0.01, 0.1, 1, or 5 seconds. Longer time differences are optionally used. Preferably the n two-dimensional images are collected as a function of rotation of the gantry 960 about the tumor and/or the patient and/or as a function of rotation of the patient 730 and the two-dimensional images of the X-ray cone beam are mathematically combined to form a three-dimensional image of the tumor 720 and/or the patient 730. Optionally, the first X-ray source and/or the second X-ray source is the source of X-rays that are divergent forming a cone through the tumor. A set of images collected as a function of rotation of the divergent X-ray cone around the tumor with a two-dimensional detector that detects the divergent X-rays transmitted through the tumor is used to form a three-dimensional X-ray of the tumor and of a portion of the patient, such as in X-ray computed tomography.

Still referring to FIG. 13A, use of two imaging sources and two detectors set at ninety degrees to one another allows the gantry 960 or the patient 730 to rotate through half an angle required using only one imaging source and detector combination. A third imaging source/detector combination allows the three imaging source/detector combination to be set at sixty degree intervals allowing the imaging time to be cut to that of one-third that gantry 960 or patient 730 rotation required using a single imaging source-detector combination. Generally, n source-detector combinations reduces the time and/or the rotation requirements to 1/n. Further reduction is possible if the patient 730 and the gantry 960 rotate in opposite directions. Generally, the used of multiple source-detector combination of a given technology allow for a gantry that need not rotate through as large of an angle, with dramatic engineering benefits.

Still referring to FIG. 13A, the set of sources 1310 and set of detectors 1320 optionally use more than one imaging technology. For example, a first imaging technology uses X-rays, a second used fluoroscopy, a third detects fluorescence, a fourth uses cone beam computed tomography or cone beam CT, and a fifth uses other electromagnetic waves. Optionally, the set of sources 1310 and the set of detectors 1320 use two or more sources and/or two or more detectors of a given imaging technology, such as described supra with two X-ray sources to n X-ray sources.

Still referring to FIG. 13A, use of one or more of the set of sources 1310 and use of one or more of the set of detectors 1320 is optionally coupled with use of the positively charged particle tomography system described supra. As illustrated in FIG. 13A, the positively charged particle tomography system uses a second mechanical support 1343 to co-rotate the scintillation material 710 with the gantry 960, as well as to co-rotate an optional sheet, such as the first sheet 760 and/or the fourth sheet 790.

Example II

Referring now to FIG. 13B, a second example of the integrated cancer treatment—imaging system 1300 is illustrated using greater than three imagers.

Still referring to FIG. 13B, two pairs of imaging systems are illustrated. Particularly, the first and second imaging source 1312, 1314 coupled to the first and second detectors 1322, 1324 are as described supra. For clarity of presentation and without loss of generality, the first and second imaging systems are referred to as a first X-ray imaging system and a second X-ray imaging system. The second pair of imaging systems uses a third imaging source 1316 coupled to a third detector 1326 and a fourth imaging source 1318 coupled to a fourth detector 1328 in a manner similar to the first and second imaging systems described in the previous example. Here, the second pair of imaging systems optionally and preferably uses a second imaging technology, such as fluoroscopy. Optionally, the second pair of imaging systems is a single unit, such as the third imaging source 1316 coupled to the third detector 1326, and not a pair of units. Optionally, one or more of the set of imaging sources 1310 are statically positioned while one of more of the set of imaging sources 1310 co-rotate with the gantry 960. Pairs of imaging sources/detector optionally have common and distinct distances, such as a first distance, $d_1$, such as for a first source-detector pair and a second distance, $d_2$, such as for a second source-detector or second source-detector pair. As illustrated, the tomography detector or the scintillation material 710 is at a third distance, $d_3$. The distinct differences allow the source-detector elements to rotate on a separate rotation system at a rate different from rotation of the gantry 960, which allows collection of a full three-dimensional image while tumor treatment is proceeding with the positively charged particles.

Example III

Figure 13C:
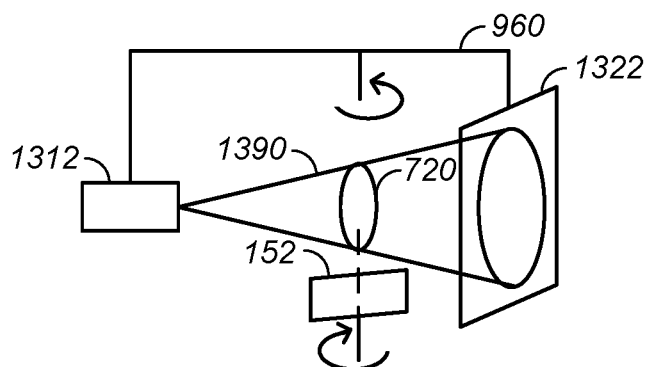
FIG. 13C illustrates a rotatable cone beam

For clarity of presentation, referring now to FIG. 13C, any of the beams or beam paths described herein is optionally a cone beam 1390 as illustrated. The patient support 152 is an mechanical and/or electromechanical device used to position, rotate, and/or constrain any portion of the tumor 720 and/or the patient 730 relative to any axis.

Tomography Detector System

A tomography system optically couples the scintillation material to a detector. As described, supra, the tomography system optionally and preferably uses one or more detection sheets, beam tracking elements, and/or tracking detectors to determine/monitor the charged particle beam position, shape, and/or direction in the beam path prior to and/or posterior to the sample, imaged element, patient, or tumor. Herein, without loss of generality, the detector is described as a detector array or two-dimensional detector array positioned next to the scintillation material; however, the detector array is optionally optically coupled to the scintillation material using one or more optics. Optionally and preferably, the detector array is a component of an imaging system that images the scintillation material 710, where the imaging system resolves an origin volume or origin position on a viewing plane of the secondary photon emitted resultant from passage of the residual charged particle beam 267. As described, infra, more than one detector array is optionally used to image the scintillation material 710 from more than one direction, which aids in a three-dimensional reconstruction of the photonic point(s) of origin, positively charged particle beam path, and/or tomographic image.

Detector Array

Referring now to FIG. 14A, in a tomography system 1400, a detector array 1410 is optically coupled to the scintillation material 710. For clarity of presentation and without loss of generality, the detector array 1410, which is preferably a two-dimensional detector array, is illustrated with a detection side directly coupled to the scintillation material 710, such as through physical contact or through an intervening layer of an optical coupling material or optical coupling fluid with an index of refraction between that of the scintillation material 710 and front side of the detector array 1410. However, the detector array 1410 is optionally remotely located from the scintillation material 710 and coupled using light coupling optics. As illustrated, secondary photons emitted from the scintillation material 710, resultant from passage of the residual charge particle beam 267, strike a range of detector elements according to a probability distribution function. Generally, the positively charged particles from the accelerator after passing through the sample strike the scintillation material resultant in emitted electrons and photons, the photons are detected, and the path of the charged particles and/or the energy of the charged particles after passing through the sample is back calculated using the detection position(s) of the photons in the detector array.

Referring now to FIG. 14B, the tomography system 1400 is illustrated with an optical array between the scintillation material 710 and the detector array 1410. For clarity of presentation and without loss of generality, the optical array is referred to herein as a fiber optic array 1420, which is preferably a two-dimensional fiber optic array. The individual elements of the optical array are optionally of any geometry, such as a square or rectangular cross-section in place of a round cross-section of a fiber optic. Generally, the scintillation material 710 is optically coupled to the fiber optic array 1420 and the fiber optic array 1420 is optically coupled to the detector array 1410, which may be mass produced. In one case, elements of the fiber optic array 1420 couple 1:1 with elements of the detector array 1410. In a second preferable case, the intermediate fiber optic array 1420 is primarily used to determine position of detected photons and many detector elements of the detector array couple to a single fiber optic element of the fiber optic array 1420 or vice-versa. In the second case, signals from detector elements not aligned with a given fiber core, but instead aligned with a cladding or buffer material about the fiber are removed in post-processing.

Referring now to FIG. 14C and FIG. 14D, the fiber optic array 1420 is illustrated with a fiber array configuration that is close-packed 1422 and orderly 1424, respectively. The close-packed 1422 system captures a higher percentage of photons while the orderly 1424 system couples readily with an array of detector elements in the detector array 1424. Since post-processing is optionally and preferably used to determine which detector element signals to use, the packing structure of the fiber optic array 1420 is optionally of any geometry.

Referring now to FIG. 14E, the tomography system 1400 is illustrated with an optional micro-optic array 1412 coupling and focusing photons from the scintillation material 710 to the detector array 1410. Generally, the array of micro-optics couples more light to the detector elements of the detector array 1410, which increases the signal-to-noise ratio of the detected signals.

Multiplexed Scintillation

Referring now to FIG. 15, a multiplexed scintillation system 1500 is illustrated. In one case of the multiplexed scintillation system 1500, multiple frequencies of light are detected where the detected frequency wavelength, wavelength range, or color is representative of energy, or residual energy after passing through the sample, of the residual charged particle beam 267. In another case, changing distributions of secondary photons, resultant from passage of the residual charged particle beam 267, are detected and used to determine state of the residual charged particle beam 267, such as position, direction, intensity, and/or energy. In still another case, a set of different scintillation materials are used to determine state of the residual charged particle beam 267. To clarify and without loss of generality, several examples of multiplexed scintillation follow.

Example I

In a first example, the scintillation material 710 results in emission of photons at different wavelengths dependent upon the energy of the residual charged particle beam 267, which is the treatment beam 269 after passing through a sample, such as the tumor 720 of the patient 730. For instance, as the residual charged particle beam 267 slows in the scintillation material, the wavelength of secondary photons increases resultant in a color shift as a function of position along the path or vector of the residual charged particle beam 267. Hence, use of wavelengths of the photons detected by detector elements in the detector array 1410, or as described infra multiple detector arrays, viewing varying depths of the scintillation material 710 are used to back calculate state of the residual charged particle beam 267.

Example II

In a second example, the scintillation material 710 results in emission of differing numbers of photons as a function of the energy of the residual charged particle beam 267, which changes as a function of depth of penetration into the scintillation material 710. For instance, as the residual charged particle beam 267 slows in the scintillation material 710, the intensity of secondary photons changes as a function of position along the path or vector of the residual charged particle beam 267. Hence, use of the intensity of the signals of detector element of the detector array 1410, or as described infra multiple detector arrays, viewing varying depths of the scintillation material 710 are used to back calculate state of the residual charged particle beam 267 as a function of depth in the scintillation material 710.

Example III

In a third example, the scintillation material 710 is a set of n scintillation materials having differing secondary photon emission properties as a function of incident or transiting positively charged particles, where n is a positive integer such as greater than 1, 2, 3, 4, 5, or 10. For clarity of presentation and without loss of generality, cases of using a set of scintillation materials are described herein.

Referring now to FIG. 15, in a first case, three scintillation materials are used in a scintillation block, section, or volume of the multiplexed scintillation system 1500. Particularly, a first scintillation material 711, a second scintillation material 712, and a third scintillation material 713 are used at a first, second, and third depth along a path of the residual charge particle beam 267 or z-axis. Further, as illustrated, the first scintillation material 711, the second scintillation material 712, and the third scintillation material 713 emit light at three separate wavelengths, such as from three distinct chemical compositions of the three scintillation materials 711, 712, 713. For clarity of presentation, the three wavelengths are denoted blue (B), green (G), and red (R); however, any wavelength, range of wavelength, or ranges of wavelengths from 200 to 2500 is optionally used. As illustrated, when the residual charged particle beam 267 has only enough energy to penetrate into the first scintillation material 711, then only blue light is emitted. Further, when the residual charged particle beam 267 has sufficient energy to penetrate into only the second scintillation material 712, then only blue light and green light is emitted. In this case, the colors of the emitted light yields additional information on the path of the positively charged particles, which provides a useful constraint on back calculation of the state of the residual charged particle beam 267. Still further, when the residual charged particle beam 267 has a large enough energy to penetrate into the third scintillation material 713, then blue, green, and red light is emitted; again adding useful information on the state of the residual charged particle beam 267 and useful constraints on back calculation of the residual charged particle beam state.

In a second case the set of scintillation materials comprise different thicknesses, such as n thicknesses, where n is a positive integer. Still referring to FIG. 15, for clarity of presentation and without loss of generality, three thicknesses of scintillation materials are illustrated along a longitudinal z-axis of the residual charged particle beam 267. Particularly, the first scintillation material 711 is illustrated with a first pathlength, $b_1$; the second scintillation material 712 is illustrated with a second pathlength, $b_2$; and the third scintillation material 713 is illustrated with a third pathlength, $b_3$. By using thinner layers, relative to a homogeneous scintillation material, of a given light emitting color, identification, post-processing, and/or back calculation of the points of origin of secondary emission of photons, resultant from passage of the residual charged particle beam 267, are constrained and thus the path of the residual charged particle beam 267 and corresponding treatment beam 269 through the tumor 720 is identified with more accuracy and/or precision. The layers of scintillation material optionally emit n wavelengths or bands of light. Further, the use of one material emitting a first color at a first layer is optionally used again for another non-adjacent layer. Similarly, a pattern of colors from corresponding layers is optionally repeated as a function of position along the residual charged particle beam 267, such as B, G, R, B, G, R, . . . , B, G, R.

Example IV

In a fourth example, a color filter array 1414 is optically coupled to the detector array 1410, where the color filter array 1414 is in a secondary photon path between the scintillation material 710 and the detector array 1410. Similarly and preferably, a two-dimensional color filter array is optically coupled to a two-dimensional detector array in the secondary photon path. Using the color filter array 1414 as a portion of an imaging system, a point of origin of the secondary photon is determined, which yields information on path of the residual charged particle beam 267. For clarity of presentation, the color filter array 1414 is described as a Bayer matrix; a cyan, yellow, green, magenta filter, which is a CYGM filter; a red, green, blue, emerald filter, which is a RGBE filter, and/or a two color filter array. Generally any repeating array of color filters or even non-repeating pattern of optical filters is used in the color filter array 1414.

Example VI

Generally, components of the tomography system, described supra, are combined in any combination and/or permutation. For instance, still referring to FIG. 15, a sixth example is provided using: (1) the first scintillation material 711 with the first pathlength, $b_1$; (2) the second scintillation material 712 with the second pathlength, $b_2$; (3) the third scintillation material 713 with the third pathlength, $b_3$; (4) the color filter array 1414; (5) the micro-optics array 1412; and (6) the detector array 1410, all in two-dimensional configurations as part of an imaging system imaging the scintillation materials and secondary photons emitted therefrom, resultant from passage, transit, energy transfer from, interaction with, or termination of the residual charged particles in the residual charged particle beam 267. Calculation of position and direction of the residual charged particle beam 267, with or without use of an imaging sheet, allows a more accurate determination of an exit point of the treatment beam 269 or start of the residual energy beam 269 from the patient 730 and a corresponding path of the charged particle beam from the prior side of the patient 730, through the patient 730, and to the posterior exit point of the patient 730.

Scintillation Array

Figure 16A:
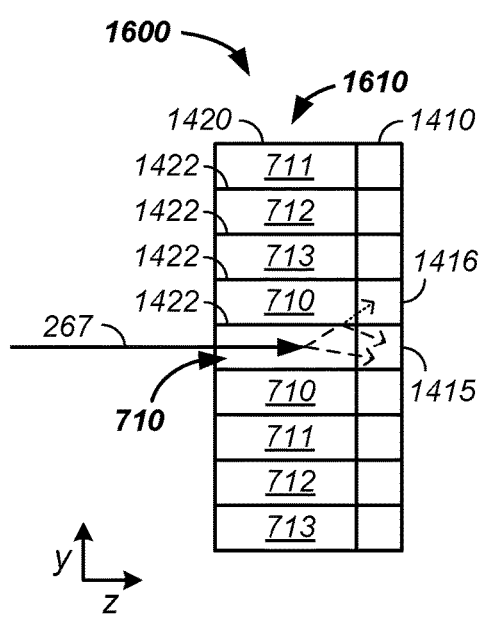
FIG. 16A illustrates an array of scintillation optics.

Referring now to FIG. 16A, the scintillation material 710 is optionally configured as an array of scintillation materials and/or as an array of scintillation sections 1610 in a multiplexed scintillation detector 1600, where elements of the array of scintillation sections 1610 are optionally physically separated. For clarity of presentation and without loss of generality examples follow that described and/or illustrate the array of scintillation sections 1610 as an element of the tomography system.

Example I

In a first example, referring still to FIG. 16A, the scintillation material 710 described above is illustrated in a configuration of an array of scintillation sections 1610 or an array of scintillation optics. As illustrated, elements of the array of scintillation sections 1610 having a first index of refraction are separated by a separation material or cladding 1422 having a second index of refraction that is less than the first index of refraction. For example, the first index of refraction is greater than 1.4, in a range of 1.3 to 1.7, and/or in a range of 1.4 to 1.6 and the second index of refraction is in a range of 1.0 to 1.3 or 1.4. The difference in index of refraction forms a light-pipe similar to a fiber optic, for the photons at or above a total internal reflectance angle threshold. Referring now to FIG. 16B, the core scintillation material 710 and the surrounding cladding 1422 is further illustrated within a buffer material 1424. While the light-pipe in FIG. 16B is illustrated with a circular cross-sectional shape, generally the light pipe cross-sectional shape is of any geometry, such as a rounded corner polygon, square, or rectangle. Referring again to FIG. 16A, the residual charged particle beam 267 is illustrated as inducing emission of two photons, illustrated as dashed lines. The first photon passes straight to a first detector element 1415 of the detector array 1410. The second photon reflects off of the surrounding cladding 1422 into the first detector element. As illustrated with the dotted line, without the surrounding cladding 1422, having a lower index of refraction than the scintillation material 710, the second photon would have struck a second detector element 1416 of the detector array 1410. Hence, by restricting, x- and/or y-axis movement of the photon, as limited by the respective index of refractions, detected and determined resolution of the path of the residual charged particle is enhanced and a corresponding enhancement of the tomographic image is achieved, as described supra.

Example II

In a second example, still referring to FIG. 16B, individual elements of the array of scintillation sections 1610 or scintillation optics are comprised of individual scintillation materials, such as the first scintillation material 711, the second scintillation material 712, and the third scintillation material 713. Optionally, the surrounding cladding 1422 is only used between a repeating set of the scintillation materials, in this case between every three longitudinal elements of scintillation materials.

Example III

Figure 16C:
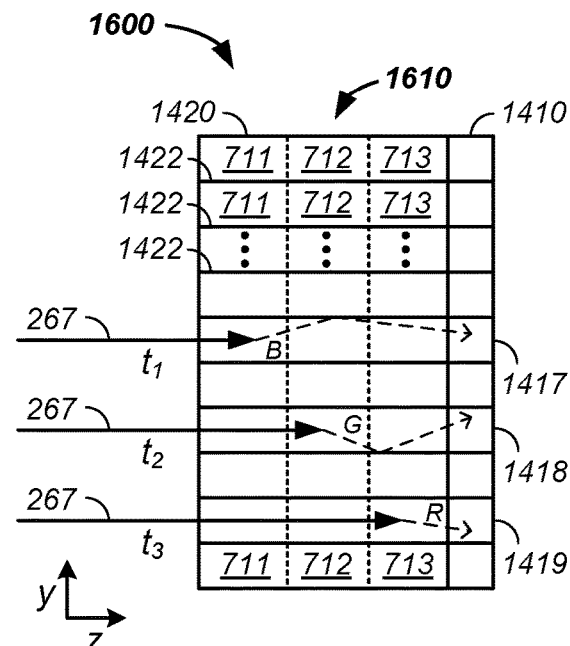
FIG. 16C illustrates an x-, y-, z-axes array of scintillation optics or scintillation materials.
Figure 16B:
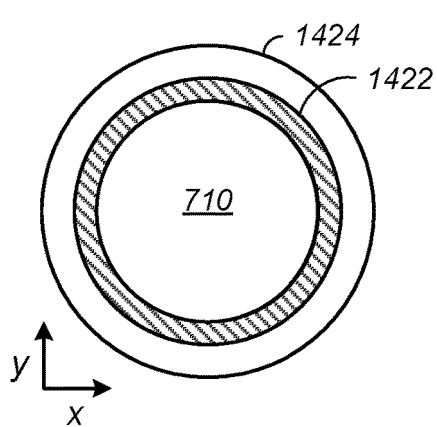
FIG. 16B illustrates a scintillating fiber optic.

In a third example, referring now to FIG. 16C, as in the first example the scintillation material 710 described above is illustrated as an array of scintillation sections 1610, where individual longitudinal paths of the scintillation sections 1610 along the z-axis are separated by the cladding with the second lower index of refraction compared indices of refraction of a set of scintillation materials. However, in this example, the longitudinal paths of a given scintillation section comprises n sections of scintillation materials, where n is a positive integer of 2, 3, 4, 5, or more. As illustrated, longitudinal sections comprise the second scintillation material 712 between the first scintillation material 711 and the third scintillation material 713. Further, as illustrated at a first time, $t_1$, the residual charged energy beam 267 strikes the first scintillation material generating a blue photon, B, detected at a third detector element 1417, where the blue photon is maintained in a resolved x/y-range by the surrounding cladding 1422. Similarly, at a second time, $t_2$, and third time, $t_3$, respectively, residual charged energy beams generate a green photon, G, and a red photon, R, respectively, which are detected with a fourth detector element 1418 and a fifth detector element 1419, respectively. Again, the surrounding cladding 1422 limits x/y-plane translation of the green photon and the red photon. As: (1) the color of the photon, B, G, R, is indicative of the z-axis energy of the residual charged particle beam 267 in the longitudinally segmented sections of the elements of the fiber optic array 1410 and (2) the x/y-plane position of the residual charged particle beam 267 is restricted by the cladding 1422 between the axially separated scintillation sections 1610 of the scintillation optic array, x, y, and z information or spatial position and energy information about the residual charged particle beam 267 is obtained as a function of time, which is used in a back calculation of the path of: (1) the treatment beam 269 or imaging beam and (2) presence and structure of constituents of the patient 730, such as the tumor 720, blood, bone, muscle, connective tissue, collagen, elastin, and/or fat.

Example IV

In another example, one or more imaging optic, such as a light directing optic and/or a focusing optic, used to image the scintillation material comprises the scintillation material 710.

Enhanced Multi-Directional Scintillation Detection

Photons emitted from the scintillation material, resultant from energy transfer from a passing residual charged particle beam 267, emit in many directions. Hence, detection and/or imaging of the photons in many planes or directions provides an opportunity for enhanced signal-to-noise, resolution, accuracy, and/or precision of determination of state of the residual charged particle beam 267 and from that enhanced resolution, accuracy, and precision of the imaged sample, such as the tumor 720 of the patient 730.

Figure 17A:
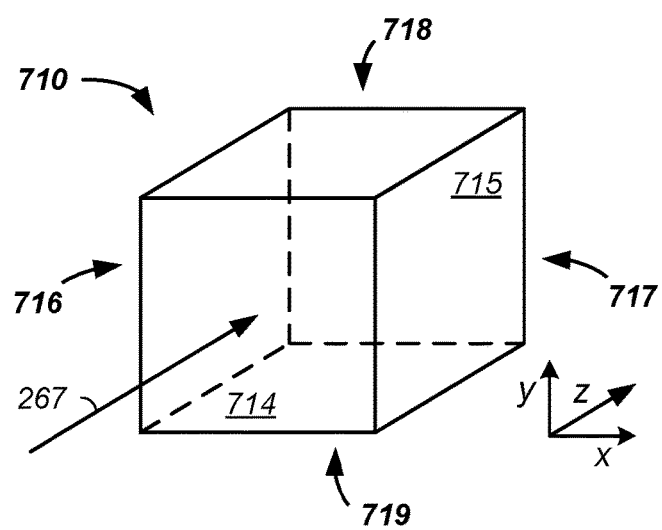
FIG. 17A illustrates a scintillation material.

Referring now to FIG. 17A, herein the scintillation material 710, in the form of a block or as segmented sections has a prior surface 714 or front surface, a posterior surface 715 or back surface, a dexter surface 716 or viewer's left surface, a sinister surface 717 or viewer's right surface, a top surface 718, and a bottom surface 719.

Generally, the detector array 1410 and/or any of the accessories thereof, such as the micro-optics array 1412, color filter array 1414, axially separated sections, and/or longitudinally separated sections, is optionally used on any surface of the scintillation material 710. Further, referring now to FIG. 17B, the detector array 1410 is optionally a set of detector arrays 1700, such as n detector arrays where n is a positive integer. In FIG. 17B, the set of detector arrays 1700 includes: (1) a second detector array 1702 optically coupled to the posterior surface 715 of the scintillation material 710; (2) a fourth detector array 1704 optically coupled to the sinister surface 716 of the scintillation material 710; and (3) a fifth detector array 1705 optically coupled to the top surface 718 of the scintillation material 710. The use of multiple detector arrays, each configured to image the scintillation material 710, enhances accuracy and precision of knowledge of path of the residual charged particle beam 267 through enhanced accuracy, precision, and resolution of points of origin of the resultant emitted photons and as discussed above the resulting accuracy, precision, and resolution of the imaged object. As illustrated, use of three detector arrays set at orthogonal angles allows imaging of the scintillation material in three dimensions, which aids in determination of the path of the residual charged particle beam 267. Optionally, each of the set of detector arrays 1700 is set at any orientation in the x-, y-, z-axes space.

Referring now to FIG. 17B, FIG. 17C, and FIG. 17D, the set of detector arrays 1700 is illustrated with six detector arrays: (1) a first detector array 1701 optically coupled to the prior surface 714 of the scintillation material 710; (2) a second detector array 1702 optically coupled to the posterior surface 715 of the scintillation material 710; (3) a third detector array 1703 optically coupled to the dexter surface 716 of the scintillation material 710; (4) a fourth detector array 1704 optically coupled to the sinister surface 717 of the scintillation material 710; (5) a fifth detector array 1705 optically coupled to the top surface 718 of the scintillation material 710; and (6) a sixth detector array 1706 optically coupled to the bottom surface 719 of the scintillation material 710. Use of a detector array on each surface of the scintillation material 710 allows detection of secondary photons, resultant from the residual charged particle beam 267, with a corresponding increase and/or maximum percentage of detection of the emitted photons. For clarity of presentation and without loss of generality three secondary photons are illustrated: a first secondary photon 1722, a second secondary photon 1724, and a third secondary photon 1726. The larger number of detected photons, with the multiple detector arrays, yields a larger number of data points to more accurately and precisely determine state of the residual charged particle beam with a corresponding enhancement of the tomographic image, as described supra.

Still referring to FIG. 17C, optionally, the prior surface 714 of the scintillation material 710 comprises an aperture 1710 through which the residual charged particle beam 267 passes. Optionally, no aperture is used on the prior surface 714 of the scintillation material 710 and the densities and pathlengths of the first detector array 1701 are used in a calculation of an energy of the residual charged particle beam 267.

Imaging

Generally, medical imaging is performed using an imaging apparatus to generate a visual and/or a symbolic representation of an interior constituent of the body for diagnosis, treatment, and/or as a record of state of the body. Typically, one or more imaging systems are used to image the tumor and/or the patient. For example, the X-ray imaging system and/or the positively charged particle imaging system, described supra, are optionally used individually, together, and/or with any additional imaging system, such as use of X-ray radiography, magnetic resonance imaging, medical ultrasonography, thermography, medical photography, positron emission tomography (PET) system, single-photon emission computed tomography (SPECT), and/or another nuclear/charged particle imaging technique.

Figure 18:
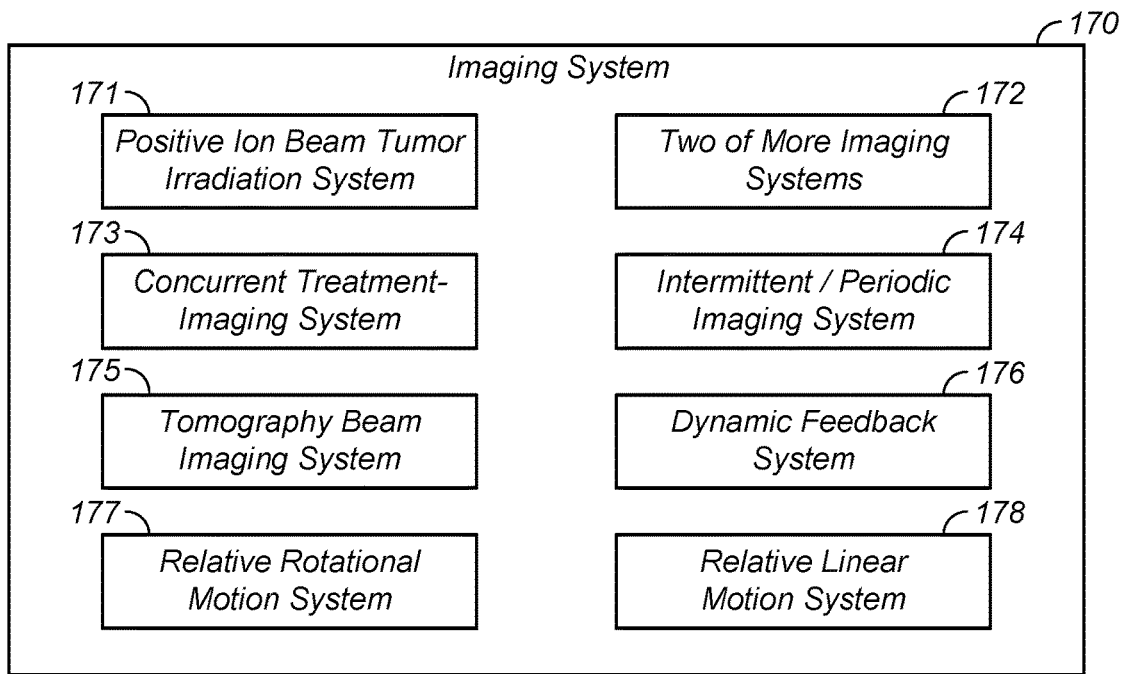
FIG. 18 illustrates subsystems of an imaging system.

Referring now to FIG. 18, the imaging system 170 is further described. As described supra, the imaging system 170 optionally uses:

- a positive ion beam tumor irradiation system 171;
- two or more imaging systems 172, where the individual imaging systems generate data for a composite image of the sample;
- a concurrent treatment imaging system 173, where imaging occurs during treatment of the tumor 720 with the positively charged particle or in-between treatment of voxels of the tumor 720;
- an intermittent or periodic imaging system 174, where one or more update images, confirmation images, and/or adjustment images are collected to update a previous image, alter a treatment plan, and/or stop a current treatment of the tumor 720 with the treatment beam 269;
- a tomography beam imaging system 175 comprising generating tomograms from any radiology technology;
- a dynamic feedback system 176, such as use of a positron emission tomography signal to dynamically control state and/or movement of a positive ion tumor treatment beam;
- a relative rotational motion system 177 between the patient and an imaging beam; and/or
- a relative linear motion system 178 between the patient and a radiography imaging beam.

To clarify the imaging system and without loss of generality several examples are provided.

Example I

In a first example, a positron emission tomography system is used to monitor, as a function of time, a precise and accurate location of the treatment beam 269 relative to the tumor 720. Signal from the positron emission tomography system is optionally: (1) recorded to provide a reviewable history of treatment of the tumor 720 with the positively charged particle beam or treatment beam 269 and/or (2) used to dynamically monitor the position of the treatment beam 269 and to function as a feedback control signal to dynamically adjust position of the treatment beam 269 as a function of time while scanning through treatment voxels of the tumor 720.

Example II

In a second example, an imaging system images the tumor 720 as a function of imaging system paths, which is movement of at least a portion of the imaging system beam along a first path relative to the tumor 720, while the charged particle beam system 100 treats a series of voxels of the tumor 720 along a set of treatment beam paths. In various cases: (1) the imaging system paths and treatment beam paths are essentially parallel paths, such as the two paths forming an angle with the tumor of less than 10, 5, 2, or 1 degrees; (2) the imaging system paths and treatment beam paths are essentially perpendicular to one another, such as forming an angle with the tumor 720 of greater than 70, 80, 85, 88, or 89 degrees and less than 91, 92, 95, 100, or 110 degrees; (3) as the treatment beam 269 and gantry nozzle 610, of the particle beam system 100, rotates around the tumor 720 with rotation of the gantry 960 at a first rotational rate, the imaging system path rotates around the tumor 720 at a second rotational rate; and (4) as the treatment beam 269 and gantry nozzle 610, of the particle beam system 100, relatively rotates around the tumor 720, the imaging system paths translate along a vector, such as while the tumor 720 is treated along a set of rotated lines joined at the tumor, the imaging system paths form a set of essentially parallel lines, such as a set of vectors along a plane and/or a set of vectors passing through a first or prior side of the tumor.

Figure 19A:
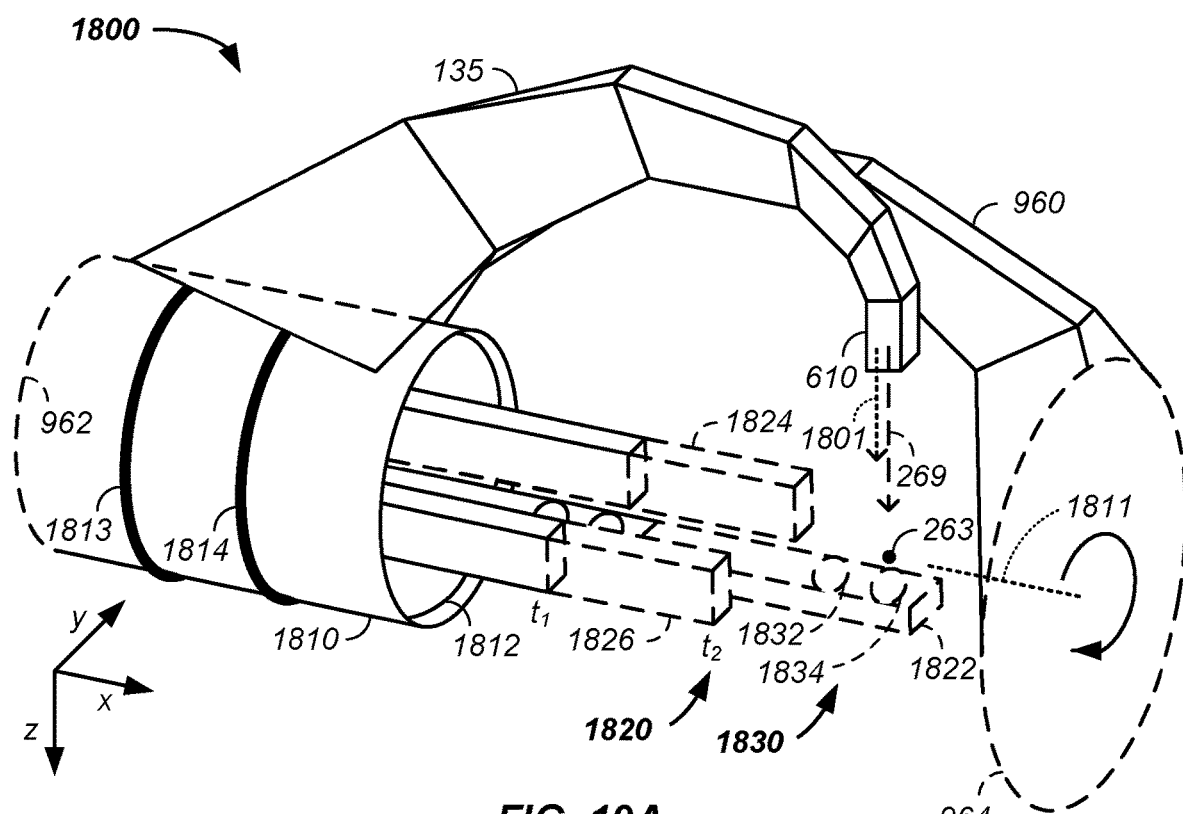
FIG. 19A illustrates a hybrid gantry-imaging system.
Figure 19B:
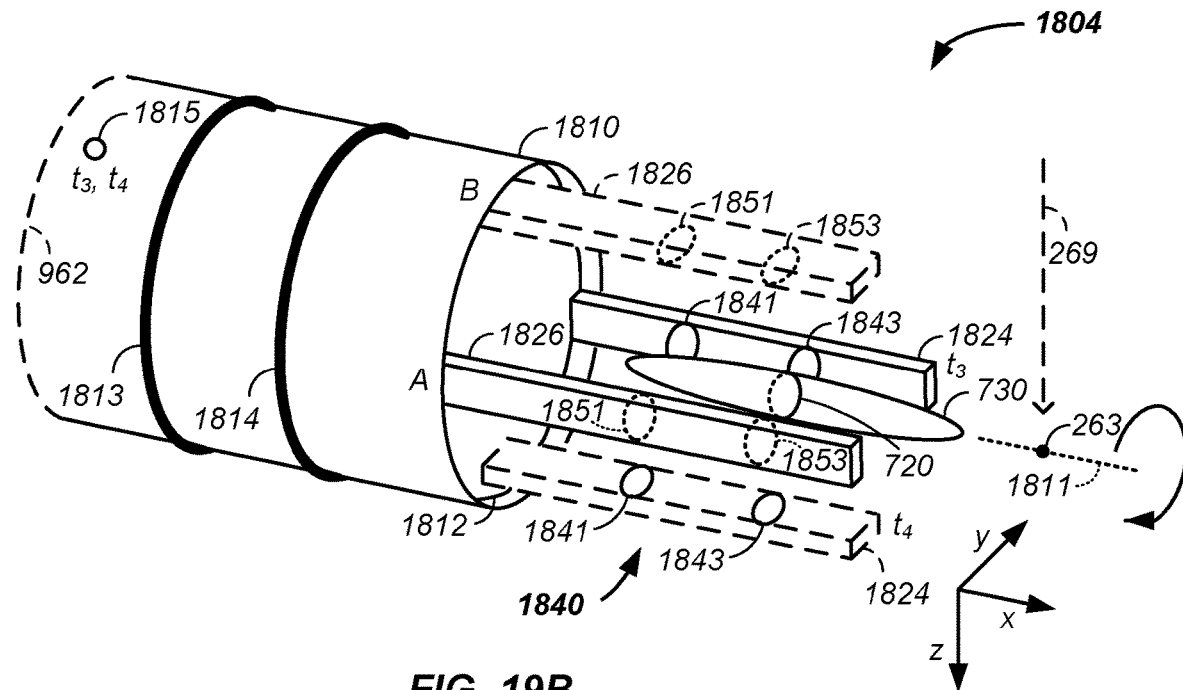
FIG. 19B illustrates a secondary rotation system, of the gantry, used for imaging.

Referring now to FIGS. 19(A-C), a hybrid cancer treatment-imaging system 1800 is illustrated. Generally, the gantry 960, which optionally and preferably supports the gantry nozzle 610, rotates around the tumor 720, as illustrated in FIG. 19B, and/or an isocentre 263, as illustrated in FIG. 19A, of the charged particle beam. As illustrated, the gantry 960 rotates about a gantry rotation axis 1811, such as using a rotatable gantry support 1810. In one case, the gantry 960 is supported on a first end 962 by a first buttress, wall, or support, not illustrated, and on a second end 964 by a second buttress, wall, or support, not illustrated. A first optional rotation track 1813 and a second optional rotation track coupling the rotatable gantry support and the gantry 960 are illustrated, where the rotation tracks are any mechanical connection. Further, as illustrated, for clarity of presentation, only a portion of the gantry 960 is illustrated to provide visualization of the supported beam transport system 135 or a section of the beamline between the synchrotron 130 and the patient 730. To further clarify, the gantry 960 is illustrated, at one moment in time, supporting the gantry nozzle 610 of the beam transport system 135 in an orientation resulting in a vertical vector of the treatment beam 269. As the rotatable gantry support 1810 rotates, the gantry 960, the beam transport line 135, the gantry nozzle 610 and the treatment beam 269 rotate about the gantry rotation axis 1811, illustrated as the x-axis, forming a set of treatment beam vectors originating at circumferential positions about tumor 720 or isocentre 263 and passing through the tumor 720. Optionally, an X-ray beam path 1801, from an X-ray source, runs through and moves with the dynamic gantry nozzle 610 parallel to the treatment beam 269. Prior to, concurrently with, intermittently with, and/or after the tumor 720 is treated with the set of treatment beam vectors, one or more elements of the imaging system 170 image the tumor 720 of the patient 730.

Still referring to FIG. 19A, the hybrid cancer treatment-imaging system 1800 is illustrated with an optional set of rails 1820 and an optional rotatable imaging system support 1812 that rotates the set of rails 1820, where the set of rails 1820 optionally includes n rails where n is a positive integer. Elements of the set of rails 1820 support elements of the imaging system 170, the patient 730, and/or a patient positioning system. The rotatable imaging system support 1812 is optionally concentric with the rotatable gantry support 1810. The rotatable gantry support 1810 and the rotatable imaging system support 1812 optionally: co-rotate, rotate at the same rotation rate, rotate at different rates, or rotate independently. A reference point 1815 is used to illustrate the case of the rotatable gantry support 1810 remaining in a fixed position, such as a treatment position at a third time, $t_3$, and a fourth time, $t_4$, while the rotatable imaging system support 1812 rotates the set of rails 1820.

Still referring to FIG. 19A, any rail of the set of rails optionally rotates circumferentially around the x-axis, as further described infra. For instance, the first rail 1822 is optionally rotated as a function of time with the gantry 960, such as on an opposite side of the gantry nozzle 610 from the tumor 720 of the patient 730.

Still referring to FIG. 19A, a first rail 1822 of the set of rails 1820 is illustrated in a first retracted position at a first time, $t_1$, and at a second extended position at a second time, $t_2$. The first rail 1822 is illustrated with a set of n detector types 1830, such as a first detector 1832 or first detector array at a first extension position of the first rail 1822 and a second detector 1834 or second detector array at a second extension position of the first rail 1822, where n is a positive integer, such as 1, 2, 3, 4, 5, or more. The first detector 1832 and the second detector 1834 are optionally and preferably two detector array types, such as an X-ray detector and a scintillation detector. In use, the scintillation detector is positioned, at the second extended position of the first rail 1822, opposite the tumor 730 from the gantry nozzle 610 when detecting scintillation, resultant from passage of the residual charged particle beam 267 into the scintillation material 710, such as for generating tomograms, tomographic images, and/or a three-dimensional tomographic reconstruction of the tumor 720. In use, the first rail 1822 is positioned at a third extended position, not illustrated, which places the second detector or X-ray detector opposite the tumor 720 from the gantry nozzle 610, such as for generating an X-ray image of the tumor 720. Optionally, the first rail 1822 is attached to the rotatable gantry support 1810 and rotates with the first gantry support 1810. The first rail 1822 is optionally retracted, such as illustrated at the first time, $t_1$, such as for some patient positions about the isocentre 263.

Figure 19C:
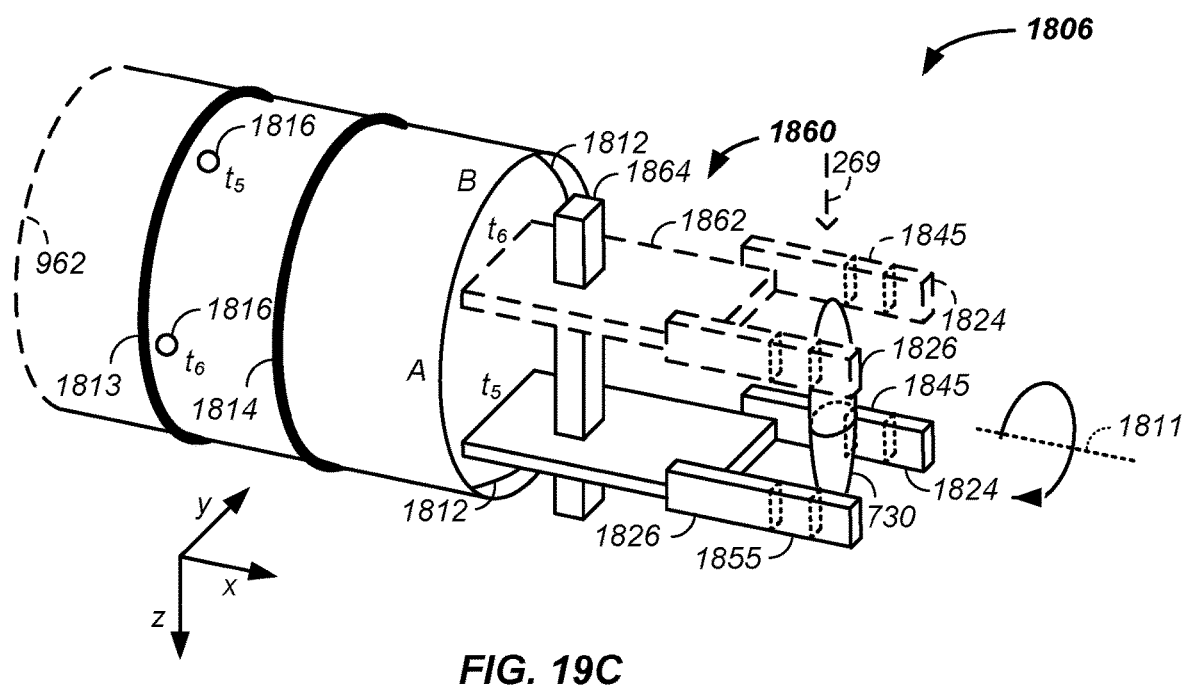
FIG. 19C illustrates a linearly translatable imaging system of the gantry.

Still referring to FIG. 19A and referring again to FIG. 19B and FIG. 19C, a second rail 1824 and a third rail 1826 of the set of rails 1820 are illustrated at a retracted position at a first time, $t_1$, and an extended position at a second time, $t_2$. Generally, the second rail 1824 and the third rail 1826 are positioned on opposite sides of the patient 730, such as a sinister side and a dexter side of the patient 730. Generally, the second rail 1824, also referred to as a source side rail, positions an imaging source system element and the third rail 1826, also referred to as a detector side rail, positions an imaging detector system element on opposite sides of the patient 730. Optionally and preferably, the second rail 1824 and the third rail 1826 extend away from the first buttress 962 and retract toward the first buttress 962 together, which keeps a source element mounted, directly or indirectly, on the second rail 1824 opposite the patient 730 from a detector element mounted, directly or indirectly, on the third rail 1826. Optionally, the second rail 1824 and the third rail 1826 translate, such as linearly, on opposite sides of an axis perpendicular to the gantry rotation axis 1811, as further described infra. Optionally, the second rail 1824 and the third rail 1826 position PET detectors for monitoring emissions from the tumor 720 and/or the patient 730, as further described infra.

Still referring to FIG. 19B, a rotational imaging system 1840 is described. For example, the second rail 1824 is illustrated with: (1) a first source system element 1841 of a first imaging system, or first imaging system type, at a first extension position of the second rail 1824, which is optically coupled with a first detector system element 1851 of the first imaging system on the third rail 1826 and (2) a second source system element 1843 of a second imaging system, or second imaging system type, at a second extension position of the second rail 1824, which is optically coupled with a second detector system element 1853 of the second imaging system on the third rail 1826, which allows the first imaging system to image the patient 730 in a treatment position and, after translation of the first rail 1824 and the second rail 1826, the second imaging system to image the patient in the patient's treatment position. Optionally the first imaging system or primary imaging system and the second imaging system or secondary imaging system are supplemented with a tertiary imaging system, which uses any imaging technology. Optionally, first signals from the first imaging system are fused with second signals from the second imaging system to: (1) form a hybrid image; (2) correct an image; and/or (3) form a first image using the first signals and modified using the second signals or vise-versa.

Still referring to FIG. 19B, the second rail 1824 and third rail 1826 are optionally alternately translated inward and outward relative to the patient, such as away from the first buttress and toward the first buttress. In a first case, the second rail 1824 and the third rail 1826 extend outward on either side of the patient, as illustrated in FIG. 19B. Further, in the first case the patient 730 is optionally maintained in a treatment position, such as in a constrained laying position that is not changed between imagining and treatment with the treatment beam 269. In a second case, the patient 730 is translated toward the first buttress 962 to a position between the second rail 1824 and the third rail 1826, as illustrated in FIG. 19B. In the second case, the patient is optionally imaged out of the treatment beam path 269, as illustrated in FIG. 19B. Further, in the second case the patient 730 is optionally maintained in a treatment position, such as in a constrained laying position that is not changed until after the patient is translated back into a treatment position and treated. In a third case, the second rail 1824 and the third rail 1826 are translated away from the first buttress 962 and the patient 730 is translated toward the first buttress 962 to yield movement of the patient 730 relative to one or more elements of the first imaging system type or second imaging system type. Optionally, images using at least one imaging system type, such as the first imaging system type, are collected as a function of the described relative movement of the patient 730, such as along the x-axis and/or as a function of rotation of the first imaging system type and the second imaging system type around the x-axis, where the first imaging type and second imaging system type use differing types of sources, use differing types of detectors, are generally thought of as distinct by those skilled in the art, and/or have differing units of measure. Optionally, the source is an emissions from the body, such as a radioactive emission, decay, and/or gamma ray emission, and the second rail 1824 and the third rail 1826 position and/or translate one or more emission detectors, such as a first positron emission detector on a first side of the tumor 720 and a second positron emission detector on an opposite side of the tumor 730.

Still referring to FIG. 19B, a hybrid cancer treatment—rotational imaging system 1804 is illustrated. In one example of the hybrid cancer treatment—rotational imaging system 1804, the second rail 1824 and third rail 1826 are optionally circumferentially rotated around the patient 730, such as after relative translation of the second rail 1824 and third rail 1826 to opposite sides of the patient 730. As illustrated, the second rail 1824 and third rail 1826 are affixed to the rotatable imaging system support 1812, which optionally rotates independently of the rotatable gantry support 1810. As illustrated, the first source system element 1841 of the first imaging system, such as a two-dimensional X-ray imaging system, affixed to the second rail 1824 and the first detector system element 1851 collect a series of preferably digital images, preferably two-dimensional images, as a function of co-rotation of the second rail 1824 and the third rail 1826 around the tumor 720 of the patient, which is positioned along the gantry rotation axis 1811 and/or about the isocentre 263 of the charged particle beam line in a treatment room. As a function of rotation of the rotatable imaging system support 1812 about the gantry rotation axis 1811 and/or a rotation axis of the rotatable imaging system support 1812, two-dimensional images are generated, which are combined to form a three-dimensional image, such as in tomographic imaging. Optionally, collection of the two-dimensional images for subsequent tomographic reconstruction are collected: (1) with the patient in a constrained treatment position, (2) while the charged particle beam system 100 is treating the tumor 720 of the patient 730 with the treatment beam 269, (3) during positive charged particle beam tomographic imaging, and/or (4) along an imaging set of angles rotationally offset from a set of treatment angles during rotation of the gantry 960 and/or rotation of the patient 730, such as on a patient positioning element of a patient positioning system.

Referring now to FIG. 19C, a hybrid tumor treatment—vertical imaging system 1806 is illustrated, such as with a translatable imaging system 1860 is described. In one example of the hybrid tumor treatment vertical imaging system 1806, the second rail 1824 and the third rail 1826 are used to acquire a set of images with linear translation of the second rail 1824 and the third rail 1826 past the tumor 720 of the patient 730, such as with movement along an axis as a function of time, such as, as illustrated, along a vertical axis at the fifth time, $t_5$, and a sixth time, $t_6$. As illustrated, the second rail 1824 and the third rail co-translate along a rail support 1864, where the rail support 1864 is optionally positioned inside the rotatable gantry support 1810 and/or the rotatable imaging system support 1812. Optionally and preferably, source elements and detector elements moving past the tumor 720 of the patient 730 on the second rail 1824 and third rail 1826, respectively, are used to collect a scanning set of images, such as PET images, of the tumor as a function of translation along the rail support 1864. In the hybrid tumor treatment—vertical imaging system 1806, the second rail 1824 and elements supported thereon and the third rail and elements supported thereon optionally extend and/or retract, as described supra. Further, in the hybrid tumor treatment—vertical imaging system 1806, the second rail 1824 and elements supported thereon and the third rail and elements supported thereon optionally rotate about the isocentre, such as with rotation of the rotatable gantry support 1810 and/or the rotatable imaging system support 1812. Optionally, any member of the set of rails 1820 extends/retracts, rotates, and/or translates past the tumor 720 of the patient 730 at the same time.

Optionally, the vertical imaging system 1806 moves a PET system detector system element, such as a detector or coupling device, to a position corresponding to a depth of penetration of the treatment beam 269 into the tumor 720 of the patient 730. For clarity of presentation and without loss of generality, an example is provided where the treatment beam 269 is vertical and passes through the gantry nozzle 610 directly above the tumor 720. The treatment beam 269 is of a known energy at a known time, where the known energy is intentionally varied to yield a corresponding varied depth of penetration of the treatment beam 269 into the tumor, such as described by the peak of the Bragg peak. A detector system element of the positron emission tomography system, supported on the vertical imaging system 1806, it optionally translated vertically to observe the depth of penetration of the treatment beam 269. For instance, as the treatment beam energy is decreased, the depth of penetration of the treatment beam 269 into the tumor 720 of the patient 730 decreases and the detector system element of the positron emission tomography system is raised vertically. Similarly, as the treatment beam energy is increased, the depth of penetration of the treatment beam 269 into the tumor 720 of the patient 730 increases and the detector system element of the positron emission tomography system is lowered vertically. Optionally, as the gantry 960 rotates, the vertical imaging system rotates.

Still referring to FIG. 19C, a reference point 1816 is used to illustrate the case of the rotatable gantry support 1810 rotating between a fifth time, $t_5$, and a sixth time, $t_6$, while the translatable imaging system 1860 moves the second rail 1824 and the third rail 1826 along a linear axis, illustrated as the z-axis or treatment beam axis.

Optionally, one or more of the imaging systems described herein monitor treatment of the tumor 720 and/or are used as feedback to control the treatment of the tumor by the treatment beam 269.

Referring now to FIG. 20, a dynamic treatment beam guiding system 2000 is described. As the treatment beam 269 irradiates the tumor 2010 radioactive nuclei or isotopes are formed 2020 where the treatment beam 269 strikes the tumor 720 of the patient 730. The radioactive nuclei emits a positron 2030 that rapidly undergoes electron-positron annihilation 2040, which results in a gamma ray emission 2050. Thus, monitoring location of one or more gamma ray emissions is a measure of the current location of the treatment beam 269. Also, dependent upon the half-life of the formed radioactive nuclei, monitoring location of the gamma ray emissions provides a measure of where the treatment beam 269 has interacted with the tumor 720 and/or the patient 730, which yields information on treatment coverage and/or provides a history of treatment. By monitoring new voxels or positions of gamma ray emission and/or by monitoring intensity drop off of gamma-ray emission over each of multiple recently treated voxels, a current treatment position of the treatment beam 269 is determined. The main controller 110 and/or a dynamic positioning system 2060 is optionally used to dynamically correct and/or alter the current position of the treatment beam 269, such as through control of one or more of the extraction energy, beam guiding magnets, or beam shaping elements.

Referring now to FIG. 21, treatment position determination system 2100 is illustrated. Herein, for clarity of presentation and without loss of generality, a Bragg peak is used to describe a treatment position. However, the techniques described herein additionally apply to the tail of the Bragg peak. As illustrated, at a first time, $t_1$, the treatment beam 269 having a first energy has a first treatment position 2111 at a first depth, $d_1$, into the patient 730 where the first treatment position 2111 is illustrated at a depth corresponding to the Bragg peak. Through the process illustrated in FIG. 20, the treatment beam 269 yields gamma rays 2121 that are detected using a first gamma ray detector 2131 and a second gamma ray detector 2132, such as respectively mounted on first support 2141 on a first side of the tumor 720 and a second support 2142 on a second side of the tumor 720, which is preferably the opposite side of the patient to capture paired gamma ray signals. Optionally and preferably, a common support is used to mount the first and second supports 2141, 2142. As illustrated, at a second time, $t_2$, the treatment beam 269 having a second energy has a second treatment position 2112 at a second depth, $d_2$, where the first and second gamma ray detectors 2131, 2132 are translated, such as via the first and second support 2141, 2142 to positions on opposite sides of the tumor 720, to a second position corresponding to the second energy and the second depth of penetration into the patient 730. Similarly, at a third time, $t_3$, of n times, where n is a positive integer, the treatment beam 269 having a third energy, of n energies corresponding to a set of treatment depths 2110, treats a third treatment position 2113 at a third depth, $d_3$, where the first and second gamma ray detectors 2131, 2132 are translated to positions on opposite sides of the third depth of penetration. In this manner, the first and second gamma ray detectors 2131, 2132 are aligned with the expected depth of penetration corresponding with the current energy of the treatment beam. Generally, as energy of the treatment beam 269 increases, the gamma ray detectors are positioned on opposite sides of a large depth of penetration and as the energy of the treatment beam decreases 269, the detectors are positioned on opposite sides of a relatively shallower depth of penetration. If the first and second gamma ray detectors 2131, 2132 yield low signals versus an expected signal, then the expected treatment position is not met and the position of the first and second gamma ray detectors 2131, 3132 is scanned or dithered, such as along the z-axis as illustrated, to find the maximum gamma ray signal corresponding to an actual depth of penetration. The inventor notes that previously treated positions yield decaying intensities of emitted gamma rays based upon the initial intensity of the treatment beam 269, historical trail positions of the treatment beam 269 overlapping the monitored position, cross-sectional target of the target atom, such as carbon, nitrogen, oxygen, or any atom, and concentration of the target atom, all of which are calculable and are optionally and preferably used to: monitor total treatment of a voxel, determine a current treatment position of the treatment beam 269, dynamically control subsequent positions of the treatment beam 269, and/or record a history of actual treatment. Any deviation between planned treatment and actual treatment is noted in the treatment record, such as for a subsequent treatment, and/or is used in dynamic control of the charged particle beam. Optionally, an array of gamma ray detectors is used, such as in place of a moveable gamma ray detector. Similarly, optionally a pair of gamma ray detectors is used in place of the illustrated translatable first and second gamma ray detectors 2131, 2132.

Still referring to FIG. 21, optionally two or more off-axis gamma ray detector are used to determine treatment of a current voxel and/or treatment of a previously treated voxel. For example, if a first pair of gamma ray detectors are used to determine a z-axis position, a second pair of gamma ray detectors are used to determine an x-axis position or a y-axis position. Similarly, a first pair of gamma ray detector arrays is optionally combined with a second pair of gamma ray detector arrays to increase accuracy and/or precision of treatment of a given voxel. Similarly, gamma ray detectors are optionally positioned and/or moved in a manner similar to placement and/or movement of any of the X-ray sources and/or X-ray detectors described above, such as supported and rotated about the tumor 720 of the patient 730 using the gantry 960, the rotatable gantry support 1810, and/or the rotatable imaging system support 1812.

The inventor notes that the positron emission system here uses radioactive nuclei or isotopes formed in-vivo, in stark contrast to positron emission tomography systems that generate isotopes externally that are subsequently injected into the body. As the in-vivo radioactive nuclei are formed in the tumor 720, the gamma rays are emitted from the tumor 720 and not the tumor and all of the surrounding tissue. This aids a signal-to-noise ratio of the acquired gamma ray signal as the background noise of additional non-tumor body tissues emitting gamma rays is substantially reduced and completely removed if only considering the Bragg peak resultant in the peak signal. Further, as the radioactive nuclei is formed in-vivo, time is not required to recover the radioactive nuclei, move the radioactive nuclei to the patient, inject the radioactive nuclei in the patient, and let the radioactive nuclei disperse in the patient, which take ten minutes of more. In stark contrast, the radioactive nuclei is formed in-situ, such as in the tumor 720, which allows analysis of any radioactive nuclei with a short half-life, such as less than 10, 5, 2, 1, 0.5, 0.1, or 0.05 minutes. Still further, as position of the treatment beam 269 is monitored or determined as a function of time, tomograms of the tumor are generated. The individual tomograms are optionally combined to form an image of the treated tumor or of the tumor as a function of treatment time allowing a video of the collapse of the tumor to be generated and analyzed for real-time modification of the tumor treatment with the treatment beam, to enhance protocols for future tumor treatments of others, and or to monitor sections of the tumor requiring a second treatment.

Multiple Beam Energies

Referring now to FIG. 22A through FIG. 27, a system is described that allows continuity in beam treatment between energy levels.

Figure 22A:
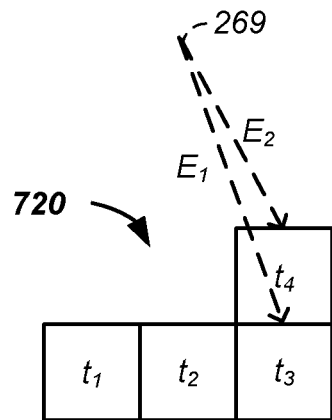
FIG. 22A and FIG. 22B illustrate a decrease and an increase in energy of a treatment beam, respectively.
Figure 22B:
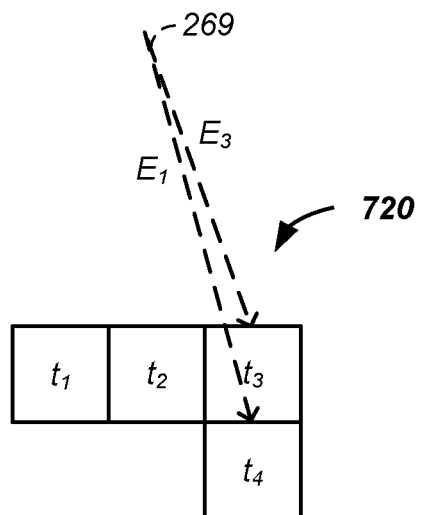

Referring now to FIG. 22A and FIG. 22B, treating the tumor 720 of the patient 730 using at least two beam energies is illustrated. Referring now to FIG. 22A, in a first illustrative example the treatment beam 269 is used at a first energy, $E_1$, to treat a first, second, and third voxel of the tumor at a first, second, and third time, $t_{1-3}$, respectively. At a fourth time, $t_4$, the treatment beam 269 is used at a lower second energy, $E_2$, to treat the tumor 720, such as at a shallower depth in the patient 730. Similarly, referring now to FIG. 22B, in a second illustrative example the treatment beam 269 is used at a first energy, $E_1$, to treat a first, second, and third voxel of the tumor at a first, second, and third time, $t_{1-3}$, respectively. At a fourth time, $t_4$, the treatment beam 269 is used at a higher third energy, $E_3$, to treat the tumor 720, such as at a greater depth of penetration into the patient 730.

Figure 23:
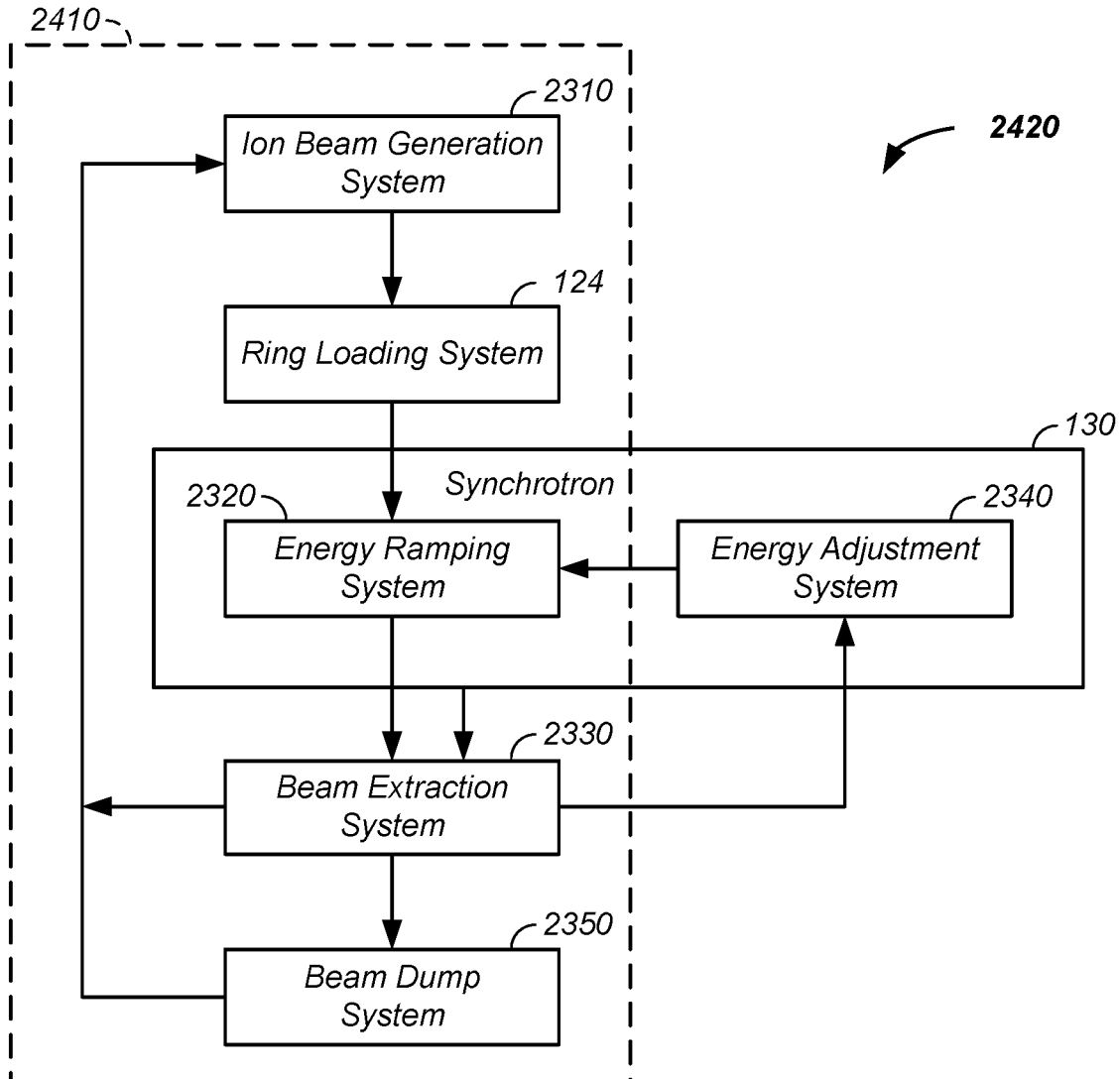
FIG. 23 illustrates differences between a beam interrupt and a beam alteration system.

Referring now to FIG. 23, two systems are described that treat the tumor 720 of the patient 730 with at least two energy levels of the treatment beam 269: (1) a beam interrupt system 2410 dumping the beam from an accelerator ring, such as the synchrotron 130, between use of the treatment beam 269 at a first energy and a second energy and (2) a beam adjustment system 2420 using an ion beam energy adjustment system 2340 designed to adjust energies of the treatment beam 269 between loadings of the ion beam. Each system if further described, infra. For clarity of presentation and without loss of generality, the synchrotron 130 is used to represent any accelerator type in the description of the two systems. The field accepted word of "ring" is used to describe a beam circulation path in a particle accelerator.

Referring still to FIG. 23, in the beam interrupt system 2410, an ion beam generation system 2310, such as the ion source 122, generates an ion, such as a cation, and a ring loading system 124, such as the injection system 120, loads the synchrotron 130 with a set of charged particles. An energy ramping system 2320 of the synchrotron 130 is used to accelerate the set of charged particles to a single treatment energy, a beam extraction system 2330 is used to extract one or more subsets of the charged particles at the single treatment energy for treatment of the tumor 720 of the patient 730. When a different energy of the treatment beam 269 is required, a beam dump system 2350 is used to dump the remaining charged particles from the synchrotron 130. The entire sequence of ion beam generation, accelerator ring loading, acceleration, extraction, and beam dump is subsequently repeated for each required treatment energy.

Referring still to FIG. 23, the beam adjustment system 2420 uses at least the ion beam generation system 2310, the ring loading system 124, the energy ramping system 2320, and the beam extraction system 2330 of the first system. However, the beam adjustment system uses an energy adjustment system 2340 between the third and fourth times, illustrated in FIG. 22A and FIG. 22B, where energy of the treatment beam 269 is decreased or increased, respectively. Thus, after extraction of the treatment beam 269 at a first energy, the energy adjustment system 2340, with or without use of the energy ramping system 2320, is used to adjust the energy of the circulating charged particle beam to a second energy. The beam extraction system 2330 subsequently extracts the treatment beam 269 at the second energy. The cycle of energy beam adjustment 2340 and use of the beam extraction system 2330 is optionally repeated to extract a third, fourth, fifth, and/or $n^{th}$ energy until the process of dumping the remaining beam and/or the process of loading the ring used in the beam interrupt system is repeated. The beam interrupt system and beam adjustment systems are further described, infra.

Figure 24:
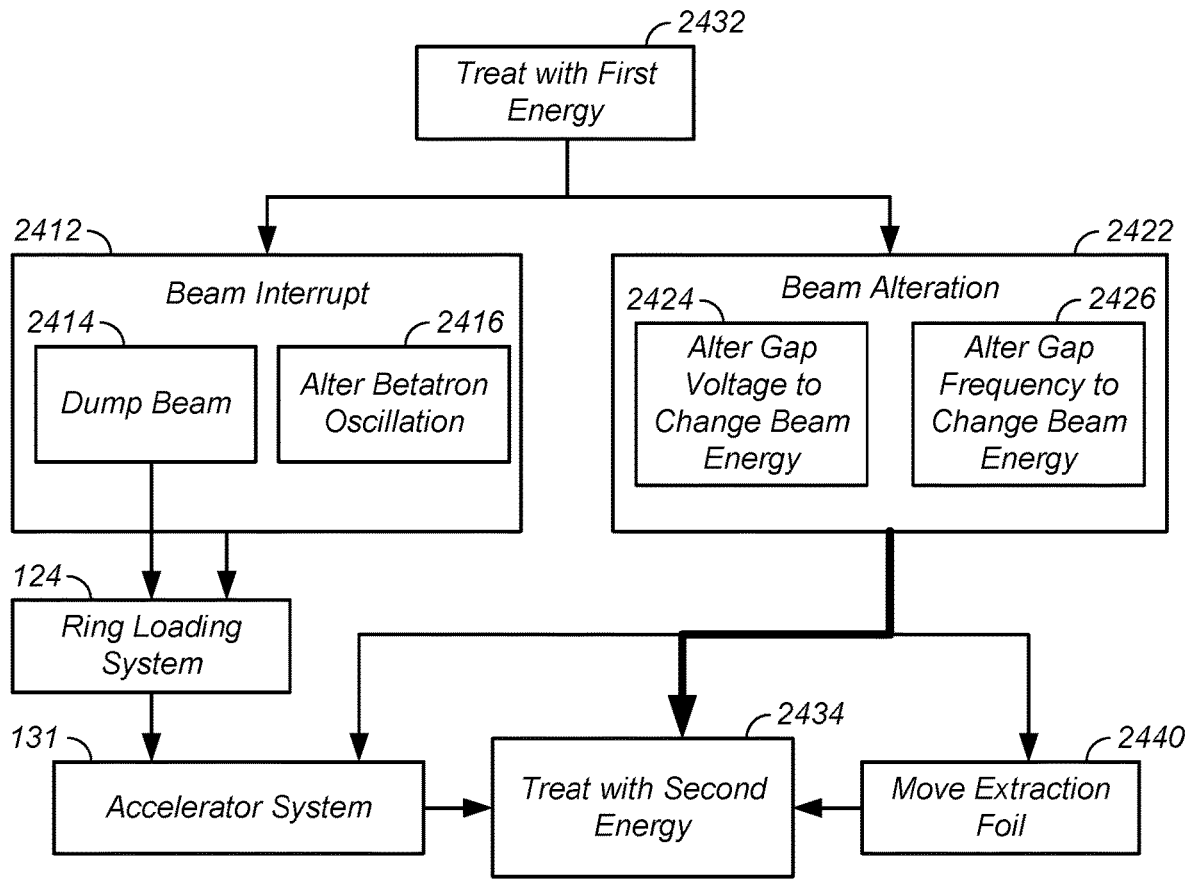
FIG. 24 further illustrates differences between a beam interrupt and a beam alteration system.

Referring now to FIG. 24, the beam interrupt system 2410 is further described. After loading the ring, as described supra, the tumor 720 is treated with a first energy 2432. After treating with the first energy, the beam interrupt system 2410 uses a beam interrupt step, such as: (1) stopping extraction, such as via altering, decreasing, shifting, and/or reversing the betatron oscillation 2416, described supra, to reduce the radius of curvature of the altered circulating beam path 265 back to the original central beamline and/or (2) performing a beam dump 2414. After extraction is stopped and in the case where the beam is dumped, the ring loading system 124 reloads the ring with cations, the accelerator system 131 is used to accelerate the new beam and a subsequent treatment, such as treatment with a second energy 2434 ensues. Thus, using the beam interrupt system 2410 to perform a treatment at n energy levels: ions are generated, the ring is filled, and the ring is dumped n−1 times, where n is a positive integer, such as greater than 1, 2, 3, 4, 5, 10, 25, or 50. In the case of interrupting the beam by altering the betatron oscillation 2416, the accelerator system 131 is used to alter the beam energy to a new energy level.

Referring still to FIG. 24, the beam adjustment system 2420 is further described. In the beam adjustment system 2420, after the tumor 720 is treated using a first beam energy 2432, a beam alteration step 2422 is used to alter the energy of the circulating beam. In a first case, the beam is accelerated, such as by changing the beam energy by altering a gap voltage 2424, as further described infra. Without performing a beam dump 2414 and without the requirement of using the accelerator system 131 to change the energy of the circulating charged particle beam, energy of the circulating charge particle beam is altered using the beam alteration system 2422 and the tumor 720 is treated with a second beam energy 2434. Optionally, the accelerator system 131 is used to further alter the circulating charged particle beam energy in the synchrotron 130 and/or the extraction foil is moved 2440 to a non-beam extraction position. However, the inventor notes that the highlighted path, A, allows: (1) a change in the energy of the extracted beam, the treatment beam 269, as fast as each cycle of the charged particle through the ring, where the beam energy is optionally altered many times, such as on successive passes of the beam across the gap, between treatment, (2) treatment with a range of beam energies with a single loading of the beam, (3) using a larger percentage of the circulating charged particles for treatment of the tumor 720 of the patient, (4) a smaller number of charged particles in a beam dump, (5) use of all of the charged particles loaded into the ring, (6) small adjustments of the beam energy with a magnitude related to the gap radio-frequency and/or amplitude and/or phase shift, as further described infra, and/or (7) a real-time image feedback to the gap radio-frequency of the synchrotron 130 to dynamically control energy of the treatment beam 269 relative to position of the tumor 720, optionally as the tumor 720 is ablated by irradiation, as further described infra.

Figure 25:
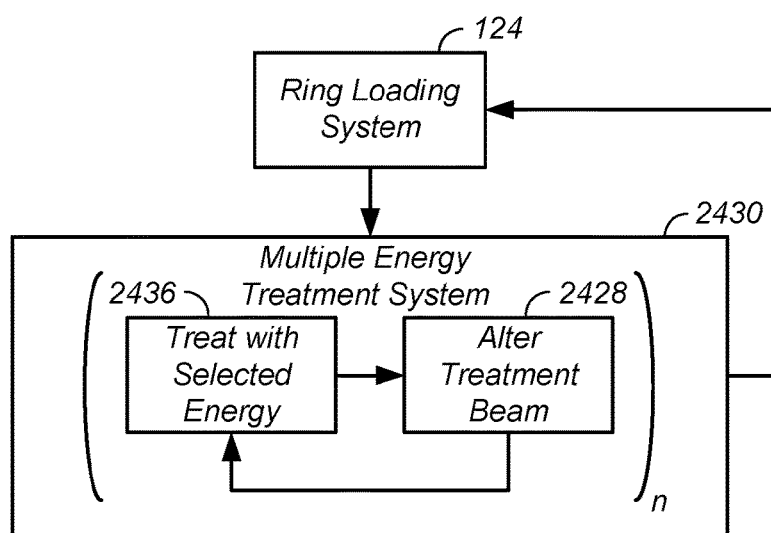
FIG. 25 illustrates treatment of a tumor with multiple beam energies using a single loading of a ring.

Referring now to FIG. 25, the beam adjustment system 2420 is illustrated using multiple beam energies for each of one or more loadings of the ring. Particularly, the ring loading system 124 loads the ring and a multiple energy treatment system 2430 treats the tumor with a selected energy 2436, alters the treatment beam 2428, such as with the beam alteration process 2422, and repeats the process of treating with a selected energy and altering the beam energy n times before again using the ring loading system 124 to load the ring, where n is a positive integer of at least 2, 3, 4, 5, 10, 20, 50, and/or 100.

Figure 26A:
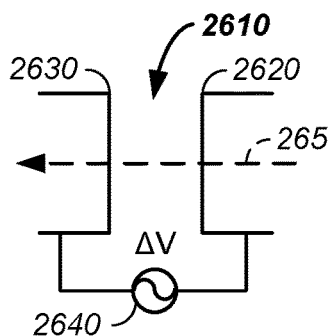
FIG. 26A, FIG. 26B, and FIG. 26C illustrate a generic case, beam acceleration, and beam deceleration, respectively.

Referring now to FIG. 26A the beam alteration 2422 is further described. The circulating beam path 264 and/or the altered circulating beam path 265 crosses a path gap 2610 having a gap entrance side 2620 and a gap exit side 2630. A voltage difference, $\Delta V$, across the path gap 2610 is applied with a driving radio field 2640. The applied voltage difference, $\Delta V$, and/or the applied frequency of the driving radio field are used to accelerate or decelerate the charged particles circulating in the circulating beam path 264 and/or the altered circulating beam path 265, as still further described infra.

Figure 26B:
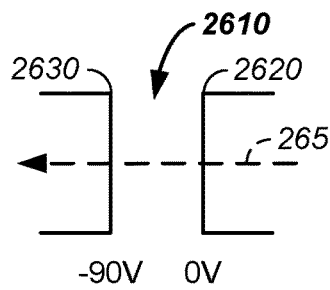
Figure 26C:
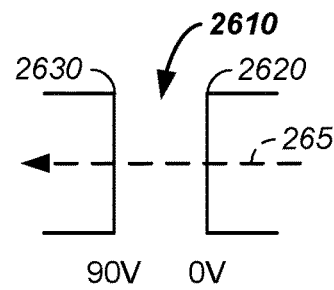

Referring now to FIG. 26B, acceleration of the circulating charge particles is described. For clarity of presentation and without loss of generality, a ninety volt difference is used in this example. However, any voltage difference is optionally used relative to any starting voltage. As illustrated, the positively charged particles enter the path gap 2610 at the gap entrance side 2620 at an applied voltage of zero volts and are accelerated toward the gap exit side 2630 at −90 volts. Optionally and preferably the voltage difference, that is optionally static, is altered at a radio-frequency matching the time period of circulation through the synchrotron.

Referring again to FIG. 26A, phase shifting the applied radio-frequency is optionally used to: (1) focus/tighten distribution of a circulating particle bunch and/or (2) increase or decrease a mean energy of the particle bunch as described in the following examples.

Example I

Referring again to FIG. 26B, in a first genus of a lower potential at the gap exit side 2630 relative to a reference potential of the gap entrance side 2620, in a first species case of the applied radio-frequency phase shifted to reach a maximum negative potential after arrival of a peak intensity of particles in a particle bunch, circulating as a group in the ring, at the gap exit side 2630, then the trailing charged particles of the particle bunch are accelerated relative to the mean position of charged particles of the particle bunch resulting in: (1) focusing/tightening distribution of the circulating particle bunch by relative acceleration of a trailing edge of particles in the particle bunch and (2) increasing the mean energy of the circulating particle bunch. More particularly, using a phase matched applied radio-frequency field, a particle bunch is accelerated. However, a delayed phase of the applied radio-frequency accelerates trailing particles of the particle bunch more than the acceleration of a mean position of the particle bunch, which results in a different mean increased velocity/energy of the particle bunch relative to an in-phase acceleration of the particle bunch. In a second species case of the applied radio-frequency phase shifted to reach a maximum negative potential before arrival of a peak intensity of particles in the particle bunch at the gap exit side 2630, then the leading charged particles of the particle bunch are accelerated less than the peak distribution of the particle bunch resulting in: (1) focusing/tightening distribution of the circulating particle bunch and/or (2) an acceleration of the circulating particle bunch differing from an in-phase acceleration of the particle bunch.

Example II

Referring again to FIG. 26C, in a second genus of a larger potential at the gap exit side 2630 relative to the gap entrance side 2620, using the same logic of distribution edges of the bunch particles accelerating faster or slower relative to the mean velocity of the bunch particles depending upon relative strength of the applied field, the particle bunch is: (1) focused/tightened/distribution reduced and (2) edge distributions of the particle bunch are accelerated or decelerated relative to deceleration of peak intensity particles of the particle bunch using appropriate phase shifting. For example, a particle bunch undergoes deceleration across the path gap 2610 when a voltage of the gap exit side 2630 is larger than a potential of the gap entrance side 2620 and in the first case of the phase shifting the radio-frequency to initiate a positive pulse before arrival of the particle bunch, the leading edge of the particle bunch is slowed less than the peak intensity of the particle bunch, which results in tightening distribution of velocities of particles in the particle bunch and reducing the mean velocity of the particle bunch to a different magnitude than that of a matched phase radio-frequency field due to the relative slowing of the leading edge of the particle bunch. As described above, relative deceleration, which is reduced deceleration versus the main peak of the particle bunch, is achieved by phase shifting the applied radio-frequency field peak intensity to lag the peak intensity of particles in the particle bunch.

Example III

Referring again to FIG. 26A and FIG. 26B, optionally more than one path gap 2610 is used in the synchrotron. Assuming an acceleration case for each of a first path gap and a second path gap: (1) a phase trailing radio-frequency at the first path gap accelerates leading particles of the particle bunch less than acceleration of the peak intensity of particles of the particle bunch and (2) a phase leading radio-frequency at the second path gap accelerates trailing particles of the particle bunch more than acceleration of the peak intensity of particles of the particle bunch. Hence, first particles at the leading edge of the particle bunch are tightened toward a mean intensity of the particle bunch and second particles at the trailing edge of the particle bunch are also tightened toward the mean intensity of the particle bunch, while the particle bunch as a whole is accelerated. The phase shifting process is similarly reversed when deceleration of the particle bunch is desired.

Figure 27:
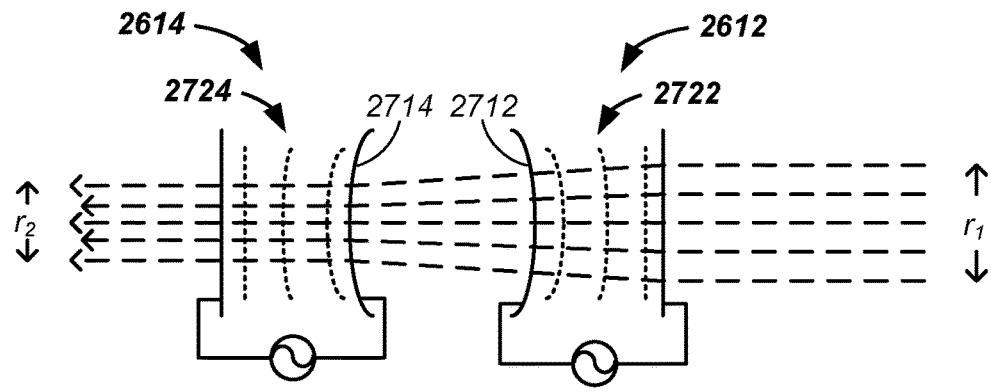
FIG. 27 illustrates use of two of more ring gaps.

In addition to acceleration or deceleration of the beam using applied voltage with or without phase shifting the applied voltage, geometry of the gap entrance side 2620 and/or the gap exit side 2630 using one or more path gaps 2610 is optionally used to radially focus/tighten/distribution tighten the particle bunch. Referring now to FIG. 27, an example illustrates radial tightening of the particle bunch. In this example, a first path gap 2612 incorporates a first curved geometry, such as a convex exit side geometry 2712, relative to particles exiting the first path gap 2612. The first curved surface yields increasingly convex potential field lines 2722, relative to particles crossing the first path gap 2612, across the first path gap 2612, which radially focuses the particle bunch. Similarly, a second path gap 2614 incorporates a second curved geometry or a concave entrance side geometry 2714, relative to particles entering the second path gap 2614. The second curved surface yields decreasingly convex potential field lines 2724 as a function of distance across the second path gap 2614, which radially defocuses the particle bunch, such as back to a straight path with a second beam radius, $r_2$, less than a first beam radius, $r_1$, prior to the first path gap 2612.

Dynamic Energy Adjustment

Referring again to FIG. 22A through FIG. 27, the energy of the treatment beam 269 is controllable using the step of beam alteration 2426. As the applied voltage of the driving radio frequency field 2640 is optionally varied by less than 500, 200, 100, 50, 25, 10, 5, 2, or 1 volt and the applied phase shift is optionally in the range of plus or minus any of: 90, 45, 25, 10, 5, 2, or 1 percent of a period of the radio frequency, small changes in the energy of the treatment beam 269 are achievable in real time. For example, the achieved energy of the treatment beam in the range of 30 to 330 MeV is adjustable at a level of less than 5, 2, 1, 0.5, 0.1, 0.05, or 0.01 MeV using the beam adjustment system 2420. Thus, the treatment beam 269 is optionally scanned along the z-axis and/or along a z-axis containing vector within the tumor 720 using the step of beam alteration 2422, described supra. Further, any imaging process of the tumor and/or the current position of the treatment beam 269, such as the positron emission tracking system, is optionally used as a dynamic feedback to the main controller 110 and/or the beam adjustment system 2420 to make one or more fine or sub-MeV adjustments of an applied energy of the treatment beam 269 with or without interrupting beam output, such as with use of the accelerator system 131, dumping the beam 2414, and/or loading the ring 124.

Multiple Beam Transport Lines

Figure 28:
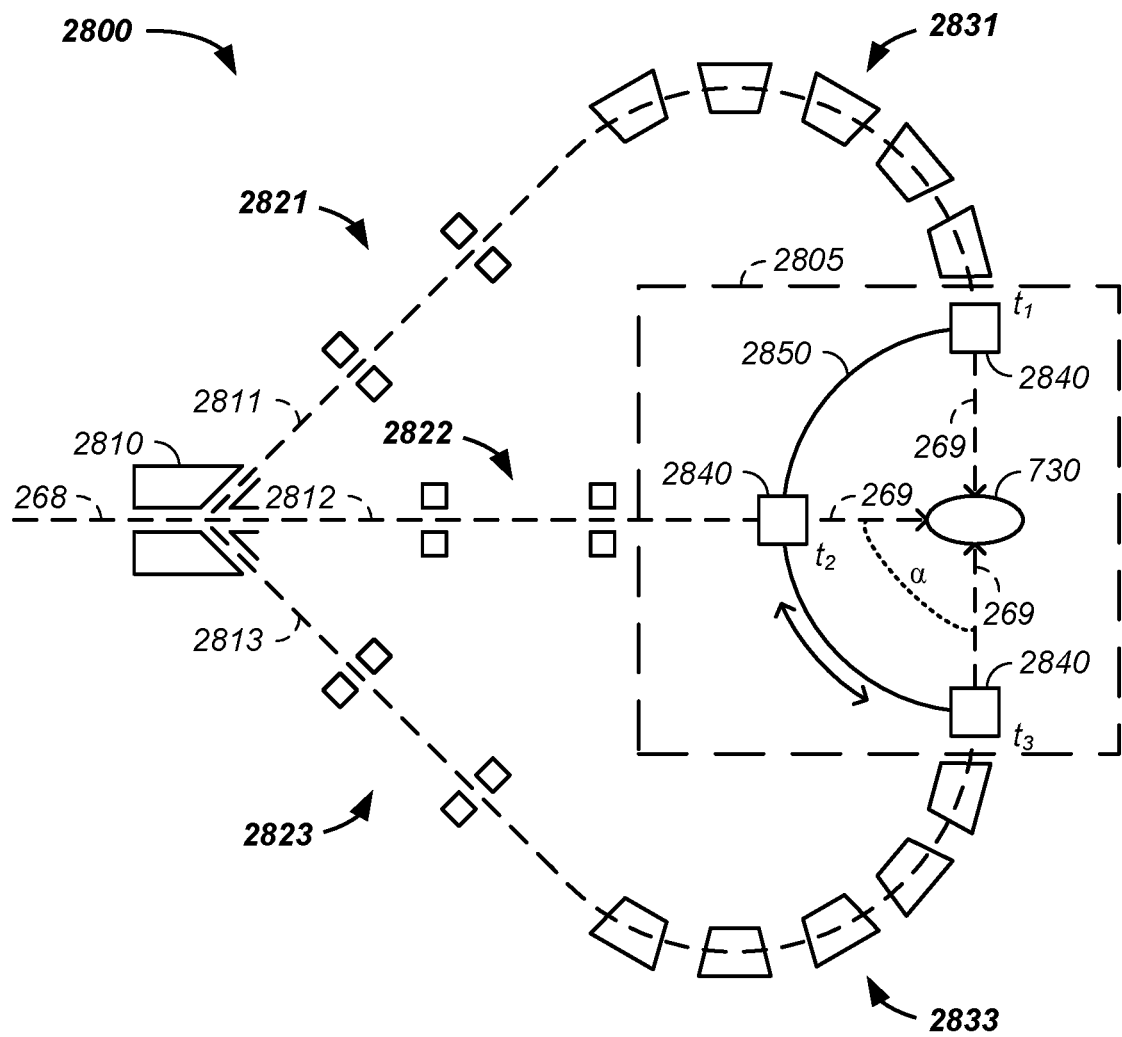
FIG. 28 illustrates a multi-beamline treatment system.
Figure 29:
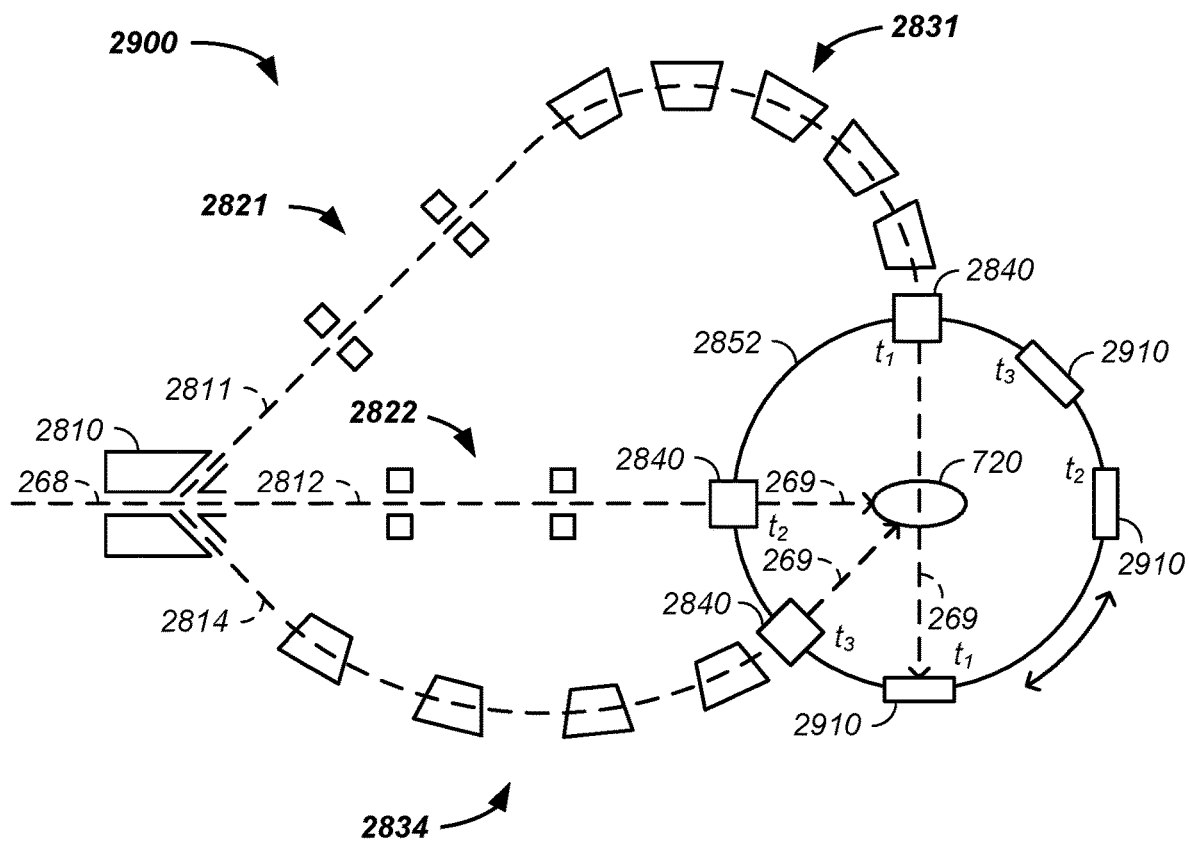
FIG. 29 illustrates a detachable/movable transport beam nozzle.

Referring now to FIG. 28 and FIG. 29, examples of a multi-beamline selectable nozzle positioning system 2800 and a multiple beamline imaging system 2900 of the beam transport system 135 are provided. Each of the two examples are further described, infra.

Still referring to FIG. 28, the beam path 268, in a section of the beam transport system 135 after the accelerator, is switched between n beams paths passing into a single treatment room 2805 using a beam path switching magnet 2810, where n is a positive integer of at least 2, such as 2, 3, 4, 5, 6, 7, or more. The single treatment room 2805 contains at least a terminal end of each of a plurality of treatment beam lines, separated at the beam path switching magnet 2810, and optionally contains the beam path switching magnet, beam focusing elements, and/or beam turning magnets. As illustrated, at a first time, $t_1$, the beam path 268 is switched to and transported by a first beam treatment line 2811. Similarly, at a second time, $t_2$, and third time, $t_3$, the beam path 268 is selected by the beam path switching magnet 2810 into a second beam treatment line 2812 and a third beam treatment line 2813, respectively. Herein, the beam treatment lines are also referred to as beam transport lines, such as when used to describe function and/or for imaging. Optionally, the single repositionable nozzle is moved between treatment rooms.

Still referring to FIG. 28, each of the beam treatment lines 2811, 2812, 2813, use at least some separate beam focusing elements and beam turning elements to, respectively, direct the beam path to the patient 730 from three directions. For example, the first beam treatment line 2811 uses a first set of focusing elements 2821 and/or a first set of turning magnets 2831, which are optionally of the same design as the bending magnet 132 or a similar design. Similarly, the third beam treatment line 2813 uses a third set of focusing elements 2823 and/or a third set of turning magnets 2833. As illustrated, the second beam treatment line 2812 uses a second set of focusing elements 2822 and no turning magnets. Generally, each treatment line uses any number of focusing elements and any number of turning magnets to guide the respective beam path to the patient 730 and/or the tumor 720, where at least one focusing element and/or turning magnet is unique to each of the treatment lines.

Still referring to FIG. 28, one or more of the beam treatment lines, such as the first beam treatment line 2811, the second beam treatment line 2812, and the third beam treatment line 2813, are statically positioned and use a single repositionable treatment nozzle 2840, which is an example of the nozzle system 146, described supra. More particularly, the single treatment nozzle 2840 optionally and preferably contains one or more of the elements of the nozzle system 146. Still more particularly, the repositionable treatment nozzle 2840 is repositioned to a current beam treatment line. For example, as illustrated the repositionable treatment nozzle 2840 is moved along an arc or pathway to a first terminus of the first beam treatment line 2811 at the first time, $t_1$, to direct the treatment beam 269 at the first time. Similarly, the repositionable treatment nozzle 2840 is repositioned, such as along an arc, circle, or path, to a second terminus position of the second beam treatment line 2812 at the second time, $t_2$, and to a third terminus position of the third beam treatment line 2813 at the third time, $t_3$. Herein, the repositioning path is illustrated as a rotatable nozzle positioning support 2850, where the rotatable nozzle positioning support rotates, such as under control of the main controller 110, about: a tumor position; a patient position; an isocentre of the multiple treatment beams 269 from the multiple beam treatment lines, respectively; and/or an axis normal to an axis aligned with gravity. The rotatable nozzle positioning support is optionally referred to as a nozzle gantry, where the nozzle gantry positions the repositionable treatment nozzle without movement of the individual beam treatment lines. The inventor notes that current treatment nozzles are large/bulky elements that could spatially conflict with one another and/or conflict with a patient positioning system if a separate treatment nozzle were implement on each of several beam treatment lines Still referring to FIG. 28, any of the beam treatment lines are optionally moved by a gantry, as described supra. However, the inventor notes that the nozzle is expensive compared to a beam treatment line, that design, engineering, use, and maintenance of a beamline moving gantry relative to a nozzle moving gantry is expensive, and that precision and accuracy of treatment is maintained or improved using the single repositionable treatment nozzle 2840. Hence, as illustrated, the first, second, and third beam treatment lines 2811, 2812, 2813 are statically positioned and the single repositionable treatment nozzle 2840 reduces cost.

Still referring to FIG. 28, each of the beam treatment lines, such as the first, second, and third beam treatment lines 2811, 2812, 2813, in combination with the single repositionable treatment nozzle 2840 yields a treatment beam 269 along any axis. As illustrated, the first beam treatment line 2811 yields a treatment beam 269 moving along an axis aligned with gravity imaging and/or treating the patient 730 from the top down. Further, as illustrated, the second beam treatment line 2812 is aligned along a horizontal axis and the third beam treatment line 2813 yields a treatment beam moving vertically upwards. Generally, the n treatment beams generate two or more treatment beams along any x/y/z-axes that each pass through a voxel of the tumor, the tumor 720, and/or the patient 730. As illustrated, the second beam treatment line 2812 and the third beam treatment line 2813 form an angle, a, through a crossing point of the two vectors in the patient 730 and preferably in the tumor 720. Generally, two beam treatment lines form an angle of greater than 2, 5, 10, 25, 40, 45, or 65 degrees and less than 180, 178, 175, 170, 155, 140, 135, or 115 degrees, such as 90±2, 5, 10, 25, or 45 degrees.

Still referring to FIG. 28, use of the repositionable treatment nozzle 2840, where the repositionable treatment nozzle 2840 is configured with the first axis control 143, such as a vertical control, and the second axis control 144, such as a horizontal control, along with beam transport lines leading to various sides of a patient allows the charged particle beam system 100 to operate without movement and/or rotation of the beam transport system 135 or the like and use of an associated beam transport gantry 960 or the like. More particularly, by treating the patient along two or more axes using the two or more bean transport lines described herein, a tumor irradiation plan is achievable using only the scanning control of one or more treatment nozzles without a necessity of a dynamically movable/rotatable beamline leading to a treatment position and an associated beamline gantry to move the movable/rotatable beamline.

Still referring to FIG. 28 and referring again to FIG. 29, the multi-beamline system selectable nozzle positioning system 2800 is further described and the multiple beamline imaging system 2900 is described. Generally, the multiple beamline imaging system 2900 optionally includes any of the elements of the multi-beamline system selectable nozzle positioning system 2800 and vise-versa.

Referring now to FIG. 29, the multiple beamline imaging system 2800 is illustrated with a fourth beam treatment line 2814. The fourth beam treatment line 2814 is guided by a fourth set of turning magnets 2834, that optionally and preferably contain beam focusing edge geometries, and optionally and preferably does not use independent focusing elements. As illustrated, the fourth beam treatment line 2814 generates a treatment beam 269 at a third time, $t_3$, that intersects a common voxel of the tumor 720, using at least one set of magnet conditions in the repositionable treatment nozzle 2840, where the common voxel of the tumor 720 is additionally treated by at least one other beamline, such as the second beam treatment line 2812 at a second time, $t_2$.

Referring still to FIG. 29, the multiple beamline imaging system 2900 is further illustrated with an imaging detector array 2910, which is an example of the detector array coupled to the scintillation material 710 in the tomography system, described supra. As illustrated, a rotatable detector array support 2852, which is optionally the rotatable nozzle positioning support, rotates around a point and/or a line to maintain relative positions of the repositionable treatment nozzle 2840 and the imaging detector array 2910 on opposite sides of the tumor 720 and/or patient 720 as a function of beam treatment line selection, which is optionally and preferably controlled by the main controller 110.

Referring again to FIG. 28 and FIG. 29, the repositionable treatment nozzle 2840 optionally contains any element of the scanning system 140 or targeting system; the first axis control 143, such as a vertical control; the second axis control 144, such as a horizontal control; the nozzle system 146; the beam control tray assembly 400 and/or function thereof; and/or a sheet, such as the first sheet 760, of the charged particle beam state determination system 750.

Imaging with Multiple Beam Energies

Optionally, the sample, patient, and/or tumor is imaged using two or more energies of the treatment beam 269. In analysis, resulting images or responses using a first beam energy and a second beam energy, of the two or more energies, are used in an analysis that removes at least one background signal or error from one or more voxels and/or pixels of the obtained images, such as by: taking a ratio of the two signals, calculating a difference between the two signals, by normalizing the images, and/or by comparing the images. By comparing images, tomograms, values, and/or signals obtained with at least two incident beam energies of the treatment beam 269, background interference is reduced and/or removed. In the case of imaging a tumor, the process of comparing signals with differing incident beam energies reduces and/or removes interference related to skin, collagen, elastic, protein, albumin, globulin, water, urea, glucose, hemoglobin, lactic acid, cholesterol, fat, blood, interstitial fluid, extracellular fluid, intracellular fluid, a sample constituent, temperature, and/or movement of the sample so that the intended element for imaging, such as the tumor, is enhanced in terms of at least one of resolution, accuracy, precision, identification, and spatial boundary. Residual energies are determined using a scintillation detector, as described supra, and/or an x-ray detector, as described infra.

Figure 30:
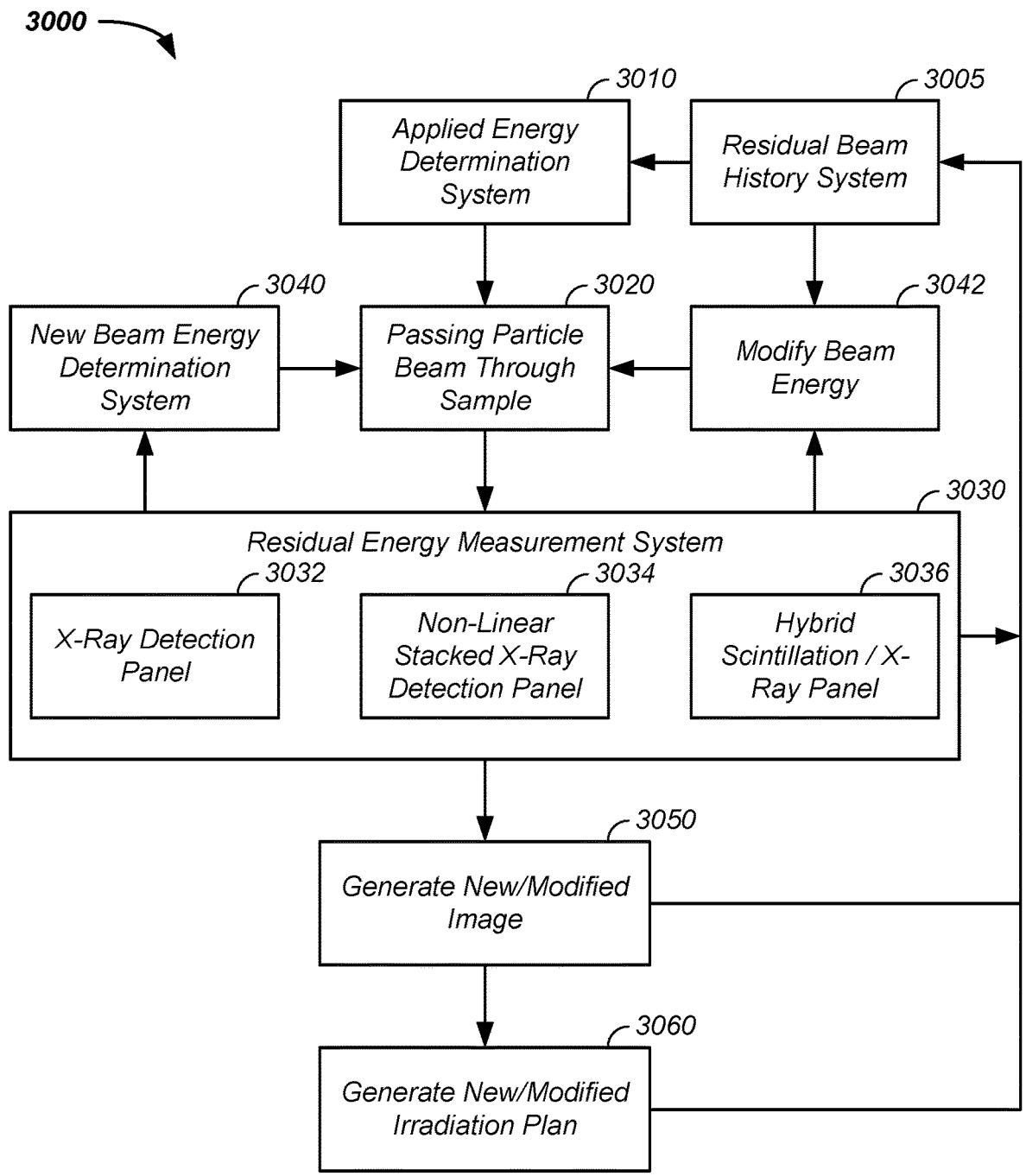
FIG. 30 illustrates a residual energy based imaging system.

Referring now to FIG. 30, a residual energy imaging system 3000 is described. Generally, the residual energy imaging system 3000 includes the processes of:
- passing charged particle beams through the sample 3020, the tumor 720, and/or the patient 730 as a function of beam energy, time, and/or position;
- using a residual energy measurement system 3030 to determine residual energy of each of the particles beams after passing through the sample, the tumor 720, and/or the patient 730; and
- generating a new/modified image 3050 of a volume probed with the charged particle beams.

Optionally, a residual beam history system 3005, such as determined using the above described steps, is used as an iterative input to an applied energy determination system 3010, which determines from a model and/or the residual beam history system 3005 a beam energy for passing through the sample resultant in a residual energy measured using the residual energy measurement system 3030. Optionally, the step of generating a new/modified image 3050 is used as input for a process of generating a new/modified irradiation plan 3060, such as for treating the tumor 720 of the patient 730. To further clarify the residual energy imaging system 3000 and without loss of generality, the residual energy imaging system 3000 is further described using four examples, infra.

Example I

Figure 31A:
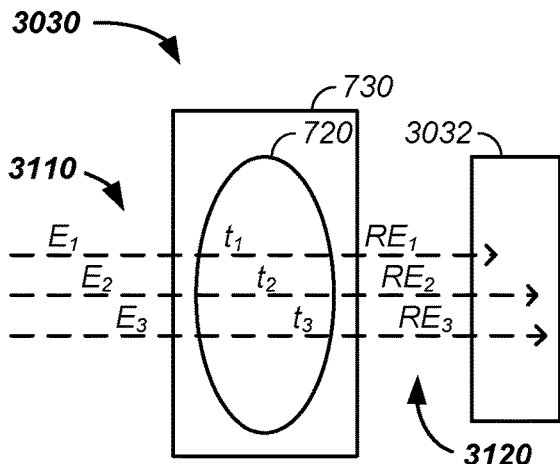
FIG. 31A illustrates a first residual energy system.
Figure 31B:
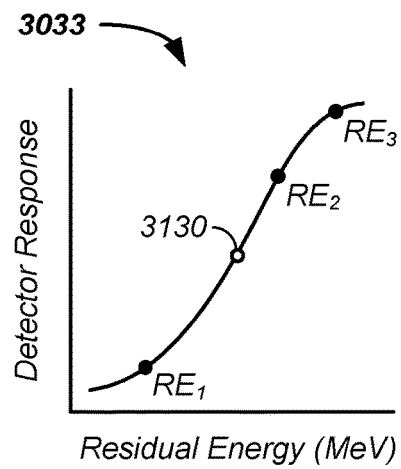
FIG. 31B illustrates a residual energy curved used in imaging.

Still referring to FIG. 30 and referring now to FIG. 31A and FIG. 31B, the residual energy measurement system 3030 uses an X-ray detection panel 3032 to measure residual energy of the charged particles after passing through the sample. More particularly, an X-ray detection element and/or a traditional X-ray detection element is used to measure a non-X-ray beam, such as a proton beam. Still more particularly, the X-ray detection panel optionally and preferably uses an X-ray sensitive material, a proton beam sensitive material, a digitized scan of an X-ray film, and/or a digital two-dimensional X-ray detection system.

Referring still to FIG. 30 and FIG. 31A, the residual energy measurement system 3030 sequentially applies positively charged particles, such as protons, at each of a set of energies 3110 to a given sample volume, where the set of energies 3110 contains 2, 3, 4, 5, 6, 7, 10, 15, or more energies. As illustrated, a first energy, $E_1$, is passed through the tumor 720 of the patient 730 at a first time, $t_1$, and a first residual energy, $RE_1$, is determined using the X-ray detection panel. The process is repeated, a second and third time, where, respectively, a second energy, $E_2$, and a third energy, $E_3$, are passed through the tumor 720 of the patient 730 at a second time, $t_2$, and a third time, $t_3$, and a second residual energy, $RE_2$, and a third residual energy, $RE_3$, are measured using the X-ray detection panel 3032 of the residual energy measurement system 3030. As illustrated, the first, second, and third incident energies are offset for clarity of presentation, whereas in practice the first, second, and third energies target the same volume of the sample. The energies of the set of energies 3110 are optionally predetermined or a new beam energy determination system 3040 is used to dynamically select subsequent energies of the set of energies 3110, such as to fill a missing position on a Gaussian curve fit of a response of the X-ray detection panel as a function of residual energy, such as an integral charge in Coulombs or nanoCoulombs as a function of residual megaelectron-Volts, such as further described infra.

Referring still to FIG. 31A and again to FIG. 31B, output of the X-ray detection panel 3032 is plotted against the determined residual energies, such as the first residual energy, $RE_1$, the second residual energy, $RE_2$, and the third residual energy, $RE_3$ and are fit with a curve, such as a Gaussian curve. The energy corresponding to a half-height, such as a full width at half-height position, of the Gaussian distribution 3130 is obtained and the continuous slowing down approximation yields the water equivalent thickness of the probed sample at the half-height position on the Gaussian distribution curve yielding a measured water equivalent thickness of the probed sample.

The process of sequentially irradiating an input point of a sample with multiple incident beam energies and determining respective residual beam energies is optionally and preferably repeated as a function of incident beam position on the sample, such as across an m×n array, where m and n are positive integers of at least 2, 3, 4, 5, 6, 7, or more. Resulting data is used in the step of generating a new/ modified image 3050 and, in the case of subsequent treatment, in the step of generating a new/modified irradiation plan 3060.

Example II

Figure 31C:
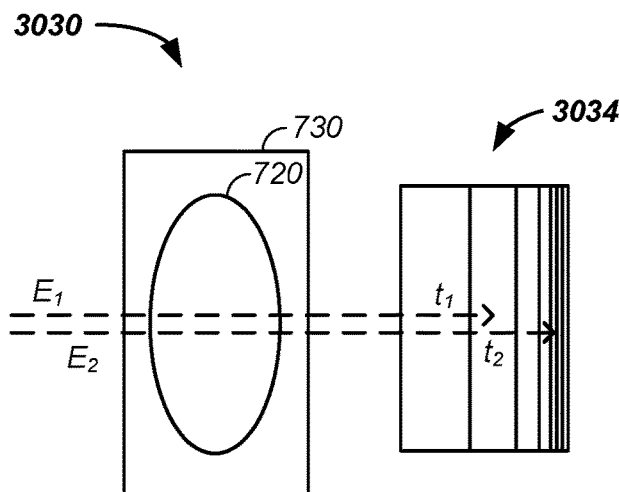
FIG. 31C illustrates a second residual energy determination system.

Referring again to FIG. 30 and referring now to FIG. 31C, the residual energy measurement system 3030 is described using a non-linear stacked X-ray detection panel 3034 and beam energy modification step 3042 in place of the X-ray detection panel 3032 and the new beam energy determination system step 3040. In this example, the single beam pencil shot system of Lomax as described in U.S. Pat. No. 8,461,559 is modified to use a second use of the single pencil beam shot, where the second shot terminates in a thinner detection layer, yielding enhanced precision and accuracy of the residual energy.

Particularly, referring now to FIG. 31C, the set of uniform thickness detector layers of Lomax is replaced with a non-uniform stack of detector layers 3034. As illustrated, the non-uniform stack of detector layers decrease in thickness as a function of residual energy location, such as progressive thicknesses of 1, ½, ¼, ⅛ units, to yield enhanced resolution of the Bragg peak energy through decreased error in the residual energy axis. Generally, a first beam at a first incident energy, $E_1$, is passed through the tumor 720 of the patient 730 at a first time, $t_1$, and the profile of the Bragg peak is determined using the non-uniform detector stack of detector layers 3034. Based upon the measured response profile, the beam energy modification step 3042 generates a second beam at a second energy, $E_2$, where the second beam terminates in the more precise thinner layers of the non-uniform stack of detector layers 3034, which yields a more robust Bragg peak profile due to a measured resultant rapid change in response over a set of small distances; the thinner detector layers. Generally, the first beam at the first beam energy, $E_1$, is used to measure a sample dependent response and to adjust the first beam energy to a second beam energy, $E_2$, to yield a more accurate measure of the sample. Generally, at least one layer of the non-linear stacked X-ray detection panel 3034 has a smaller thickness than a second layer of the non-linear stacked X-ray detection panel 3034, where the first layer is optionally positioned at a Bragg peak location based upon at least one earlier measurement of the sample and/or at least one prior calculation.

Example III

Figure 31D:
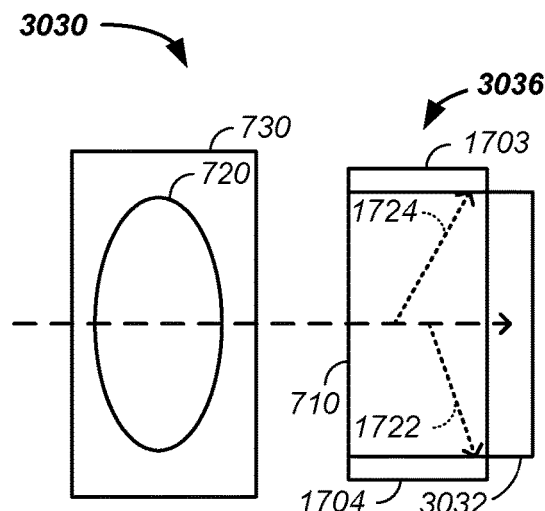
FIG. 31D illustrates a third residual energy measurement system.

Referring again to FIG. 30 and referring now to FIG. 31D, the residual energy measurement system 3030 is described using a hybrid detector system using a hybrid scintillation—X-ray panel 3036. Generally, the hybrid detector system uses one or more of the scintillation detectors, described supra, in combination with at least one of the X-ray detection panels 3032 used to detect a positively charged particle, as described supra. Generally, the scintillation material 710, upon passage of the positively charge particle in a residual beam path, emits photons, such as a first secondary photon 1722 and a second secondary photon 1724, which are detected using one or more scintillation detectors, such as the third detector array 1703 and the fourth detector array 1704, while the residual beam penetrates to an X-ray/proton/positively charged particle sensitive material, such as the X-ray detection panel 3032, which yields additional beam path information and/or beam intensity information of the residual beam and/or incident beam and indirectly the sample.

Example IV

A further example of the residual energy imaging system 3000 using the residual energy measurement system 3030 is provided.

Proton therapy benefits from an accurate prediction of applied ranges of energetic protons in human tissue, where the prediction converts X-ray CT Hounsfield Units (HUs) to proton relative stopping powers (RSPs), such as via an empirically derived look-up table specific to a given CT scanner. The conversion benefits from the patient tissue being well matched to a phantom in terms of chemical composition and density to the materials used in deriving the look-up table. The errors in matching the tissue, such as changes in patient geometry, weight change, tumor growth, and misalignment, are removed if the tissue itself is used as the phantom. Generally, the residual energy measurement system 3030 allows for a verification of integral stopping power of the patient as seen by a proton pencil immediately prior to treatment. The technique is referred to as Proton Transit Verification (PTV) Check. The integral relative stopping power along the entirety of a beam path is hereafter referred to as the water equivalent thickness (WET). The PTV Check provides the clinical team with information as to the accuracy of delivery of the treatment plan.

Measurement of the water equivalent thickness is optionally and preferably achieved using a delivery of proton pencil beams with large enough energies to completely traverse the patient and deposit a Bragg peak in a downstream radiation sensitive device. Herein, a dual-purpose flat panel imaging system is optionally used as the radiation detector, where the flat panel imaging system also forms part of the X-ray imaging/guidance system. The dual purpose flat panel imaging system is optionally mounted to a treatment couch, such as a patient positioning system, via the rotating ring nozzle system, described supra, or a rotating gantry. Optionally, the verification comprises delivery of a grid of pencil beams, such as using a predefined spacing and/or at the same angle, within the confines of the corresponding proton treatment field. As described in the first example, the water equivalent thickness is optionally determined at a given grid location via the process of sequential delivery of several low intensity pencil beams of increasing energy. A Gaussian distribution is fitted to a plot of detector signal as a function of pencil beam energy, as described supra. The energy corresponding to the half-height of the Gaussian distribution is obtained. The Continuous Slowing Down Approximation (CSDA) range of this energy provides the measured water equivalent thickness at this grid location. As described supra, a measured water equivalent thickness is compared to a predicted water equivalent thickness. The latter is calculated from the patient CT data, treatment plan parameters, and an energy specific system water equivalent thickness. The difference in measured and a predicted water equivalent thickness is optionally presented to the clinician via color coded dots overlaid on a patient image. Exemplary procedures follow.

Procedure 1: Creating a PTV Check Field
1. determine an extent of spot positions in the treatment field and place verification locations, such as at a predefined grid spacing, within the extent of the treatment field;
2. obtain an estimate of the water equivalent thickness along a ray tracing the central axis of the spots within the range probe field;

3. determine the proton kinetic energy, such as with a continuous slowing down approximation range corresponding to an estimated water equivalent thickness;
4. obtain a refined water equivalent thickness including the Gaussian profile of the pencil beam and multiple Coulomb scattering (MCS) effects;
5. recalculate the energy of the pencil beam based on the refined water equivalent thickness;
6. include additional pencil beams with CSDA ranges, such as those corresponding to −4, −2, 2, 4 mm water equivalent thickness around the nominal water equivalent thickness; and/or
7. set spot weights equal to the desired number of protons Procedure 2: Processing and Displaying Results of PTV Check Field After delivery of all spots in a pencil beam verification field, the treatment console calls an analysis process. The analysis process optionally comprises the following steps:
1. load the ion treatment plan;
2. process the current beam;
3. load flat panel output files for each spot;
4. integrated, for each spot, charges collected within a region of interest centered on the spot location in the panel;
5. integrated charge and pencil beam energy are passed to a Gaussian fitting function;
6. energy corresponding to the 50% drop of the Gaussian is determined from the fitted parameters;
7. the continuous slowing down approximation range of the energy obtained in Step 6 is used as the measured water equivalent thickness for this grid location; and/or
8. the measured water equivalent thickness is compared to the predicted water equivalent thickness.

Fiducial Marker

Fiducial markers and fiducial detectors are optionally used to locate, target, track, avoid, and/or adjust for objects in a treatment room that move relative to the nozzle or nozzle system 146 of the charged particle beam system 100 and/or relative to each other. Herein, for clarity of presentation and without loss of generality, fiducial markers and fiducial detectors are illustrated in terms of a movable or statically positioned treatment nozzle and a movable or static patient position. However, generally, the fiducial markers and fiducial detectors are used to mark and identify position, or relative position, of any object in a treatment room, such as a cancer therapy treatment room 1222. Herein, a fiducial indicator refers to either a fiducial marker or a fiducial detector. Herein, photons travel from a fiducial marker to a fiducial detector.

Herein, fiducial refers to a fixed basis of comparison, such as a point or a line. A fiducial marker or fiducial is an object placed in the field of view of an imaging system, which optionally appears in a generated image or digital representation of a scene, area, or volume produced for use as a point of reference or as a measure. Herein, a fiducial marker is an object placed on, but not into, a treatment room object or patient. Particularly, herein, a fiducial marker is not an implanted device in a patient. In physics, fiducials are reference points: fixed points or lines within a scene to which other objects can be related or against which objects can be measured. Fiducial markers are observed using a sighting device for determining directions or measuring angles, such as an alidade or in the modern era a digital detection system. Two examples of modern position determination systems are the Passive Polaris Spectra System and the Polaris Vicra System (NDI, Ontario, Canada).

Figure 32A:
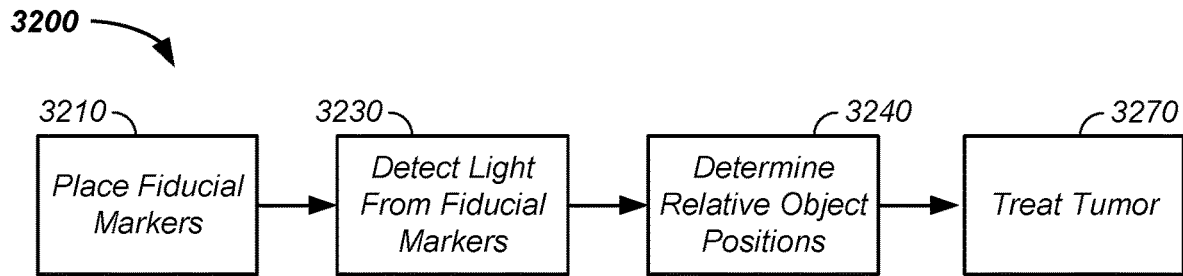
FIG. 32A illustrates a process of determining position of treatment room objects and FIG. 32B illustrates an iterative position tracking, imaging, and treatment system.

Referring now to FIG. 32A, use of a fiducial marker system 3200 is described. Generally, a fiducial marker is placed 3210 on an object, light from the fiducial marker is detected 3230, relative object positions are determined 3240, and a subsequent task is performed, such as treating a tumor 3270. For clarity of presentation and without loss of generality, non-limiting examples of uses of fiducial markers in combination with X-ray and/or positively charged particle tomographic imaging and/or treatment using positively charged particles are provided, infra.

Example I

Figure 33:
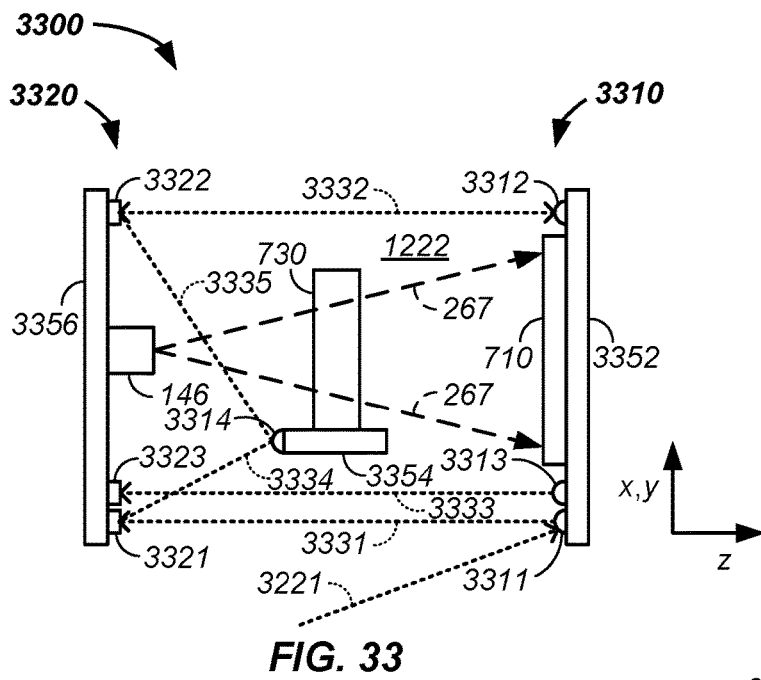
FIG. 33 illustrates a fiducial marker enhanced tomography imaging system.

Referring now to FIG. 33, a fiducial marker aided tomography system 3300 is illustrated and described. Generally, a set of fiducial marker detectors 3320 detects photons emitted from and/or reflected off of a set of fiducial markers 3310 and resultant determined distances and calculated angles are used to determine relative positions of multiple objects or elements, such as in the treatment room 1222.

Still referring to FIG. 33, initially, a set of fiducial markers 3310 are placed on one or more elements. As illustrated, a first fiducial marker 3311, a second fiducial marker 3312, and a third fiducial marker 3313 are positioned on a first, preferably rigid, support element 3352. As illustrated, the first support element 3352 supports a scintillation material 710. As each of the first, second, and third fiducial markers 3311, 3312, 3313 and the scintillation material 710 are affixed or statically positioned onto the first support element 3352, the relative position of the scintillation material 710 is known, based on degrees of freedom of movement of the first support element, if the positions of the first fiducial marker 3311, the second fiducial marker 3312, and/or the third fiducial marker 3313 is known. In this case, one or more distances between the first support element 3352 and a third support element 3356 are determined, as further described infra.

Still referring to FIG. 33, a set of fiducial detectors 3320 are used to detect light emitted from and/or reflected off one or more fiducial markers of the set of fiducial markers 3310. As illustrated, ambient photons 3221 and/or photons from an illumination source reflect off of the first fiducial marker 3311, travel along a first fiducial path 3331, and are detected by a first fiducial detector 3321 of the set of fiducial detectors 3320. In this case, a first signal from the first fiducial detector 3321 is used to determine a first distance to the first fiducial marker 3311. If the first support element 3352 supporting the scintillation material 710 only translates, relative to the nozzle system 146, along the z-axis, the first distance is sufficient information to determine a location of the scintillation material 710, relative to the nozzle system 146. Similarly, photons emitted, such as from a light emitting diode embedded into the second fiducial marker 3312 travel along a second fiducial path 3332 and generate a second signal when detected by a second fiducial detector 3322, of the set of fiducial detectors 3320. The second signal is optionally used to confirm position of the first support element 3352, reduce error of a determined position of the first support element 3352, and/or is used to determine extent of a second axis movement of the first support element 3352, such as tilt of the first support element 3352. Similarly, photons passing from the third fiducial marker 3313 travel along a third fiducial path 3333 and generate a third signal when detected by a third fiducial detector 3323, of the set of fiducial detectors 3320. The third signal is optionally used to confirm position of the first support element 3352, reduce error of a determined position of the first support element 3352, and/or is used to determine extent of a second or third axis movement of the first support element 3352, such as rotation of the first support element 3352.

If all of the movable elements within the treatment room 1222 move together, then determination of a position of one, two, or three fiducial markers, dependent on degrees of freedom of the movable elements, is sufficient to determine a position of all of the co-movable movable elements. However, optionally two or more objects in the treatment room 1222 move independently or semi-independently from one another. For instance, a first movable object optionally translates, tilts, and/or rotates relative to a second movable object. One or more additional fiducial markers of the set of fiducial markers 3310 placed on each movable object allows relative positions of each of the movable objects to be determined.

Still referring to FIG. 33, a position of the patient 730 is determined relative to a position of the scintillation material 710. As illustrated, a second support element 3354 positioning the patient 730 optionally translates, tilts, and/or rotates relative to the first support element 3352 positioning the scintillation material 710. In this case, a fourth fiducial marker 3314, attached to the second support element 3354 allows determination of a current position of the patient 730. As illustrated, a position of a single fiducial element, the fourth fiducial marker 3314, is determined by the first fiducial detector 3321 determining a first distance to the fourth fiducial marker 3314 and the second fiducial detector 3322 determining a second distance to the fourth fiducial marker 3314, where a first arc of the first distance from the first fiducial detector 3321 and a second arc of the second distance from the second fiducial detector 3322 overlap at a point of the fourth fiducial marker 3334 marking the position of the second support element 3352 and the supported position of the patient 730. Combined with the above described system of determining location of the scintillation material 710, the relative position of the scintillation material 710 to the patient 730, and thus the tumor 720, is determined.

Still referring to FIG. 33, one fiducial marker and/or one fiducial detector is optionally and preferably used to determine more than one distance or angle to one or more objects. In a first case, as illustrated, light from the fourth fiducial marker 3314 is detected by both the first fiducial detector 3321 and the second fiducial detector 3322. In a second case, as illustrated, light detected by the first fiducial detector 3321, passes from the first fiducial marker 3311 and the fourth fiducial marker 3314. Thus, (1) one fiducial marker and two fiducial detectors are used to determine a position of an object, (2) two fiducial markers on two elements and one fiducial detector is used to determine relative distances of the two elements to the single detector, and/or as illustrated and described below in relation to FIG. 35A, and/or (3) positions of two or more fiducial markers on a single object are detected using a single fiducial detector, where the distance and orientation of the single object is determined from the resultant signals. Generally, use of multiple fiducial markers and multiple fiducial detectors are used to determine or overdetermine positions of multiple objects, especially when the objects are rigid, such as a support element, or semi-rigid, such as a person, head, torso, or limb.

Still referring to FIG. 33, the fiducial marker aided tomography system 3300 is further described. As illustrated, the set of fiducial detectors 3320 are mounted onto the third support element 3356, which has a known position and orientation relative to the nozzle system 146. Thus, position and orientation of the nozzle system 146 is known relative to the tumor 720, the patient 730, and the scintillation material 710 through use of the set of fiducial markers 3310, as described supra. Optionally, the main controller 110 uses inputs from the set of fiducial detectors 3320 to: (1) dictate movement of the patient 730 or operator; (2) control, adjust, and/or dynamically adjust position of any element with a mounted fiducial marker and/or fiducial detector, and/or (3) control operation of the charged particle beam, such as for imaging and/or treating or performing a safety stop of the positively charged particle beam. Further, based on past movements, such as the operator moving across the treatment room 1222 or relative movement of two objects, the main controller is optionally and preferably used to prognosticate or predict a future conflict between the treatment beam 269 and the moving object, in this case the operator, and take appropriate action or to prevent collision of the two objects.

Example II

Figure 34:
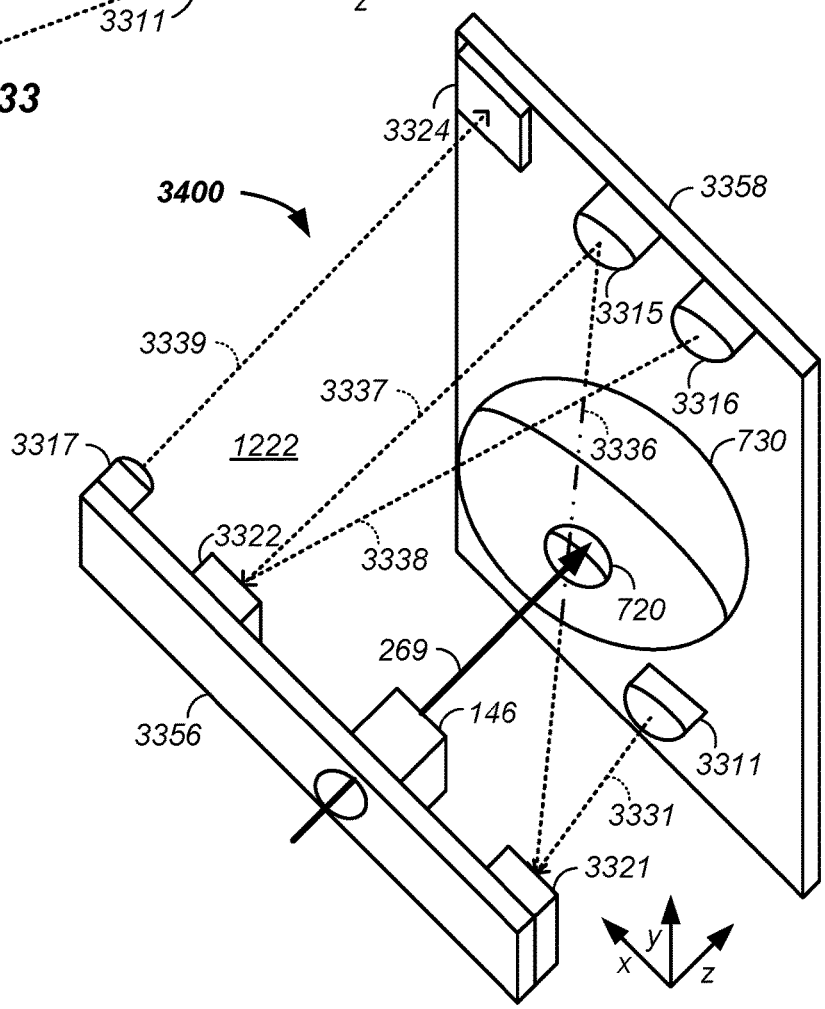
FIG. 34 illustrates a fiducial marker enhanced treatment system.

Referring now to FIG. 34, a fiducial marker aided treatment system 3400 is described. To clarify the invention and without loss of generality, this example uses positively charged particles to treat a tumor. However, the methods and apparatus described herein apply to imaging a sample, such as described supra.

Still referring to FIG. 34, four additional cases of fiducial marker—fiducial detector combinations are illustrated. In a first case, photons from the first fiducial marker 3311 are detected using the first fiducial detector 3321, as described in the previous example. However, photons from a fifth fiducial marker 3315 are blocked and prevented from reaching the first fiducial detector 3321 as a sixth fiducial path 3336 is blocked, in this case by the patient 730. The inventor notes that the absence of an expected signal, disappearance of a previously observed signal with the passage of time, and/or the emergence of a new signal each add information on existence and/or movement of an object. In a second case, photons from the fifth fiducial marker 3315 passing along a seventh fiducial path 3337 are detected by the second fiducial detector 3322, which illustrates one fiducial marker yielding a blocked and unblocked signal usable for finding an edge of a flexible element or an element with many degrees of freedom, such as a patient's hand, arm, or leg. In a third case, photons from the fifth fiducial marker 3315 and a sixth fiducial marker 3316, along the seventh fiducial path 3337 and an eighth fiducial path 3338 respectively, are detected by the second fiducial detector 3322, which illustrates that one fiducial detector optionally detects signals from multiple fiducial markers. In this case, photons from the multiple fiducial sources are optionally of different wavelengths, occur at separate times, occur for different overlapping periods of time, and/or are phase modulated. In a fourth case, a seventh fiducial marker 3317 is affixed to the same element as a fiducial detector, in this case the front surface plane of the third support element 3356. Also, in the fourth case, a fourth fiducial detector 3324, observing photons along a ninth fiducial path 3339, is mounted to a fourth support element 3358, where the fourth support element 3358 positions the patient 730 and tumor 720 thereof and/or is attached to one or more fiducial source elements.

Still referring to FIG. 34 the fiducial marker aided treatment system 3400 is further described. As described, supra, the set of fiducial markers 3310 and the set of fiducial detectors 3320 are used to determine relative locations of objects in the treatment room 1222, which are the third support element 3356, the fourth support element 3358, the patient 730, and the tumor 720 as illustrated. Further, as illustrated, the third support element 3356 comprises a known physical position and orientation relative to the nozzle system 146. Hence, using signals from the set of fiducial detectors 3320, representative of positions of the fiducial markers 3310 and room elements, the main controller 110 controls the treatment beam 269 to target the tumor 720 as a function of time, movement of the nozzle system 146, and/or movement of the patient 730.

Example III

Figure 35A:
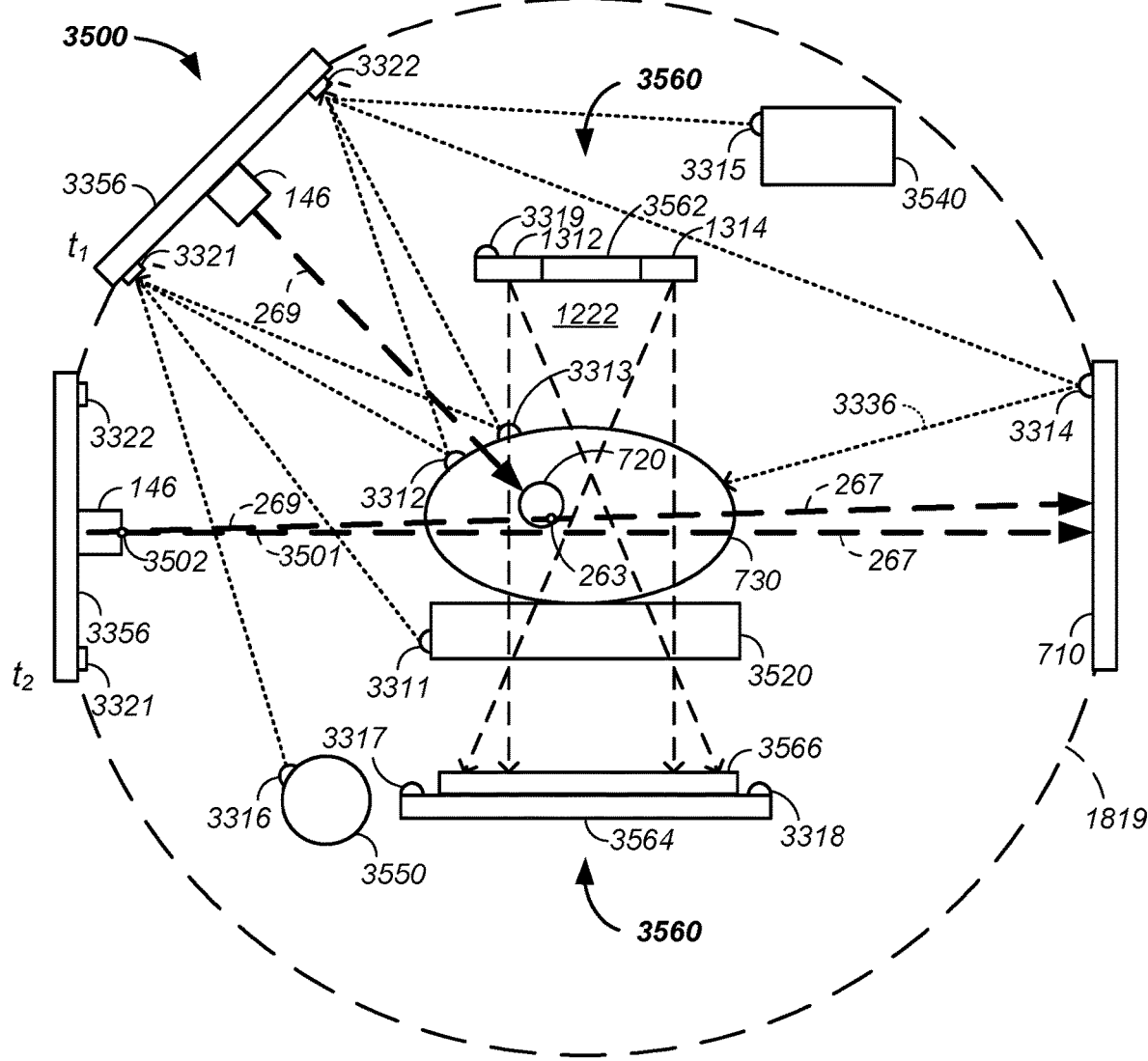
FIGS. 35(A-C) illustrate isocenterless cancer treatment systems.

Referring now to FIG. 35A, a fiducial marker aided treatment room system 3500 is described. Without loss of generality and for clarity of presentation, a zero vector 3501 is a vector or line emerging from the nozzle system 146 when the first axis control 143, such as a vertical control, and the second axis control 144, such as a horizontal control, of the scanning system 140 is turned off. Without loss of generality and for clarity of presentation, a zero point 3502 is a point on the zero vector 3501 at a plane of an exit face the nozzle system 146. Generally, a defined point and/or a defined line are used as a reference position and/or a reference direction and fiducial markers are defined in space relative to the point and/or line.

Six additional cases of fiducial marker—fiducial detector combinations are illustrated to further describe the fiducial marker aided treatment room system 3500. In a first case, the patient 730 position is determined. Herein, a first fiducial marker 3311 marks a position of a patient positioning device 3520 and a second fiducial marker 3312 marks a position of a portion of skin of the patient 730, such as a limb, joint, and/or a specific position relative to the tumor 720. In a second case, multiple fiducial markers of the set of fiducial markers 3310 and multiple fiducial detectors of said set of fiducial detectors 3320 are used to determine a position/relative position of a single object, where the process is optionally and preferably repeated for each object in the treatment room 1222. As illustrated, the patient 730 is marked with the second fiducial marker 3312 and a third fiducial marker 3313, which are monitored using a first fiducial detector 3321 and a second fiducial detector 3322. In a third case, a fourth fiducial marker 3314 marks the scintillation material 710 and a sixth fiducial path 3336 illustrates another example of a blocked fiducial path. In a fourth case, a fifth fiducial marker 3315 marks an object not always present in the treatment room, such as a wheelchair 3540, walker, or cart. In a sixth case, a sixth fiducial marker 3316 is used to mark an operator 3550, who is mobile and must be protected from an unwanted irradiation from the nozzle system 146.

Still referring to FIG. 35A, clear field treatment vectors and obstructed field treatment vectors are described. A clear field treatment vector comprises a path of the treatment beam 269 that does not intersect a non-standard object, where a standard object includes all elements in a path of the treatment beam 269 used to measure a property of the treatment beam 269, such as the first sheet 760, the second sheet 770, the third sheet 780, and the fourth sheet 790. Examples of non-standard objects or interfering objects include an arm of the patient couch, a back of the patient couch, and/or a supporting bar, such a robot arm. Use of fiducial indicators, such as a fiducial marker, on any potential interfering object allows the main controller 110 to only treat the tumor 720 of the patient 730 in the case of a clear field treatment vector. For example, fiducial markers are optionally placed along the edges or corners of the patient couch or patient positioning system or indeed anywhere on the patient couch. Combined with a-priori knowledge of geometry of the non-standard object, the main controller can deduce/calculate presence of the non-standard object in a current or future clear field treatment vector, forming a obstructed field treatment vector, and perform any of: increasing energy of the treatment beam 269 to compensate, moving the interfering non-standard object, and/or moving the patient 730 and/or the nozzle system 146 to a new position to yield a clear field treatment vector. Similarly, for a given determined clear filed treatment vector, a total treatable area, using scanning of the proton beam, for a given nozzle-patient couch position is optionally and preferably determined. Further, the clear field vectors are optionally and preferably predetermined and used in development of a radiation treatment plan.

Referring again to FIG. 32A, FIG. 33, FIG. 34, and FIG. 35A, generally, one or more fiducial markers and/or one or more fiducial detectors are attached to any movable and/or statically positioned object/element in the treatment room 1222, which allows determination of relative positions and orientation between any set of objects in the treatment room 1222.

Sound emitters and detectors, radar systems, and/or any range and/or directional finding system is optionally used in place of the source-photon-detector systems described herein.

2D-2D X-Ray Imaging

Still referring to FIG. 35A, for clarity of presentation and without loss of generality, a two-dimensional two-dimensional (2D-2D) X-ray imaging system 3560 is illustrated, which is representative of any source-sample-detector transmission based imaging system. As illustrated, the 2D-2D imaging system 3560 includes a 2D-2D source end 3562 on a first side of the patient 730 and a 2D-2D detector end 3564 on a second side, an opposite side, of the patient 730. The 2D-2D source end 3562 holds, positions, and/or aligns source imaging elements, such as: (1) one or more imaging sources; (2) the first imaging source 1312 and the second imaging source 1322; and/or (3) a first cone beam X-ray source 1392 and a second cone beam X-ray source 1394; while, the 2D-2D detector end 3564, respectively, holds, positions, and/or aligns: (1) one or more imaging detectors 3566; (2) a first imaging detector and a second imaging detector; and/or (3) a first cone beam X-ray detector and a second cone beam X-ray detector.

In practice, optionally and preferably, the 2D-2D imaging system 3560 as a unit rotates about a first axis around the patient, such as an axis of the treatment beam 269, as illustrated at the second time, $t_2$. For instance, at the second time, $t_2$, the 2D-2D source end 3562 moves up and out of the illustrated plane while the 2D-2D detector end 3564 moves down and out of the illustrated plane. Thus, the 2D-2D imaging system may operate at one or more positions through rotation about the first axis while the treatment beam 269 is in operation without interfering with a path of the treatment beam 269.

Optionally and preferably, the 2D-2D imaging system 3560 does not physically obstruct the treatment beam 269 or associated residual energy imaging beam from the nozzle system 146. Through relative movement of the nozzle system 146 and the 2D-2D imaging system 3560, a mean path of the treatment beam 269 and a mean path of X-rays from an X-ray source of the 2D-2D imaging system 3560 form an angle from 0 to 90 degrees and more preferably an angle of greater than 10, 20, 30, or 40 degrees and less than 80, 70, or 60 degrees. Still referring to FIG. 35A, as illustrated at the second time, $t_2$, the angle between the mean treatment beam and the mean X-ray beam is 45 degrees.

The 2D-2D imaging system 3560 optionally rotates about a second axis, such as an axis perpendicular to FIG. 35 and passing through the patient and/or passing through the first axis. Thus, as illustrated, as the exit port of the output nozzle system 146 moves along an arc and the treatment beam 269 enters the patient 730 from another angle, rotation of the 2D-2D imaging system 3560 about the second axis perpendicular to FIG. 35, the first axis of the 2D-2D imaging system 3560 continues to rotate about the first axis, where the first axis is the axis of the treatment beam 269 or the residual charged particle beam 267 in the case of imaging with protons.

Optionally and preferably, one or more elements of the 2D-2D X-ray imaging system 3560 are marked with one or more fiducial elements, as described supra. As illustrated, the 2D-2D detector end 3564 is configured with a seventh fiducial marker 3317 and an eighth fiducial marker 3318 while the 2D-2D source end 3562 is configured with a ninth fiducial marker 3319, where any number of fiducial markers are used.

In many cases, movement of one fiducial indicator necessitates movement of a second fiducial indicator as the two fiducial indicators are physically linked. Thus, the second fiducial indicator is not strictly needed, given complex code that computes the relative positions of fiducial markers that are often being rotated around the patient 730, translated past the patient 730, and/or moved relative to one or more additional fiducial markers. The code is further complicated by movement of non-mechanically linked and/or independently moveable obstructions, such as a first obstruction object moving along a first concentric path and a second obstruction object moving along a second concentric path. The inventor notes that the complex position determination code is greatly simplified if the treatment beam path 269 to the patient 730 is determined to be clear of obstructions, through use of the fiducial indicators, prior to treatment of at least one of and preferably every voxel of the tumor 720. Thus, multiple fiducial markers placed on potentially obstructing objects simplifies the code and reduces treatment related errors. Typically, treatment zones or treatment cones are determined where a treatment cone from the output nozzle system 146 to the patient 730 does not pass through any obstructions based on the current position of all potentially obstructing objects, such as a support element of the patient couch. As treatment cones overlap, the path of the treatment beam 269 and/or a path of the residual charged particle beam 267 is optionally moved from treatment cone to treatment cone without use of the imaging/treatment beam continuously as moved along an arc about the patient 730. A transform of the standard tomography algorithm thus allows physical obstructions to the imaging/treatment beam to be avoided.

Isocenterless System

The inventor notes that a fiducial marker aided imaging system, the fiducial marker aided tomography system 3300, and/or the fiducial marker aided treatment system 3400 are applicable in a treatment room 1222 not having a treatment beam isocenter, not having a tumor isocenter, and/or is not reliant upon calculations using and/or reliant upon an isocenter. Further, the inventor notes that all positively charged particle beam treatment centers in the public view are based upon mathematical systems using an isocenter for calculations of beam position and/or treatment position and that the fiducial marker aided imaging and treatment systems described herein do not need an isocenter and are not necessarily based upon mathematics using an isocenter, as is further described infra. In stark contrast, a defined point and/or a defined line are used as a reference position and/or a reference direction and fiducial markers are defined in space relative to the point and/or line.

Figure 35B:
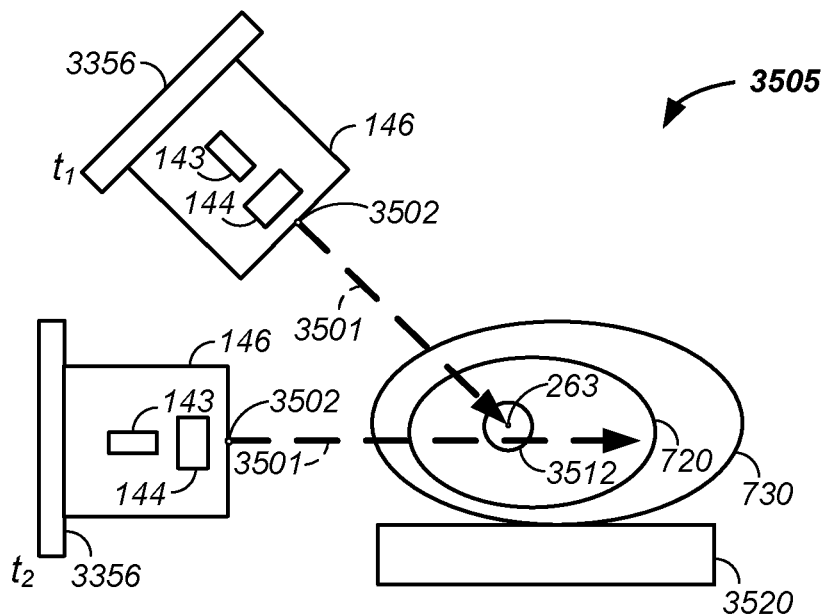

Traditionally, the isocenter 263 of a gantry based charged particle cancer therapy system is a point in space about which an output nozzle rotates. In theory, the isocenter 263 is an infinitely small point in space. However, traditional gantry and nozzle systems are large and extremely heavy devices with mechanical errors associated with each element. In real life, the gantry and nozzle rotate around a central volume, not a point, and at any given position of the gantry-nozzle system, a mean or unaltered path of the treatment beam 269 passes through a portion of the central volume, but not necessarily the single point of the isocenter 263. Thus, to distinguish theory and real-life, the central volume, referring now to FIG. 35B, is referred to herein as a mechanically defined isocenter volume 3512, where under best engineering practice the isocenter has a geometric center, the isocenter 263. Further, in theory, as the gantry-nozzle system rotates around the patient, the mean or unaltered lines of the treatment beam 269 at a first and second time, preferably all times, intersect at a point, the point being the isocenter 263, which is an unknown position. However, in practice the lines pass through the mechanically identified isocenter volume 3512. The inventor notes that in all gantry supported movable nozzle systems, calculations of applied beam state, such as energy, intensity, and direction of the charged particle beam, are calculated using a mathematical assumption of the point of the isocenter 263. The inventor further notes, that as in practice the treatment beam 269 passes through the mechanically defined isocenter volume 3512 but misses the isocenter 263, an error exists between the actual treatment volume and the calculated treatment volume of the tumor 720 of the patient 730 at each point in time. The inventor still further notes that the error results in the treatment beam 269: (1) not striking a given volume of the tumor 720 with the prescribed energy and/or (2) striking tissue outside of the tumor. Mechanically, this error cannot be eliminated, only reduced. However, use of the fiducial markers and fiducial detectors, as described supra, removes the constraint of using an unknown position of the isocenter 263 to determine where the treatment beam 269 is striking to fulfill a doctor provided treatment prescription as the actual position of the patient positioning system, tumor 720, and/or patient 730 is determined using the fiducial markers and output of the fiducial detectors with no use of the isocenter 263, no assumption of an isocenter 263, and/or no spatial treatment calculation based on the isocenter 263. Rather, a physically defined point and/or line, such as the zero point 3502 and/or the zero vector 3501, in conjunction with the fiducials are used to: (1) determine position and/or orientation of objects relative to the point and/or line and/or (2) perform calculations, such as a radiation treatment plan.

Referring again to FIG. 32A and referring again to FIG. 35A, optionally and preferably, the task of determining the relative object positions 3240 uses a fiducial element, such as an optical tracker, mounted in the treatment room 1222, such as on the gantry or nozzle system, and calibrated to a "zero" vector 3501 of the treatment beam 269, which is defined as the path of the treatment beam when electromagnetic and/or electrostatic steering of one or more final magnets in the beam transport system 135 and/or an output nozzle system 146 attached to a terminus thereof is/are turned off. Referring again to FIG. 35B, the zero vector 3501 is a path of the treatment beam 269 when the first axis control 143, such as a vertical control, and the second axis control 144, such as a horizontal control, of the scanning system 140 is turned off. A zero point 3502 is any point, such as a point on the zero vector 3501. Herein, without loss of generality and for clarity of presentation, the zero point 3502 is a point on the zero vector 3501 crossing a plane defined by a terminus of the nozzle of the nozzle system 146. Ultimately, the use of a zero vector 3501 and/or the zero point 3502 is a method of directly and optionally actively relating the coordinates of objects, such as moving objects and/or the patient 730 and tumor 720 thereof, in the treatment room 1222 to one another; not passively relating them to an imaginary point in space such as a theoretical isocenter than cannot mechanically be implemented in practice as a point in space, but rather always as an a isocenter volume, such as an isocenter volume including the isocenter point in a well-engineered system. Examples further distinguish the isocenter based and fiducial marker based targeting system.

Example I

Referring now to FIG. 35B, an isocenterless system 3505 of the fiducial marker aided treatment room system 3500 of FIG. 35A is described. As illustrated, the nozzle/nozzle system 146 is positioned relative to a reference element, such as the third support element 3356. The reference element is optionally a reference fiducial marker and/or a reference fiducial detector affixed to any portion of the nozzle system 146 and/or a rigid, positionally known mechanical element affixed thereto. A position of the tumor 720 of the patient 730 is also determined using fiducial markers and fiducial detectors, as described supra. As illustrated, at a first time, $t_1$, a first mean path of the treatment beam 269 passes through the isocenter 263. At a second time, $t_2$, resultant from inherent mechanical errors associated with moving the nozzle system 146, a second mean path of the treatment beam 269 does not pass through the isocenter 263. In a traditional system, this would result in a treatment volume error. However, using the fiducial marker based system, the actual position of the nozzle system 146 and the patient 730 is known at the second time, $t_2$, which allows the main controller to direct the treatment beam 269 to the targeted and prescription dictated tumor volume using the first axis control 143, such as a vertical control, and the second axis control 144, such as a horizontal control, of the scanning system 140. Again, since the actual position at the time of treatment is known using the fiducial marker system, mechanical errors of moving the nozzle system 146 are removed and the x/y-axes adjustments of the treatment beam 269 are made using the actual and known position of the nozzle system 146 and the tumor 720, in direct contrast to the x/y-axes adjustments made in traditional systems, which assume that the treatment beam 269 passes through the isocenter 263. In essence: (1) the x/y-axes adjustments of the traditional targeting systems are in error as the unmodified treatment beam 269 is not passing through the assumed isocenter and (2) the x/y-axes adjustments of the fiducial marker based system know the actual position of the treatment beam 269 relative to the patient 730 and the tumor 720 thereof, which allows different x/y-axes adjustments that adjust the treatment beam 269 to treat the prescribed tumor volume with the prescribed dosage.

Example II

Figure 35C:
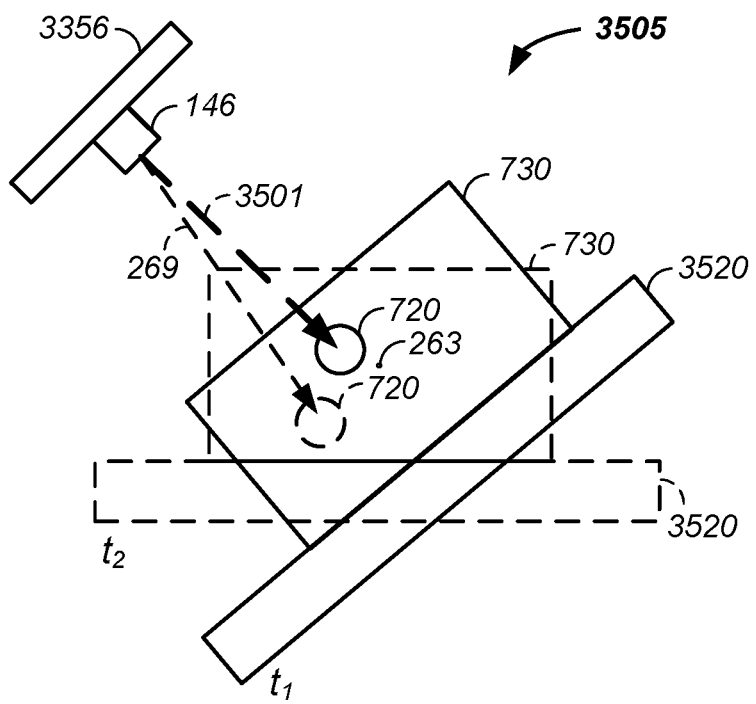

Referring now to FIG. 35C an example is provided that illustrates errors in an isocenter 263 with a fixed beamline position and a moving patient positioning system. As illustrated, at a first time, $t_1$, the mean/unaltered treatment beam path 269 passes through the tumor 720, but misses the isocenter 263. As described, supra, traditional treatment systems assume that the mean/unaltered treatment beam path 269 passes through the isocenter 263 and adjust the treatment beam to a prescribed volume of the tumor 720 for treatment, where both the assumed path through the isocenter and the adjusted path based on the isocenter are in error. In stark contrast, the fiducial marker system: (1) determines that the actual mean/unaltered treatment beam path 269 does not pass through the isocenter 263, (2) determines the actual path of the mean/unaltered treatment beam 269 relative to the tumor 720, and (3) adjusts, using a reference system such as the zero line 3501 and/or the zero point 3502, the actual mean/unaltered treatment beam 269 to strike the prescribed tissue volume using the first axis control 143, such as a vertical control, and the second axis control 144, such as a horizontal control, of the scanning system 140. As illustrated, at a second time, $t_2$, the mean/unaltered treatment beam path 269 again misses the isocenter 263 resulting in treatment errors in the traditional isocenter based targeting systems, but as described, the steps of: (1) determining the relative position of: (a) the mean/unaltered treatment beam 269 and (b) the patient 730 and tumor 720 thereof and (2) adjusting the determined and actual mean/unaltered treatment beam 269, relative to the tumor 720, to strike the prescribed tissue volume using the first axis control 143, the second axis control 144, and energy of the treatment beam 269 are repeated for the second time, $t_2$, and again through the $n^{th}$ treatment time, where n is a positive integer of at least 5, 10, 50, 100, or 500.

Referring again to FIG. 33 and FIG. 34, generally at a first time, objects, such as the patient 730, the scintillation material 710, an X-ray system, and the nozzle system 146 are mapped and relative positions are determined. At a second time, the position of the mapped objects is used in imaging, such as X-ray and/or proton beam imaging, and/or treatment, such as cancer treatment. Further, an isocenter is optionally used or is not used. Still further, the treatment room 1222 is, due to removal of the beam isocenter knowledge constraint, optionally designed with a static or movable nozzle system 146 in conjunction with any patient positioning system along any set of axes as long as the fiducial marking system is utilized.

Figure 32B:
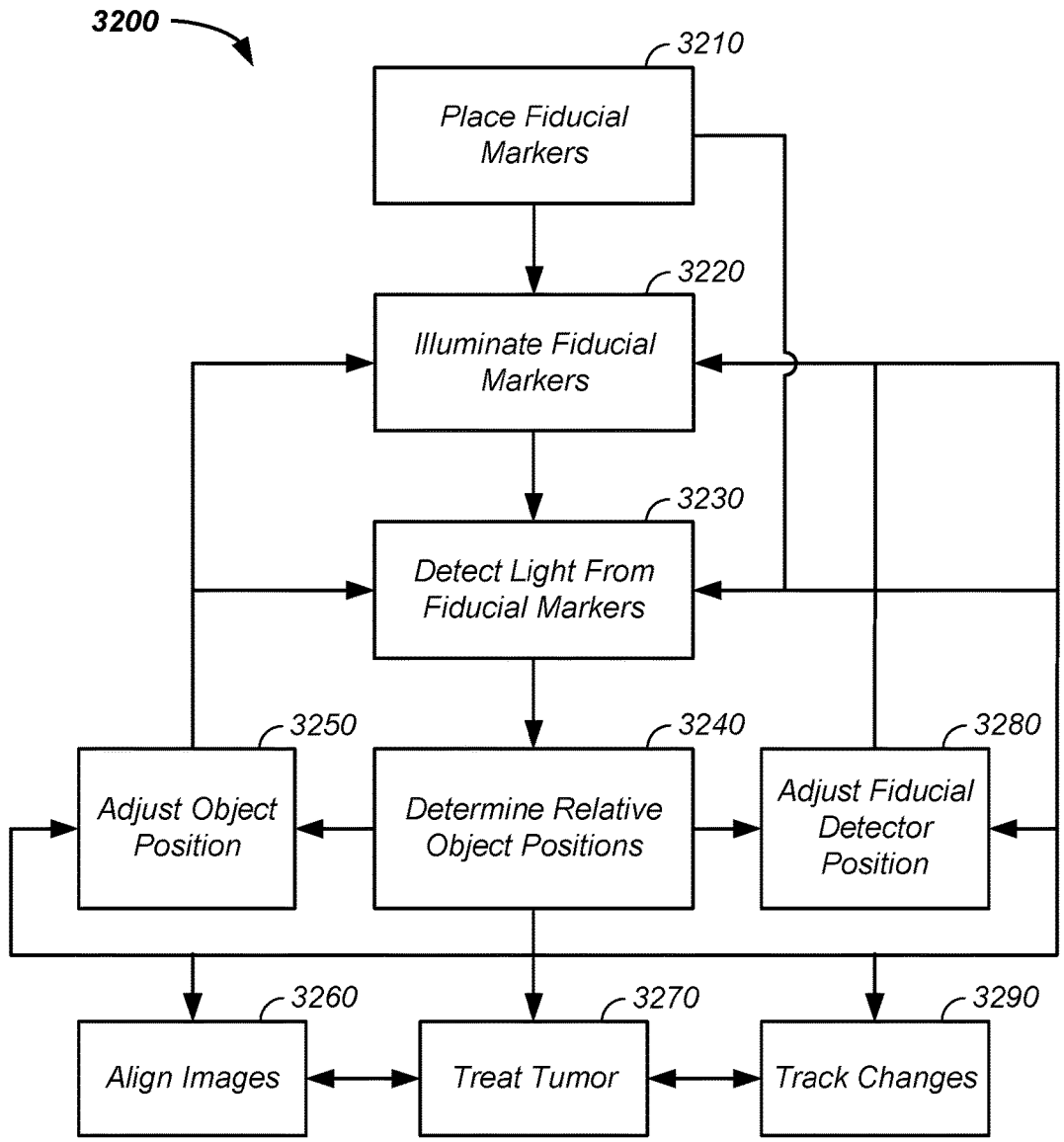

Referring now to FIG. 32B, optional uses of the fiducial marker system 3200 are described. After the initial step of placing the fiducial markers 3210, the fiducial markers are optionally illuminated 3220, such as with the ambient light or external light as described above. Light from the fiducial markers is detected 3230 and used to determine relative positions of objects 3240, as described above. Thereafter, the object positions are optionally adjusted 3250, such as under control of the main controller 110 and the step of illuminating the fiducial markers 3220 and/or the step of detecting light from the fiducial markers 3230 along with the step of determining relative object positions 3240 is iteratively repeated until the objects are correctly positioned. Simultaneously or independently, fiducial detectors positions are adjusted 3280 until the objects are correctly placed, such as for treatment of a particular tumor voxel. Using any of the above steps: (1) one or more images are optionally aligned 3260, such as a collected X-ray image and a collected proton tomography image using the determined positions; (2) the tumor 720 is treated 3270; and/or (3) changes of the tumor 720 are tracked 3290 for dynamic treatment changes and/or the treatment session is recorded for subsequent analysis.

The use of fiducials related to the zero line 3501 and/or the zero point 3502 is further described. Generally, position of a set of fiducial elements, which are also referred to herein as a fiducial indicators, are determined relative to a line and/or point, such as the zero line 3501 and/or the zero point 3502. Without loss of generality, a non-limiting example is used to further clarify the co-use of fiducials and a known reference position.

Example I

Figure 36A:
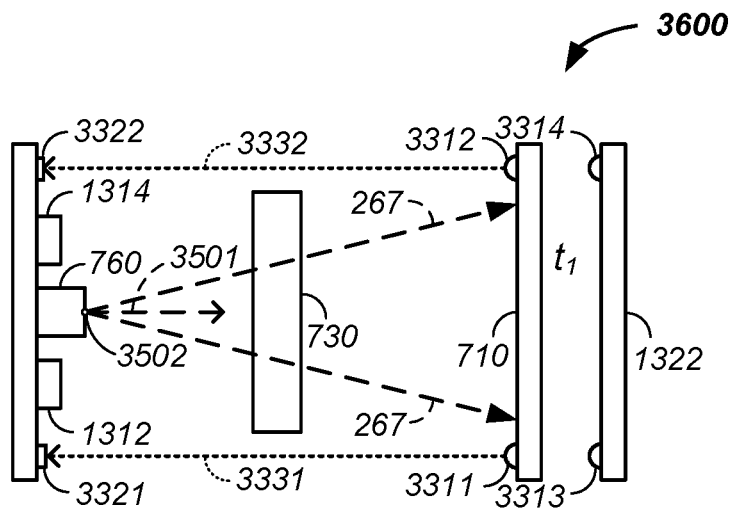
FIG. 36A and FIG. 36B illustrate a dual-imaging system.

Referring now to FIG. 36A, an example of the isocenterless system 3505 is provided in a dual proton imaging/X-ray imaging system 3600. In this example, the exit nozzle, nozzle system 146, the zero line 3501, and the zero point 3502 are defined, as described supra. As the exit nozzle is mechanically affixed to the first fiducial detector 3321 and the second fiducial detector 3321, the relative positions of the two fiducial detectors 3321, 3322 to the exit nozzle system 146 are known, as described supra. Further, the first fiducial marker 3311 and the second fiducial marker 3312, attached to the scintillation material 710, in combination with the first and second fiducial detectors 3321, 3322 and their relationship to the exit nozzle or nozzle system 146 are used determine the position of the scintillation material 710 relative to the patient, where the patient position is identified using further fiducial markers as described supra. Hence, the treatment beamline 269, which is the zero line 3501 when the first and second axis controls 143, 144 are turned off, is precisely known relative to the patient 730 and scintillation material 710. Thus, using the residual charged particle beam 267, images generated from the scintillation material 710 are aligned to the patient 730 without knowledge of or even existence of an isocenter point 263.

Example II

Figure 36B:
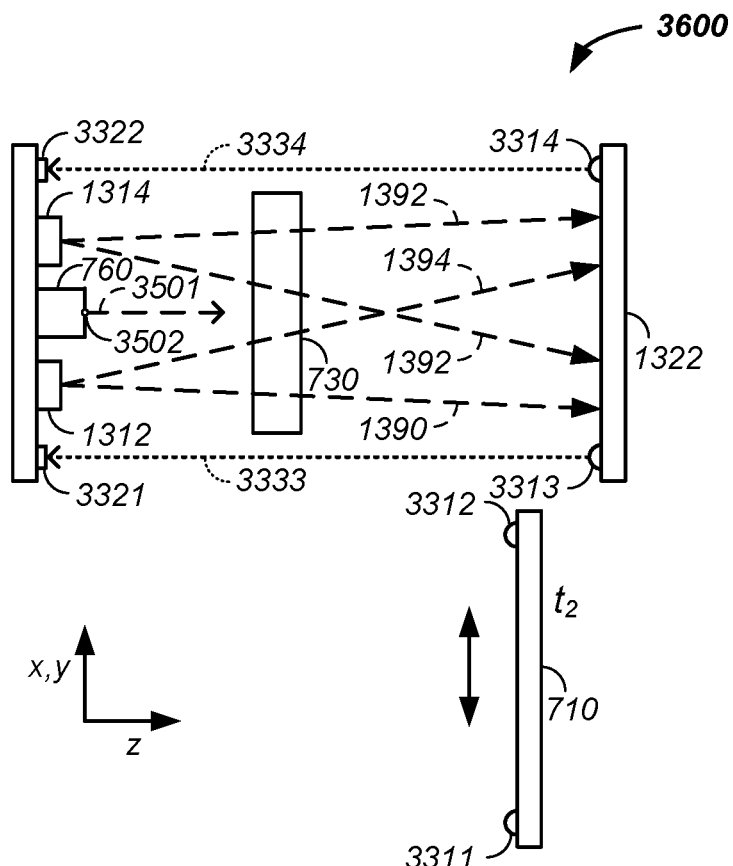

Referring still to FIG. 36A and referring now to FIG. 36B, an example of use of fiducial indicators on movable objects relative to the zero line 3501 and the zero point 3502 is provided. As illustrated in FIG. 36A, the scintillation material 710 blocks particles, emitted as waves from the first imaging source 1312, such as a first X-ray source, and the second imaging source 1314, such as a second X-ray source, from reaching the first detector array 1322 at a first time, t₁. At a second time, t₁, after retracting or sliding the scintillation material 710 out of the path of X-rays, a position of the first detector array 1322 relative to the patient 730, the exit nozzle or nozzle system 146, the first imaging source 1312, and the second imaging source 1314 is determined using fiducial indicators, as described supra. Hence, two 2-D X-ray images of the patient 730 and tumor thereof 720 are collected using: (1) the first imaging source 1312 and a first cone beam 1392, (2) a second imaging source 1314 and a second cone beam 1394, and (3) the first detector array 1322 allowing determination of a current position of the tumor 720 relative to the zero line 3501 of the treatment beam 269, even when the exit nozzle or nozzle system 146 is moved or is moving, without knowledge of or even existence of an isocenter point 263. Particularly, the described isocenterless system 3505 optionally tracks a position of the patient 730 and tumor 720 thereof relative to the treatment beam 269 using the zero line 3501.

Simultaneous/Single Patient Position X-Ray and Proton Imaging

Figure 37A:
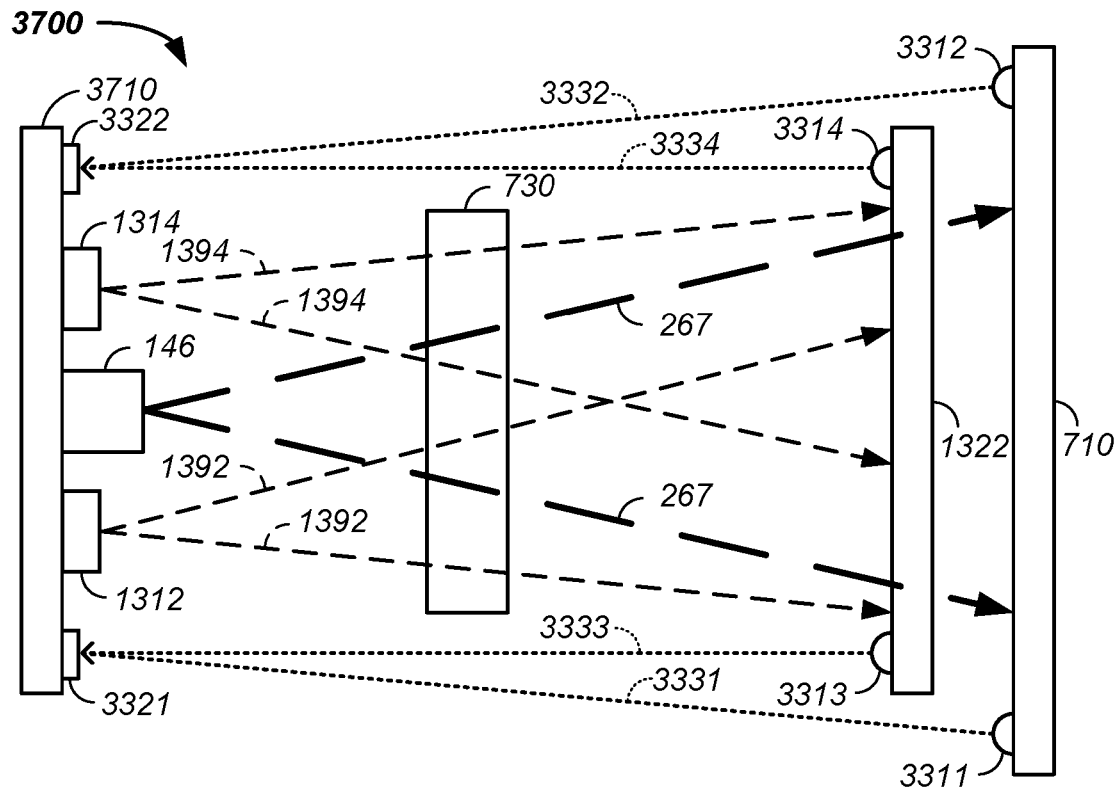
FIG. 37A and FIG. 37B illustrate common path simultaneous imaging systems.

Referring now to FIG. 37A, a simultaneous/single patient position X-ray and proton imaging system 3700 is illustrated. Generally, higher energy particles pass through a lower energy detector, such as an X-ray detector, to a higher energy detector, such as a proton scintillation detector or carbon ion scintillation detector. Simultaneously and/or without moving the lower energy detector, lower energy waves, such as X-rays, are detected using the lower energy detector, such as the X-ray detector positioned in front of the high energy detector. Herein, for clarity of presentation and without loss of generality, X-rays and protons are used to illustrate the lower and higher energy waves/particles, respectively, used to image the sample, such as the tumor 720 of the patient 730.

Example I

In a first example, the patient 730 is positioned, such as through use of a couch or patient positioning system, between the sources and the detectors.

Still referring to FIG. 37A, as illustrated, the patient 730 is positioned between a source element support system 3710, such as described above for holding an X-ray system element for producing, delivering, and/or targeting X-rays through the patient 730 to the first detector 1322, such as an X-ray film, digital X-ray detector, or two-dimensional detector. As illustrated, the first imaging source 1312, such as a first X-ray source or first cone beam X-ray source, and the second imaging source 1314, such as a second cone beam X-ray source, provide a first cone beam 1392 and a second cone beam 1394, respectively, that, after passing through the patient 730, are detected using one of more X-ray detectors, such as the first detector 1322.

Still referring to FIG. 37A, as illustrated, the patient 730 is positioned, optionally and preferably at the same position used for the X-ray imaging, between the source element support system 3710, such as described above for holding the nozzle system 146 and the scintillation material 710. The nozzle system 146 is used for delivering and/or targeting protons through the patient 730, where the residual charged particle beam transmits through the first detector 1322 to the second detector, such as the scintillation material 710.

Still referring to FIG. 37A, the two preceding paragraphs describe an X-ray imaging system and a proton imaging system. The X-ray imaging system and the proton imaging system: (1) are optionally used simultaneously, such as during time scales shorter than 1 msec, a patient twitch, or 1 sec; (2) are used at separate times without need to move the first detector 1332, the X-ray detector, out of a path of the residual charged particle beam 267 as the residual charged particle beam 267 has sufficient energy to pass through the X-ray detector; (3) generate one or more X-ray images that are optionally combined with one or more proton images; and/or (4) used to collect individual frames/slices of, respective, X-ray and proton tomography images.

Example II

Still referring to FIG. 37A, an X-ray detector is optionally used to detect positively charged particles, such as protons. As the mass of a proton is extremely large compared to an X-ray, a resolution enhancement over a traditional X-ray image is obtained as the protons scatter less and/or differently than X-rays in transmittance through the patient 730.

Example III

Still referring to FIG. 37A, the X-ray detector is optionally used to simultaneously detect X-rays and protons, yielding a physically obtained X-ray/proton fused image by the response of the detector element itself, not necessitating a post processing step combining a first image, such as an X-ray image with a second image, such as a proton image.

Example IV

Still referring to FIG. 37A, optionally and preferably fiducials, such as described supra, are used to determine the relative position of the source elements, the patient 730, and the detector elements, where relative positions are used for targeting, imaging, and/or aligning resulting images.

Example V

Figure 37B:
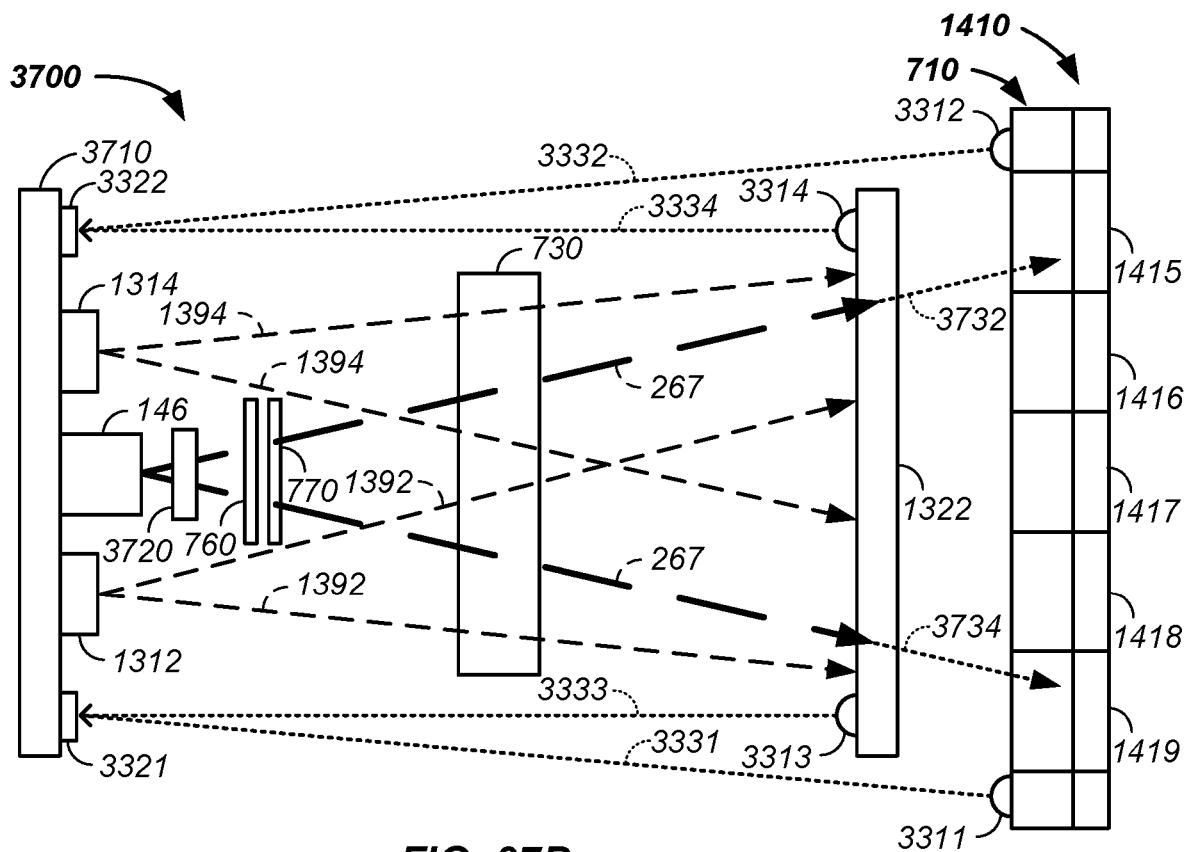

Referring now to FIG. 37B, the simultaneous/single patient position X-ray and proton imaging system 3700 is further illustrated with optional beam position determination sheets, such as the first sheet 760 and the second sheet 770 described above, which allow for a more precise, and with the use of fiducials, more accurate determination of paths of individual protons through the patient 730 and tumor 720 thereof.

Example VI

Referring still to FIG. 37B, the simultaneous/single patient position X-ray and proton imaging system 3700 is further illustrated with an optional positively charged particle beam diffusing element 3720. As described above, a single proton is transmitted to the scintillation material 710 at a given, typically very short, time period, which allows calculation of a path of the proton through the patient 730. At the next short period of time, the process is repeated targeting another volume of the patient 730. However, with a diffusing element 3720, the narrow diameter proton beam, a necessity for a small synchrotron, is expanded or diffused by the diffusing element 3720, so that on average, the single proton calculations still work, but the system is multiplexed to allow detection of multiple protons simultaneously using the beam determination sheets and position of scintillation on the scintillation material 710, which is optionally enhanced using the multiplexed scintillation detector 1600, where elements of the array of scintillation sections 1610 are optionally physically separated. The positively charged particle beam diffusing element 3720 is optionally a proton dense material, such as a plastic, and/or a material changing direction of an incident particle. The positively charged particle beam optionally and preferably transmits through a section of the positively charged particle beam diffusing element 3720 comprising a set of atoms, where at least 10, 20, 30, 40, or 50 percent of said set of atoms comprise a form of hydrogen. With or without the diffusing element 3720, beam expander, or scattering material. Optionally, the nozzle system 146, also referred to as an exit nozzle and/or particle beam exit nozzle, the scanning system 140, first axis control 143, the vertical control, the second axis control 144, and/or the horizontal control are rapidly varied to distribute the treatment beam 269, and the resultant residual charged particle beam 267, to perform pseudo multi-plex imaging, where the pseudo multi-plex imaging is not simultaneously irradiating separate quadrants of a detector array, but rather rapidly scanning/switching between irradiation positions.

Multiplexed Proton Imaging

Figure 38A:
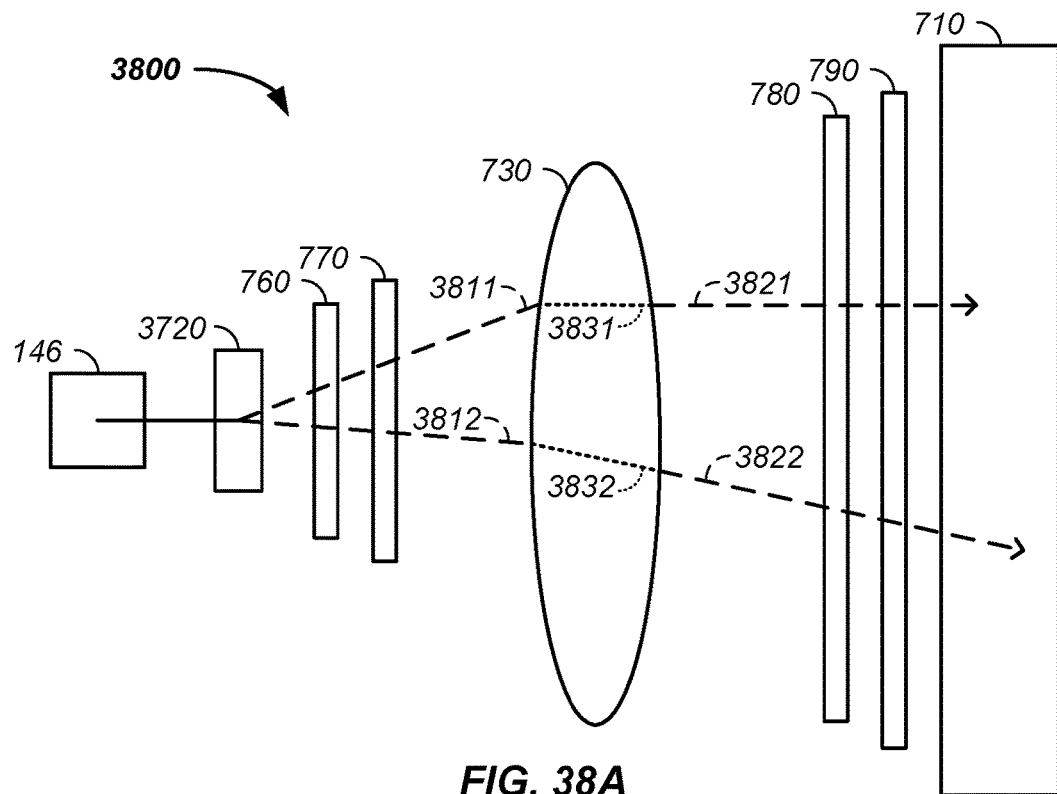
FIG. 38A and FIG. 38B illustrate simultaneously tracking multiple independent beam paths.
Figure 38B:
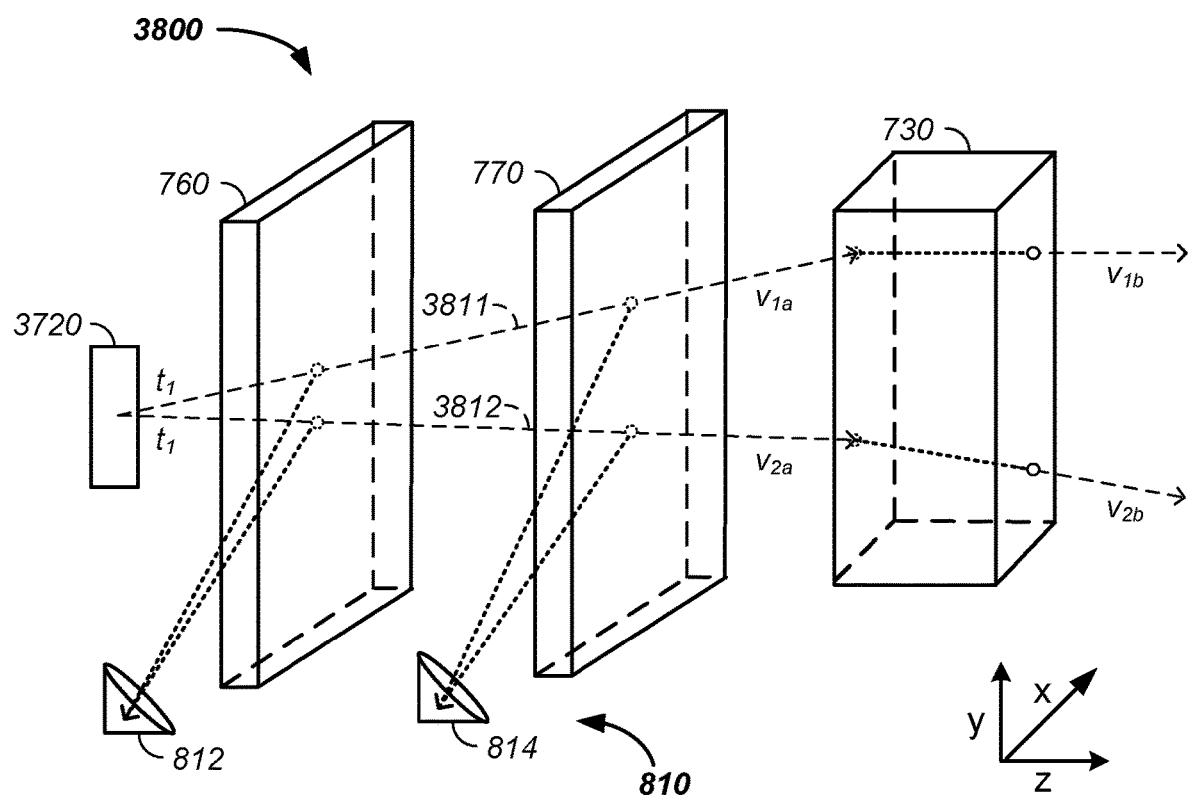

Referring now to FIG. 38A and FIG. 38B, a multiplexed proton imaging system 3800 is illustrated. For clarity of presentation, a proton is used in this section to represent a positively charged particle, such as $C^{4+}$ or $C^{6+}$. As a proton transmits through the patient 730, the proton interacts with the patient 730 and is redirected and/or scattered from a prior vector to a posterior vector. As described, supra, a path of the proton is optionally determined using imaging sheets, which give off photons upon passage of the proton, and photon detectors. However, the rate of imaging is limited by scanning time associated with steering the proton beam and flux rate, as only one proton path at a time is determined due to the relaxation time of the imaging sheets and scintillation material 710. Imaging multiple proton paths simultaneously, referred to as multiplexed proton imaging, is described herein.

Still referring to FIG. 38A and FIG. 38B, multiple protons are directed by the nozzle system 146 along a given vector at a given time, where herein a simultaneous time is a time period between passage of protons less than a relaxation time of the imaging sheets, a relaxation time of the scintillation material 710, a fifty percent decay in flux of emitted photons from an imaging sheet after passage of positively charged particles, and/or less than 0.1, 0.01, 0.001, 0.0001, 0.00001, 0.000001, 0.0000001, or 0.00000001 seconds. The multiple protons in the proton beam are expanded, radially, using a proton beam expander and/or as illustrated using the diffusing element 3720. For clarity of presentation, two proton paths are illustrated at a simultaneous time or first time, $t_1$, but the number of paths simultaneously determined is optionally greater than 2, 3, 4, 5, 10, 50, 100, or 1000. As illustrated, a first prior path 3811 is determined using a first sheet 760 coupled with a first detector 812 and a second sheet 770 optically coupled to a second detector 814. As the first sheet is two dimensional and the first detector 812 is a detector array, a first prior path position of a first proton in the plane of the first sheet is optionally and preferably determined at the same as a second prior path position of a second proton in the plane of the first sheet. The process is repeated using the second sheet 770 and the second detector and the results combined to determine the first prior path 3811 and the second prior path 3812 of the simultaneous first and second protons. Similarly, a first posterior vector 3821 and a second posterior vector 3822 are determined using a third sheet 780 and a fourth sheet 790 and associated detectors, not illustrated.

As described, supra, the first prior vector 3811 and the first posterior vector 3822 are used to calculate a first probable path 3831 of the first proton through the patient 730 and the second prior vector 3812 and the second posterior vector 3822 are used to calculated a second probable path 3832 of the second proton through the patient 730. Differences in residual energy between the first proton and the second proton, as detected by depth of penetration into the scintillation material 710, yields additional information as to what materials were encountered in the patient 730 along the first probable path 3831 and the second probable path 3832, respectively.

Still referring to FIG. 38A and FIG. 38B, the efficiency of multiplexing, also referred to as the number of simultaneous proton path determinations, increases as resolution of the detection system increases and/or as even expansion of the proton beam improves, such as with a proton radial beam cross-section expander. Statistically, some sets of simultaneous protons will pass through a set of paths that are not resolved, leading to a software discarding function removing those imaging elements. However, the simultaneous proton paths will probabilistically vary at the next time, such as a second time, $t_2$, and each time thereafter allowing an accumulation of accepted proton imaging paths that increases at a rate faster than a series of individual measurements, such as acquired using a scanning proton beam and/or as limited by relaxation times of the sheets, such as the first sheet 760, and the scintillation material 710 of a scintillation system. Notably, the multiplexed proton imaging system 3800 is optionally and preferably combined with: (1) relative movement/rotation of the patient 730 and nozzle system 146 and associated generation of a three-dimensional image through the use of tomography algorithms and/or (2) variation of an energy of the protons from the synchrotron 130. The multiplexed proton imaging system 3800 is optionally used with the detector array 1410, the set of detector arrays 1700, and/or a non-uniform detector stack of detector layers 3034, described supra.

Double Exposure Imaging

Still referring to FIG. 37B, a method of double exposure imaging is described. Herein, double exposure imaging is performed using hardware. While further processing of the resultant image is optionally and preferably performed, the double exposure occurs at the detector level through exposure to both X-rays and positively charged particles, simultaneously and/or in either order. Subsequent superimposition to overlay an X-ray image and a positively charged particle image is not necessary or required. An example illustrates double exposure imaging.

Example I

Still referring to FIG. 37B, an X-ray and positively charged particle double exposure image is described. As described, supra, the first detector array 1322, responsive to X-rays, is exposed to X-rays, such as the first cone beam 1392 and/or the second cone beam 1394, after passing through the patient 730. Before, after, and/or concurrently, the first detector array 1332 is exposed to the positively charged particles, such as the residual charged particle beam 267, after passing through the patient. Essentially, the first detector array 1322 comprises: (1) a material that is responsive to both X-rays and positively charged particles, such as protons or (2) comprises a composition of materials, where one component is responsive to X-rays and another component is responsive to positively charged particles.

Typically, material of the first detector array 1332 is responsive and/or designed for X-ray detection, but has a smaller, typically much smaller, responsivity to positively charged particles. For instance, for a given thickness of a material, the material may absorb 99% of the X-rays while 90% of incident protons transmit through the material. However, the 10% of the incident protons leave a physical response behind on the essentially X-ray film or slab, which is detected and used to form the positively charged particle aspect of a particle-X-ray image, denoted herein as a pX-double exposure image or pX-image. Generally, a proton interacts with a nucleus via a strong interaction, either elastically or inelastically. In the elastic interaction, the proton scatters at some angle while losing momentum. In the inelastic interaction, the proton is absorbed in the interaction. The two types of interactions interact differently with detector materials. Further, the positively charged particles interact with atomic electrons, which results in a small loss of energy of the proton while knocking an electron out of orbit, such as to a higher energy level or to a free electron, either of which are detectable, such as from secondary emission or electron capture, integration, and flow. The secondary emission is an indirect measurement using a scintillator material that, responsive to transfer of energy from the X-ray and/or particle, emits a photon that is detected using a traditional detector array, such as a photodetector, photodiode array, CCD, and/or thin film transistor. The thin film transistor is optionally additionally used to directly detect the X-ray and/or charged particle. All detectors described herein are optionally and preferably two-dimensional detector arrays. All two-dimensional detector arrays described herein are optionally used, with relative rotation of the imaging beam and the sample, to generate three-dimensional images, such as via tomography.

A first advantage of the X-ray and positively charged particle double exposure image is that both the X-ray and the positively charged particle are optionally delivered simultaneously or near simultaneously, such as within 0.001, 0.01, 0.1, 1, 2, 5, or 10 seconds of one another, which allows a double exposure of the patient in a fixed position, such as between patient movement, respirations, and/or twitches, each of which complicate overlaying images in software in terms of position, rotation, and non-linear distortion.

A second advantage of the X-ray and positively charged particle double exposure two-dimensional image is that the X-ray and the positively charged particles interact with different components of the patient 730 and/or interact differently with the same components of the patient 730. Thus, the resultant image has more information than a purely X-ray image, where the additional fully integrated signal, the pX-image, results from the interaction of the positively charged particles and the patient 730.

Dual Exposure Imaging

Still referring to FIG. 37B, dual exposure imaging is described. While double exposure imaging, as used herein, exposes a detector material using both X-rays and positively charged particles, a dual exposure image uses the positively charged particles to expose two detectors.

In one case, the positively charged particles expose the essentially X-ray detector to form the pX-image, and residual imaging particles 3730, after passing through the pX-image detector, are detected using a charged particle detector, such as the scintillation material 710. If the X-ray detector also uses scintillation, the X-ray detector is referred to herein as a first scintillation material and the scintillation material 710 is referred to herein as a second scintillation material. In the first case, the multitude of charged particles interact with the pX-image detector using any of the mechanisms described above. In another case, a given charged particle, of an imaging set of the positively charged particles, interacts, such as elastically, with the first essentially X-ray detector and proceeds to interact with the second scintillation material. Thus, as described above, a portion of the set of positively charged particles interact with the pX-ray detector and an intersecting and/or non-intersection portion of the set of positively charged particles interact with the scintillation material 710.

Still yet another embodiment includes any combination and/or permutation of any of the elements described herein.

The main controller, a localized communication apparatus, and/or a system for communication of information optionally comprises one or more subsystems stored on a client. The client is a computing platform configured to act as a client device or other computing device, such as a computer, personal computer, a digital media device, and/or a personal digital assistant. The client comprises a processor that is optionally coupled to one or more internal or external input device, such as a mouse, a keyboard, a display device, a voice recognition system, a motion recognition system, or the like. The processor is also communicatively coupled to an output device, such as a display screen or data link to display or send data and/or processed information, respectively. In one embodiment, the communication apparatus is the processor. In another embodiment, the communication apparatus is a set of instructions stored in memory that is carried out by the processor.

The client includes a computer-readable storage medium, such as memory. The memory includes, but is not limited to, an electronic, optical, magnetic, or another storage or transmission data storage medium capable of coupling to a processor, such as a processor in communication with a touch-sensitive input device linked to computer-readable instructions. Other examples of suitable media include, for example, a flash drive, a CD-ROM, read only memory (ROM), random access memory (RAM), an application-specific integrated circuit (ASIC), a DVD, magnetic disk, an optical disk, and/or a memory chip. The processor executes a set of computer-executable program code instructions stored in the memory. The instructions may comprise code from any computer-programming language, including, for example, C originally of Bell Laboratories, C++, C#, Visual Basic® (Microsoft, Redmond, Wash.), Matlab® (MathWorks, Natick, Mass.), Java® (Oracle Corporation, Redwood City, Calif.), and JavaScript® (Oracle Corporation, Redwood City, Calif.).

Herein, any number, such as 1, 2, 3, 4, 5, is optionally more than the number, less than the number, or within 1, 2, 5, 10, 20, or 50 percent of the number.

Herein, an element and/or object is optionally manually and/or mechanically moved, such as along a guiding element, with a motor, and/or under control of the main controller.

The particular implementations shown and described are illustrative of the invention and its best mode and are not intended to otherwise limit the scope of the present invention in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

In the foregoing description, the invention has been described with reference to specific exemplary embodiments; however, it will be appreciated that various modifications and changes may be made without departing from the scope of the present invention as set forth herein. The description and figures are to be regarded in an illustrative manner, rather than a restrictive one and all such modifications are intended to be included within the scope of the present invention. Accordingly, the scope of the invention should be determined by the generic embodiments described herein and their legal equivalents rather than by merely the specific examples described above. For example, the steps recited in any method or process embodiment may be executed in any order and are not limited to the explicit order presented in the specific examples. Additionally, the components and/or elements recited in any apparatus embodiment may be assembled or otherwise operationally configured in a variety of permutations to produce substantially the same result as the present invention and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. A method for imaging a tumor of a patient using positively charged particles and X-rays, comprising the steps of:
   rotating elements of an X-ray imaging system, configured to deliver the X-rays, around both a first rotation axis and the patient;
   imaging the patient using the X-rays from said X-ray imaging system;
   passing the positively charged particles through an exit port of a nozzle system, said nozzle system connected to a synchrotron via a first beam transport line, the positively charged particles passing into the patient from the exit port along a z-axis and at least one of: (1) treating the tumor with the positively charged particles and (2) imaging the patient with residual charged particles comprising the positively charged particles after transmitting through the patient;
   disconnecting said nozzle system from said first beam transport line;
   moving said nozzle system; and
   after said step of moving, connecting said nozzle system to a second beam line to direct the positively charged particles toward the patient at a different relative angle.

2. An apparatus for imaging a tumor of a patient using positively charged particles and X-rays, comprising:
   a rotatable X-ray imaging system, configured to deliver the X-rays, around both a first rotation axis and the patient;
   an X-ray imaging system configured to image the patient using the X-rays; an exit port nozzle of a nozzle system connected to a synchrotron via a beam transport line, said exit port configured to pass the positively charged particles, the positively charged particles passing, during use, into the patient from the exit port along a z-axis to treat the tumor;
   a gantry configured to move said exit port along an arc, the z-axis maintaining a path from the exit port to the patient as said exit port moves along the arc;
   a main controller configured to rotate a source end of said X-ray imaging system and a detector end of said X-ray imaging system about the first rotation axis, the first rotation axis perpendicular to a z-axis, wherein, while said gantry moves said exit port along said arc and said main controller rotates said X-ray imaging system, said main controller configured to: (1) collect a first set of images of the patient using the positively charged particles and (2) collect a second set of images of the patient using the X-rays.

3. The apparatus of claim 2, further comprising:
a first cone beam X-ray source and a second cone beam X-ray source, of said X-ray imaging system, positioned on a first side of the patient, said first cone beam X-ray source and said second cone-beam X-ray source separated by at least twenty centimeters; and
at least one two-dimensional X-ray detector, of said X-ray imaging system, configured to detect X-rays from said first cone beam X-ray source, said at least one two-dimensional X-ray detector connected to said X-ray imaging system on an opposite side of the patient from said first cone beam X-ray source.

4. The apparatus of claim 3, further comprising:
a gantry supporting said nozzle system, wherein a mean treatment beam axis of the positively charged particles and a mean X-ray beam axis of X-rays from said first cone beam X-ray source form an angle of greater than twenty degrees and less than seventy degrees as projected onto a flat surface parallel said mean X-ray beam axis and said mean treatment beam axis of the positively charged particles.

5. The apparatus of claim 3, further comprising:
a set of fiducial indicators, a first member of said set of fiducial indicators connected to said nozzle system and a second member of said set of fiducial indicators connected to said X-ray imaging system.

6. The apparatus of claim 5, further comprising:
a main controller configured to gather data from said fiducial indicators and using the data determine if a path from said exit nozzle to the patient is unobstructed.

* * * * *